(12) United States Patent
Potts et al.

(10) Patent No.: US 12,131,262 B2
(45) Date of Patent: Oct. 29, 2024

(54) DATA STORAGE AND RETRIEVAL SYSTEM INCLUDING A KNOWLEDGE GRAPH EMPLOYING MULTIPLE SUBGRAPHS AND A LINKING LAYER INCLUDING MULTIPLE LINKING NODES, AND METHODS, APPARATUS AND SYSTEMS FOR CONSTRUCTING AND USING SAME

(71) Applicant: PAREXEL International, LLC, Waltham, MA (US)

(72) Inventors: Christopher Potts, Palo Alto, CA (US); Kevin Reschke, San Mateo, CA (US); Nick Dingwall, Truro (GB); Abhilash Itharaju, Fremont, CA (US)

(73) Assignee: PAREXEL International, LLC, Waltham, MA (US)

( * ) Notice: Subject to any disclaimer, the term of this patent is extended or adjusted under 35 U.S.C. 154(b) by 410 days.

(21) Appl. No.: 17/355,046

(22) Filed: Jun. 22, 2021

(65) Prior Publication Data
US 2022/0129766 A1    Apr. 28, 2022

Related U.S. Application Data

(63) Continuation of application No. PCT/US2019/068416, filed on Dec. 23, 2019.
(Continued)

(51) Int. Cl.
*G06F 16/00* (2019.01)
*G06F 16/25* (2019.01)
(Continued)

(52) U.S. Cl.
CPC .............. *G06N 5/02* (2013.01); *G06F 16/258* (2019.01); *G06F 40/211* (2020.01); *G06F 40/30* (2020.01)

(58) Field of Classification Search
CPC .......... G06N 5/02; G06N 20/00; G06N 5/022; G06F 16/258; G06F 40/211; G06F 40/30;
(Continued)

(56) References Cited

U.S. PATENT DOCUMENTS

| 5,450,535 A | 9/1995 | North |
| 8,452,851 B2 | 5/2013 | Kabiljo et al. |

(Continued)

OTHER PUBLICATIONS

Zaki et al., Knowledge Graph Construction and Search for Biological Databases, 2017 (ICRIIS), Jul. 16-17, 2017, retrieved on Nov. 28, 2023, retrieved from the Internet <URL: https://ieeexplore.ieee.org/stamp/stamp.jsp?tp=&arnumber=8002465> (Year: 2017).*

(Continued)

*Primary Examiner* — Tyler J Torgrimson
(74) *Attorney, Agent, or Firm* — Wolf, Greenfield & Sacks, P.C.

(57) ABSTRACT

A graph-based data storage and retrieval system in which multiple subgraphs representing respective datasets in different namespaces are interconnected via a linking or "canonical" layer. Datasets represented by subgraphs in different namespaces may pertain to a particular information domain (e.g., the health care domain), and may include heterogeneous datasets. The canonical layer provides for a substantial reduction of graph complexity required to interconnect corresponding nodes in different subgraphs, which in turn offers advantages as the number of subgraphs (and the number of corresponding nodes in different subgraphs) increases for the particular domain(s) of interest. Examples of such advantages include reductions in data storage and retrieval times, and enhanced query/search efficacy, discovery of relationships in different parts of the system, ability to infer relationships in different parts of the system, and ability to train data models for natural language processing (NLP)

(Continued)

and other purposes based on information extracted from the system.

15 Claims, 40 Drawing Sheets

Related U.S. Application Data

(60) Provisional application No. 62/786,903, filed on Dec. 31, 2018, provisional application No. 62/784,652, filed on Dec. 24, 2018.

(51) Int. Cl.
*G06F 40/211* (2020.01)
*G06F 40/30* (2020.01)
*G06N 5/02* (2023.01)

(58) Field of Classification Search
CPC ...... G06F 16/367; G16H 70/20; G16H 70/40; G16H 70/60
See application file for complete search history.

(56) References Cited

U.S. PATENT DOCUMENTS

| | | |
|---|---|---|
| 8,996,555 B2 | 3/2015 | Kuchmann-Beauger et al. |
| 10,262,030 B1 | 4/2019 | Burtenshaw et al. |
| 11,263,391 B2 | 3/2022 | Potts et al. |
| 2002/0059069 A1 | 5/2002 | Hsu et al. |
| 2002/0107844 A1 | 8/2002 | Cha et al. |
| 2003/0033277 A1 | 2/2003 | Bahulkar et al. |
| 2003/0069908 A1 | 4/2003 | Anthony et al. |
| 2003/0149685 A1 | 8/2003 | Trossman et al. |
| 2003/0212544 A1 | 11/2003 | Acero et al. |
| 2005/0027664 A1 | 2/2005 | Johnson et al. |
| 2005/0090911 A1 | 4/2005 | Ingargiola et al. |
| 2005/0273730 A1 | 12/2005 | Card et al. |
| 2006/0036568 A1 | 2/2006 | Moore et al. |
| 2006/0248045 A1 | 11/2006 | Toledano et al. |
| 2007/0106499 A1 | 5/2007 | Dahlgren et al. |
| 2008/0172407 A1 | 7/2008 | Sacks |
| 2011/0252355 A1 | 10/2011 | Nixon et al. |
| 2011/0264291 A1 | 10/2011 | Le Roux et al. |
| 2011/0295788 A1 | 12/2011 | Kowalski |
| 2012/0072468 A1 | 3/2012 | Anthony et al. |
| 2012/0259895 A1 | 10/2012 | Neely, III et al. |
| 2013/0151572 A1 | 6/2013 | Brocato et al. |
| 2013/0262449 A1 | 10/2013 | Arroyo et al. |
| 2013/0262501 A1 | 10/2013 | Kuchmann-Beauger et al. |
| 2013/0332438 A1 | 12/2013 | Li et al. |
| 2014/0059084 A1 | 2/2014 | Adams et al. |
| 2014/0098101 A1 | 4/2014 | Friedlander et al. |
| 2014/0244325 A1 | 8/2014 | Cartwright |
| 2014/0258301 A1 | 9/2014 | Misra et al. |
| 2014/0337306 A1 | 11/2014 | Gramatica |
| 2015/0117216 A1 | 4/2015 | Anand et al. |
| 2015/0350440 A1 | 12/2015 | Steiner et al. |
| 2015/0370787 A1 | 12/2015 | Akbacak et al. |
| 2016/0162458 A1 | 6/2016 | Munro et al. |
| 2016/0267128 A1 | 9/2016 | Dumoulin et al. |
| 2016/0275196 A1 | 9/2016 | Lee et al. |
| 2016/0311113 A1 | 10/2016 | Markey et al. |
| 2017/0270418 A1 | 9/2017 | Reschke et al. |
| 2017/0277841 A1 | 9/2017 | Shankar et al. |
| 2017/0308620 A1 | 10/2017 | Cao et al. |
| 2018/0075359 A1 | 3/2018 | Brennan et al. |
| 2018/0081937 A1 | 3/2018 | Broecheler |
| 2018/0121500 A1 | 5/2018 | Rescchke et al. |
| 2018/0121546 A1 | 5/2018 | Dingwall et al. |
| 2019/0034591 A1 | 1/2019 | Mossin et al. |
| 2020/0293712 A1 | 9/2020 | Potts et al. |
| 2021/0191924 A1 | 6/2021 | Reschke et al. |
| 2022/0253594 A1 | 8/2022 | Potts et al. |

OTHER PUBLICATIONS

International Search Report and Written Opinion mailed Jan. 17, 2018 in connection with International Application No. PCT/US2017/058864.

International Preliminary Report on Patentability mailed Apr. 30, 2019 in connection with International Application No. PCT/US2017/058864.

International Search Report and Written Opinion mailed May 5, 2020 in connection with International Application No. PCT/US2019/068416.

Invitation to Pay Additional Fees for International Application No. PCT/US2019/068416 mailed Feb. 24, 2020.

International Search Report and Written Opinion mailed Jun. 15, 2020 in connection with International Application No. PCT/US2020/022107.

International Search Report and Written Opinion mailed Feb. 2, 2018 in connection with International Application No. PCT/US2017/058859.

International Search Report and Written Opinion mailed May 26, 2017 in connection with International Application No. PCT/US2017/022483.

International Preliminary Report on Patentability mailed Sep. 23, 2021 in connection with International Application No. PCT/US2020/022107.

Extended European Search Report dated Aug. 12, 2022 in connection with European Application No. 19902557.8.

[No Author Listed], Data modeling. Wikipedia. Oct. 2018. 8 pages. URL:https://en.wikipedia.org/wiki/data_modeling [last accessed Dec. 14, 2018].

[No Author Listed], Transform Complex Text Documents into Data, Insights, & Value. 2022, 12 pages. URL:https://www.lexalytics.com [last accessed Aug. 15, 2022].

Eifrem, How Graph Search Works. Jun. 13, 2013. 2 pages. URL:https://neo4j.com/news/how-graph-search-works.

Fellbaum [ed], WordNet: An Electronic Lexical Database. 1998, 6 pages. MIT Press.

Forest et al., Dedupe. 2022, 5 pages. URL:https://github.com/datamade/dedupe. [last accessed Apr. 7, 2022].

Gawriljuk et al., A scalable approach to incrementally building knowledge graphs. International conference on theory and practice of digital libraries. Sep. 2016, pp. 188-199.

Kaufmann et al., Evaluating the usability of natural language query languages and interfaces to Semantic Web knowledge bases. Journal of Web Semantics. Nov. 2010;8(4):377-93. DOI:10.1016/j.websem.2010.06.001.

Li et al., Under the hood: The natural language interface of Graph Search. Apr. 29, 2013. 9 pages. URL:https://code.facebook.com/posts/316353631844205/under-the-hood-the-natural-language-interface-of-graph-search [last accessed Apr. 7, 2022].

Park et al., Introducing: Project open data. May 16, 2013. 3 pages. URL:https://www.whitehouse.gov/blog/2013/05/16/introducing-project-open-data [last accessed Apr. 7, 2022].

Reddy et al., Large-scale semantic parsing without question-answer pairs. Transactions of the Association for Computational Linguistics. Dec. 1, 2014;2:377-92.

Rui et al., Visualization and Forecast Analysis of Science and Technology Intelligence Based on Knowledge Graph. 2018 17th International Symposium on Distributed Computing and Applications for Business Engineering and Science (DCABES). Oct. 2018, pp. 44-47.

Setia, Create a knowledge base using domain specific documents and the mammoth python library. Jun. 17, 2018. 6 pages. URL:http://web.archive.org/web/20180617181315/https://github.com/IBM/build-knowledge-base-with-domain-specific-documents [last accessed Jul. 27, 2022].

Stichbury, WTF is a knowledge graph? Hacker Noon. May 10, 2017. 10 pages. URL:https://hackernoon.com/wtf-is-a-knowledge-graph-a16603a1a25f [last accessed Nov. 17, 2018].

Sun et al., Data Processing and Text Mining Technologies on Electronic Medical Records: A Review. Hindawi. Journal of Health-

(56) References Cited

OTHER PUBLICATIONS care Engineering. Apr. 2018. 10 pages. URL:https://www.hindawi.com/journals/jhe/2018/4302425 [last accessed Aug. 15, 2022].

Yankova, Text Mining & Graph Databases—Two Technologies that Work Well Together. Jul. 5, 2014. 7 pages. URL:https://www.ontotext.com/blog/text-mining-graph-databases-work-well-together [last accessed Aug. 15, 2022].

Zettlemoyer et al., Online learning of relaxed CCG grammars for parsing to logical form. Proceedings of the 2007 Joint Conference on Empirical Methods in Natural Language Processing and Computational Natural Language Learning (EMNLP-CoNLL). Jun. 2007, pp. 678-687.

* cited by examiner

| Dataset | Type of shading in Figures 10A and 10B | Description |
|---|---|---|
| National Provider Identifier |  | Registry of healthcare providers |
| CMS Physician Compare | 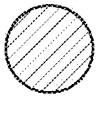 | Data on physicians and their practices |
| CMS Open Payments Research | 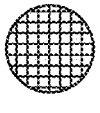 | Research support by manufacturers |
| Healthcare Taxonomy |  | Three-level classification of medical specialties |
| CMS Prescriptions |  | Prescriptions written under Medicare Part D |
| FDA Drug Labels |  | Drugs and their associated regulated metadata |

TABLE 1

FIG. 10C

| PARSE TREE | LOGICAL FORM | CYPHER STATEMENT | RESULTS |

```
MATCH (cmsprescriptions_provider1:`CMSPrescriptions/Provider`)
MATCH (cmsprescriptions_provider1:`CMSPrescriptions/Provider`)-
[cmsprescriptions_provider_prescribed_cmsprescriptions_cmsdrug1:`PRESCRIBED`]
->(cmsprescriptions_cmsdrug1:`CMSPrescriptions/CMSDrug`)
MATCH (cmsprescriptions_cmsdrug1:`CMSPrescriptions/CMSDrug`)
MATCH (cmsprescriptions_cmsdrug1:`CMSPrescriptions/CMSDrug`)-
[cmsprescriptions_cmsdrug_instance_of_cmsprescriptions_drug1:`INSTANCE OF`]
->(cmsprescriptions_cmsdrug1:`CMSPrescriptions/Drug`)
MATCH (cmsprescriptions_drug1:`CMSPrescriptions/Drug` { uuid:`CMSPrescriptions/Drug/Januvia` })
MATCH (cmsprescriptions_provider1:`CMSPrescriptions/Provider`)-
[cmsprescriptions_provider_state_cmsprescriptions_state1:`STATE`]->(cmsprescriptions_state1
:`CMSPrescriptions/State`)
MATCH cmsprescriptions_state1:`CMSPrescriptions/State` { uuid: `CMSPrescriptions/State/NY` })
RETURN
cmsprescriptions_provider_prescribed_cmsprescriptions_cmsdrug1.total_claim_count,
cmsprescriptions_provider1
ORDER BY cmsprescriptions_provider_prescribed_cmsprescriptions_cmsdrug1.total_claim_count DESC
LIMIT 10
```

FIG. 12C

```
python -m rkg.to_roam Graphitect \
config_path="/data/warehouse/code/roamkg/rkg/rkg/settings/graphitect_confi
g_files/<namespace.json file>" \
    data_dirextory=s3://roam-import/graph_builder_data/public/"
--only_build
```

FIG. 35

DATA STORAGE AND RETRIEVAL SYSTEM INCLUDING A KNOWLEDGE GRAPH EMPLOYING MULTIPLE SUBGRAPHS AND A LINKING LAYER INCLUDING MULTIPLE LINKING NODES, AND METHODS, APPARATUS AND SYSTEMS FOR CONSTRUCTING AND USING SAME

CROSS-REFERENCE TO RELATED APPLICATIONS

This application is a continuation of International Application No. PCT/US2019/068416, filed on Dec. 23, 2019, entitled "Constructing a Knowledge Graph Employing Multiple Subgraphs and a Linking Layer Including Multiple Linking Nodes," which claims a priority benefit to U.S. Application No. 62/784,652, entitled "Data Storage and Retrieval System Including a Knowledge Graph Employing Multiple Subgraphs and a Linking Layer Including Multiple Linking Nodes, and Methods, Apparatus and Systems for Constructing and Using Same," filed on Dec. 24, 2018, the disclosure of which is incorporated herein by reference in its entirety. International Application No. PCT/US2019/068416 also claims a priority benefit to U.S. Application No. 62/786,903, entitled "Methods and Systems for Defining Graph Schemas to Represent Data that Includes one or more Structured Fields," filed on Dec. 31, 2018, the disclosure of which is incorporated herein by reference in its entirety.

BACKGROUND

Conventionally, data systems organize data into discrete sets and using standardized identifiers, categories, and characteristics. This organization enables easier and faster searching by organizing data published or consolidated by a single entity. Data systems search differing data sets, published across multiple entities, encounter difficulties in correlating organizational structures. Further difficulties are encountered where data sets are provided in differing formats. While conventional data systems may be able to retrieve distinct documents or elements from multiple data sets, these data systems often provide the documents with no context or relation to other documents presented within the same or similar search results. As a result, conventional data systems attempting to draw inferences or determine links between data sets often present results with unacceptable degrees of uncertainty

SUMMARY

The Inventors have recognized and appreciated that many things, if not everything-a name, a number, a date, an event description-acquires greater meaning in context, where it can be compared with other things. Context is essential for understanding, and the more context one has, the fuller one's understanding can be. The more we know about something, the better we can understand what it is, how it works, what it does, and how it effects the world around it. Individual pieces of information or relatively confined sources of data are often unlikely to provide sufficient context to facilitate a deeper understanding of the meaning of the information at hand. Even with relatively larger amounts of information available, respective pieces of information may remain unconnected, inconsistent or disjointed in some manner, and relationships between certain pieces of information may not be readily apparent or even discernible from the respective (and often unconnected, inconsistent, or disjointed) pieces.

In view of the foregoing, the Inventors also have recognized and appreciated that multiple advantages leading to increased understanding of information are provided by connecting multiple pieces of information to the wider world from which they are extracted. Failure to make these connections is tantamount to pretending the world is less complex than it is. Accordingly, the Inventors have conceived of an inventive data storage and retrieval system that significantly facilitates the interconnection of multiple separate pieces of information (also referred to herein as "datasets") that may in some instances be heterogeneous in nature and obtained/derived from a wide variety of different sources. Various implementations of such an inventive data storage and retrieval system employ a knowledge graph including a unifying "linking layer" (also referred to as a "canonical layer") that provides a frame of reference for meaningfully connecting multiple subgraphs respectively representing diverse datasets.

In various aspects discussed in greater detail below, understanding information and its context via the inventive data storage and retrieval system disclosed herein enables new discoveries and provides a stronger basis for influencing and/or controlling complex real-world interactions (between and among various entities). Additionally, exposing the context of data and its interrelationships with other data significantly enhances the ability to analyze the data and model it to make predictions and derive meaning from new data. In particular, data models based in part on information that is connected via the data storage and retrieval system disclosed herein, and the greater context this system provides, may be used to analyze new data in a more automated and meaningful way to enable actionable consequences for influencing and controlling complex real-world interactions. In yet another aspect, the inventive data storage and retrieval system disclosed herein particularly facilitates the storage and automated/semi-automated analysis and modeling of large bodies of text corpora.

Accordingly, it should be readily appreciated by those of skill in the relevant arts that the inventive concepts disclosed herein are firmly rooted in computer technology (e.g., inventive data storage and retrieval structures) and provide multiple technological solutions that improve the function of computers themselves (e.g., faster, more efficient, more reliable, more intelligible, and more expansive data search, data retrieval, and data modeling functionalities). Furthermore, the various technological solutions disclosed herein are not well-known, conventional, and/or well understood in the conventional arts to which the concepts disclosed herein pertain.

It should be appreciated that all combinations of the foregoing concepts and additional concepts discussed in greater detail below (provided such concepts are not mutually inconsistent) are contemplated as being part of the inventive subject matter disclosed herein. It should also be appreciated that terminology explicitly employed herein that also may appear in any disclosure incorporated by reference or in any appendix (e.g., Appendix A included herewith) should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 10C is a table providing a legend of the datasets depicted in FIGS. 10A and 10B.

FIG. 12C illustrates an example Cypher query generated by a semantic parsing engine, according to one inventive implementation.

FIG. 35 illustrates an example Python script that takes a configuration file output from Graphitect to generate one or more graph files, according to one inventive implementation.

DETAILED DESCRIPTION

Figure 1:
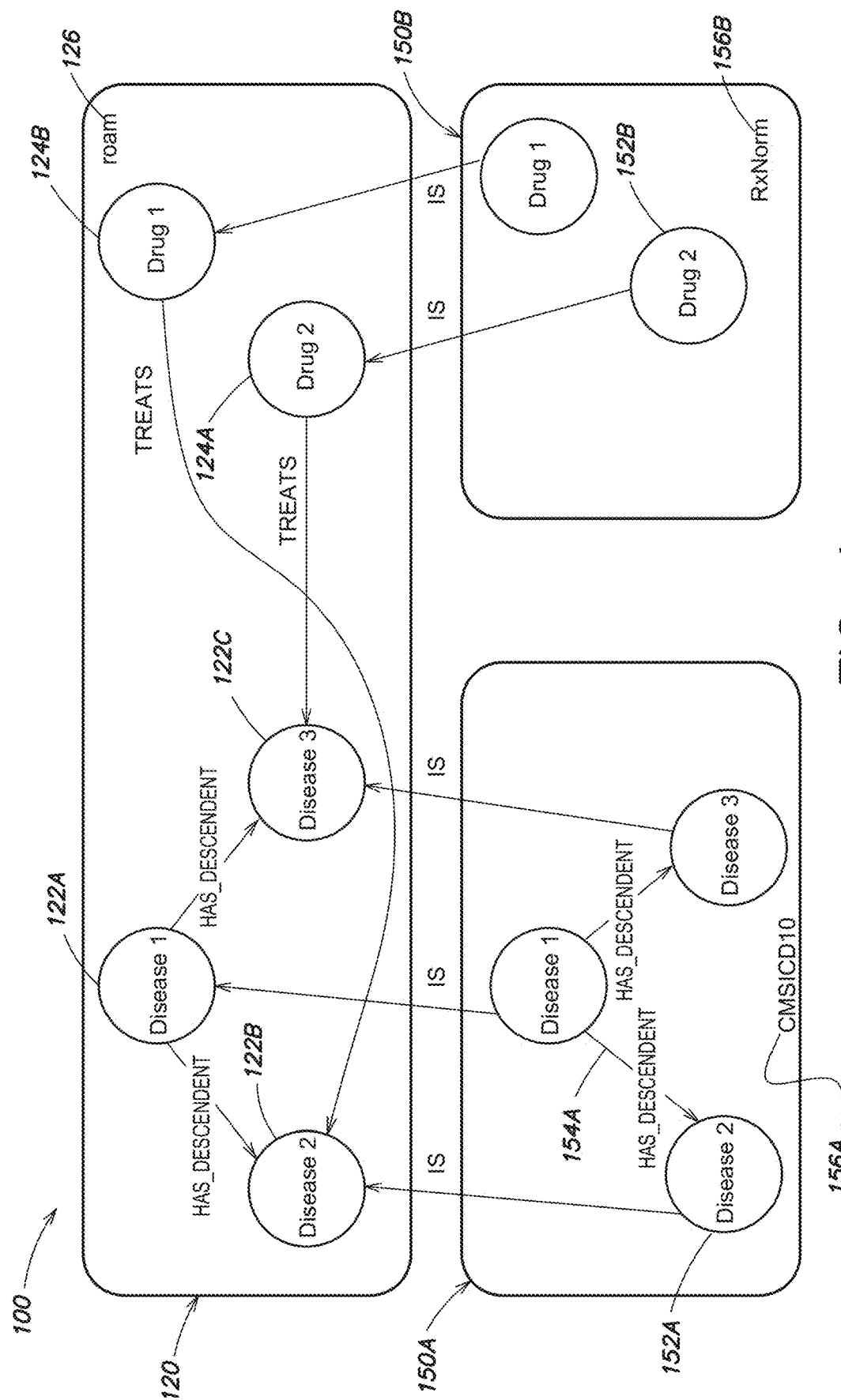
FIG. 1 illustrates an example of an inventive graph-based data storage and retrieval structure referred to herein as a Roam Knowledge Graph (RKG), according to various implementations.

Following below are a glossary of terms and detailed descriptions of various concepts related to, and embodiments of, a data storage and retrieval system including a knowledge graph employing multiple subgraphs and a linking layer, and methods, apparatus and systems for constructing and using such a system. It should be appreciated that various concepts discussed herein may be implemented in multiple ways, as the disclosed concepts are not limited to any particular manner of implementation. Examples of specific implementations and applications are provided herein primarily for illustrative purposes.

The figures and example implementations described below are not meant to limit the scope of the present disclosure to the example implementations discussed herein. Other implementations are possible by way of interchange of at least some of the described or illustrated elements. Moreover, where certain elements of the disclosed example implementations may be partially or fully instantiated using known components, in some instances only those portions of such known components that are necessary for an understanding of the present implementations are described, and detailed descriptions of other portions of such known components are omitted so as not to obscure the salient inventive concepts underlying the example implementations.

Glossary

Information Domain-A "domain" refers to an area of particular activity and/or knowledge. A domain may define or encompass a set of common or shared subjects (e.g., people and/or things), ideologies, academic or research areas, professions, disciplines, concepts, characteristics, requirements, and/or terminology. Examples of domains include, but are not limited to, health care (discussed further below), finance, insurance, e-commerce, entertainment, law, sports, social media, transportation, energy resources and consumption, climate science, education, agriculture, housing, immigration, and other scientific/academic endeavors. Some domains may include one or more subdomains, and one or more subdomains in a given domain may be nested inside one another; additionally, respective domains or subdomains may overlap with one another to some extent (e.g., the health care domain may include a "medical tests" subdomain and a "surgical procedures" subdomain, wherein some tests don't involve surgery, some surgeries are not tests, but some biopsies are arguably both medical tests and surgical procedures). An "information domain" refers to any electronic information in various forms pertaining to a particular domain (including one or more subdomains if applicable).

Health Care Domain—As an example of a domain, the "health care domain" encompasses a wide variety of activity and knowledge relating to human health and well-being.

Examples of such activity and knowledge include but are not limited to: the study and treatment of various ailments and diseases; mitigation and prevention of various ailments and diseases; various forms and techniques of care; diagnoses and administration of drugs; formulation of new drugs, diagnoses and treatments; genes and their relationship to phenotypic expression; various specializations and credentialing for health care practitioners; health care economics, insurance and regulation; and patient demographics. Various electronic information pertaining to the health care domain (e.g., the "health care information domain") includes, but is not limited to, public health statistics and databases, adverse event databases, medical ontologies, regulatory documents, insurance company policy documents, electronic medical records, patient surveys, insurance claims, Medical Science Liaison (MSL) notes, and Medical Information Requests (MIRs).

Dataset-A "dataset" refers to one or more electronic files provided by a particular source. Examples of sources that may provide a dataset include, but are not limited to, business entities (public or private companies), academic institutions, research organizations, government agencies, non-profit organizations, news outlets, and individuals. In some instances, multiple files included in a dataset include information that in some respects is related and relevant to the source of the dataset. One or more files in a dataset may include, for example, data that was generated by the source, data that was collected by the source, data that was received by the source, and/or data that was generated, collected and/or received by the source and modified or curated in some manner by the source. Multiple files in a given dataset may in some instances represent different tables of a database. The file(s) in a dataset may have any of a number of different formats, and multiple files in a dataset may have the same format or different formats. In some examples, a dataset may include a single .csv file (comma-separated values file) or multiple .csv files obtained from a given source.

Fundamental/Golden Dataset—In some implementations discussed herein, a "fundamental dataset" (also referred to as a "golden dataset") refers to a dataset of factual information from a trusted (and often public) source (e.g., a list of United States zip codes obtained from the U.S. Postal Service; National Provider Identifier (NPI) records obtained from the National Plan and Provider Enumeration System (NPPES) of the U.S. Department of Health and Human Services).

Structured Data-"Structured data" refers to multiple data elements than can be meaningfully aggregated, and that generally are organized into a formatted repository of data elements (e.g., a spreadsheet or database including one or more tables with rows and columns), so that respective elements of the data are addressable and easily accessible and searchable (e.g., for processing and analysis). In one aspect, respective data elements of structured data are numerical and on the same or similar scale; in this case, examples of meaningful aggregation may include, but are not limited to, sums or averages. In another aspect, respective data elements of structured data may be numeric, alphanumeric or text-based, and come from a fixed set of possible values (e.g., U.S. states, shoe sizes, a predetermined set of email addresses); in this case, examples of meaningful aggregations may include, but are not limited to, counts of each unique value from the fixed set of possible values. In yet another aspect, at least some data elements of structured data may be normalized (see below). In yet another aspect, a given spreadsheet, database or file may include one or more elements of structured data, together with one or more other elements of unstructured data (see below) (e.g., one or more columns of a spreadsheet may include a defined range of numerical values, while one or more other columns of the spreadsheet may include free form text).

Unstructured Data-"Unstructured data" refers to data that either does not have a pre-defined data model or is not organized in a pre-defined manner. Unstructured data is typically text-heavy (e.g., human language), and may contain data such as dates, numbers, and facts as well. Unstructured data is not associated with any tags or metadata about the data, and it has no established schema. This generally results in irregularities and ambiguities in the unstructured data that make it relatively difficult to understand, access, search, and process using traditional programs (as compared to data stored in databases, for example). Examples of unstructured data include, but are not limited to, the body of e-mail messages, word processing documents, videos, photos, audio files, presentations, webpages, and various kinds of business or regulatory documents.

Semi-structured Data-"Semi-structured data" refers to data that is not in a relational database, but nonetheless has some organizational structure (i.e., a known schema) or carries a tag (e.g., XML extensible markup language used for documents on the web), thereby rendering the data somewhat easier to organize, access, search, and analyze.

Heterogeneous Data/Heterogeneous Datasets-"Heterogeneous data" refers to multiple elements of data (or multiple data files) that vary in type and/or format. A "heterogeneous dataset" refers to a given dataset from a particular source that includes heterogeneous data (e.g., one or more files having different types of data and/or multiple files having respective different formats). "Heterogeneous datasets" refers to respective datasets from different sources wherein the respective datasets vary in type and/or format amongst each other (but any given dataset itself of the multiple datasets may or may not include heterogeneous data).

Normalize/Normalization—The terms "normalize" or "normalization" refer to a process of modifying one or more disparate pieces of data relating to a same or similar thing, such that all of the pieces of data relating to the same or similar thing are homogenized in some manner (e.g., according to a predetermined standard or format). For example, considering a first element of data as "Fort Laud" and a second element of data as "Ft. Lauderdale" (both of which presumably refer to the same city in the state of Florida, U.S.A.), the first element of data may be normalized to "Ft. Lauderdale," the second element of data may be normalized to "Fort Laud," or both the first and second elements of data may be normalized to "Ft. Laud" or another predetermined standard (e.g., the airport code "FLL"). In some examples of normalization, the predetermined standard or format to which one or more data elements are normalized may be an official, widely accepted, certified, and/or pre-ordained format for the data element in question, also referred to herein as a "canonical source." In this respect, when normalization utilizes a canonical source as the target for modifying data elements if/as needed, such a normalization may also be referred to as "canonicalization."

Namespace-A "namespace" is a logical construct for organizing datasets (and multiple files in a given dataset) in computer storage (e.g., a file system). In various implementations discussed herein, a dataset received from a particular source is stored in a namespace associated with the particular source. The namespace itself has an identifier that may be representative of the source (e.g., a namespace for a dataset from the U.S. Postal Service may be labeled as "USPS"). Each element (e.g., a file or other object) within the namespace has a local name that serves as a unique identifier for that element within the namespace (e.g., "zip codes," "States," "Counties"). A namespace makes it possible to distinguish files (or other objects) with similar or identical local names in one or more other namespaces (e.g., files or other objects with similar/identical names that originate from different sources). For example, consider a first dataset of zip codes received from the U.S. Postal Service including the file "California zip codes" logically stored in the namespace "USPS," and a second dataset of zip codes received from a particular state's government records (e.g., California) including the file "California zip codes" logically stored in the corresponding namespace "ca.gov;" in this example, "USPS/California zip codes" may be identified as a different file from "ca.gov/California zip codes" by virtue of the different namespaces, even though the two files have the same local name. In this manner, namespaces may also enable the identification of data provenance (e.g., the file "USPS/zip codes" is known to originate from the USPS source, and the file "ca.gov/zip codes" is known to originate from the California state government source). In general, a namespace is a set of symbols that is used to organize objects so that the objects may be referred to by a same or similar name in one or more other namespaces. Namespaces are commonly structured as hierarchies to allow reuse of names in different contexts (e.g., naming of people with proper names and family surnames, differently-named directories of a computer file system in which a particular file of the same name may be stored in two or more different directories, and computer programming namespaces in which symbols and identifiers pertaining to a particular functionality may be grouped accordingly to avoid name collisions between multiple symbols/identifiers having the same name).

Entity/Entity Type—An "entity" refers to a thing represented in a dataset, and an "entity type" refers to a particular category or label for a given entity or multiple entities sharing at least one common aspect. Examples of different entity types include, but are not limited to, physical/tangible objects, places (geographical references), concepts, legal or professional constructs (e.g., companies, organizations, institutions, government agencies, groups and/or networks, and hierarchies within same), products and/or services and various specifications or other information relating to same, events, occupations or roles, professional and/or academic credentials or specialization, publications, financial information, demographic information, statistical information, health-related information (e.g., diagnoses, medical conditions, symptoms, medical research information), and ontologies (see below). As may be readily appreciated from the foregoing, a given dataset may include data pertaining to a significant number of entities of the same type and/or different types, and there may be a wide variety of different types of entities represented in a given dataset or amongst multiple datasets. An example of a particular entity of the entity type "doctor" is "Dr. Einstein." An example of a particular entity of the entity type "U.S. State" is "California." An example of a particular entity of the entity type "disease" is "lymphoma."

Namespaced Entity Type-A "namespaced entity type" uniquely identifies a set of entities of a given type in a given dataset stored in a corresponding namespace. For example, "U.S. State" is an entity type that may appear in multiple datasets respectively stored in different namespaces, but "USPS/U.S. State" uniquely identifies the collection of U.S. State entities as they are referenced in the USPS dataset from the USPS source.

Relationship-A "relationship" refers to a *nexus* between two entities of the same type or different types. For example, a first relationship between a first entity (e.g., a person "Erunia") and a second entity of a different type (e.g., a town "Kalamazoo") may be "works in" (i.e., Erunia "works in" Kalamazoo). A second relationship between the same first entity (i.e., Erunia) and a third entity of the same type (e.g., a person "Ahmed") may be "works with" (i.e., Erunia "works with" Ahmed).

Attribute—An "attribute" is an identifier, aspect, quality, or characteristic of an entity or a relationship. Examples of attributes for the entity "Dr. Einstein" may be the surname attribute "Einstein," an arbitrary identifier attribute "DR123," and an aspect attribute "retired." An example of an attribute for the relationship "works with" may be the aspect attribute "occasionally."

Dataset Graph/Subgraph-A "dataset graph" (also referred to herein as "subgraph") refers to a graph representation of a dataset (and, in some instances, a normalized dataset). A dataset graph (or subgraph) typically includes multiple nodes (see below) respectively representing different entities in the dataset, and multiple edges interconnecting nodes and respectively representing relationships between entities. A given subgraph typically is associated with a particular namespace (which may indicate a source of the dataset that is represented by the subgraph).

Node-A "node" refers to a graph element that represents an entity in a graph representation of a dataset (or data in general). A node typically has a primary identifier that is independent of a name for the entity that the node represents and that is unique in the namespace for the dataset. As with entities, nodes may be categorized according to different node types, and a given node may be associated with one or more attributes. For example, a node in a graph for the entity "Dr. John Einstein" from the National Provider Identifier (NPI) Registry dataset of health care practitioners stored in the namespace "NPI" may have the unique primary identifier "00642," a node type "Physician," a surname attribute "Einstein," and a professional status attribute "retired."

Edge—An "edge" refers to a graph element that represents a relationship between two entities in a dataset in a graph representation of the dataset. As with nodes, edges may be categorized according to different types (i.e., of relationships), and a given edge may be associated with a unique primary identifier and one or more attributes. In one aspect, a primary identifier for an edge may be denoted as a "triple" including the primary identifier of the from-node, a descriptor for the type of edge, and the primary identifier of the to-node (e.g., "DR76, WORKS_WITH, DR18"). In another aspect, one attribute of an edge may relate to a probability regarding the certainty of the relationship represented by the edge (e.g., a numerical value between 0 and 1, inclusive).

Graph Schema-A "graph schema" for a namespace refers to a model for representing, as a graph of nodes and edges, a dataset (or data in general) logically stored in the namespace. A graph schema defines the types of entities in the dataset that are to be represented by nodes in a graph and the relationships between entities of various types that are to be represented by edges in the graph. The graph schema may also define one or more attributes for a given node and/or edge. Given the variety of actual data elements of respective different entity types that may appear in a given dataset (and the corresponding attributes of each entity type), the graph schema for the namespace may be only partially instantiated when a graph of the dataset is generated. For example, a graph schema for the namespace "NPI" (National Provider Identifier Registry of health care practitioners) may include a first node type "Provider" (a unique identifier representing a single health care practitioner in some instances and a health care organization in other instances), a second node type "Specialty" and a third node type "AuthorizedOfficial." The graph schema may include a first edge of type "has" between node types "Provider" and "Specialty" (e.g., Provider, HAS, Specialty), and a second edge of type "has" between node types "Provider" and "AuthorizedOfficial" (e.g., Provider, HAS, AuthorizedOfficial). In an actual graph instantiated according to this graph schema, there may be no node of type "Provider" that would be connected via HAS edges to both a node of type "Specialty" and a node of type "AuthorizedOfficial;" rather, nodes of type "Provider" for single practitioners could be connected to a node of type "Specialty" and not necessarily to any node of type "AuthorizedOfficial," and nodes of type "Provider" for organizations could be connected to a node of type "AuthorizedOfficial" and not necessarily to any node of type "Specialty."

Ontology—An "ontology" refers to a definition, naming, and representation of categories and properties of entities, and relationships between entities, pertaining to a particular information domain, including subdomains and/or overlapping domains (this is sometimes referred to as a "domain ontology"). An ontology is typically based on logical formalisms that support some form of inference in connection with available data pertaining to the information domain(s), and thereby allows implicit information to be derived from the available explicit data. In this manner, an ontology may in some respects specify the semantics (meaning) of available data pertaining to the information domain(s). Ontologies have been created for some information domains to reduce complexity and organize knowledge and data in the domain(s); this in turn improves communication about the domain(s), and analysis of data and problem solving in the domain(s). In one aspect, an ontology defines a common vocabulary for practitioners who need to share information in a particular domain, and may include machine-interpretable definitions of basic concepts in the domain and relations among the concepts. For example, in the health care domain, health care professionals use ontologies to represent knowledge about symptoms, diseases, and treatments, and pharmaceutical companies use ontologies to represent information about drugs, dosages, and allergies. Some examples of ontologies in the health care domain include, but are not limited to, the Unified Medical Language System from the U.S. National Library of Medicine, RxNorm (drugs), SNOMED CT (Systemized Nomenclature of Medicine), SNOP (Systemized Nomenclature of Pathology), the GALEN Common Reference Model, the National Drug Data File (NDDF), the International Statistical Classification of Diseases and Related Health Problems, a medical classification list by the World Health Organization (ICD10), Chemical Entities of Biological Interest (ChEBI), Current Procedural Terminology (CPT), the Anatomical Therapeutic Chemical (ATC) classification system (classification of active ingredients of drugs according to the organ or system on which they act and their therapeutic, pharmacological and chemical properties, including Defined Daily Doses (DDD)), the International Classification of Functioning, Disability and Health (ICF), LOINC (for health measurements, observations, tests and documents), and the Medical Dictionary for Regulatory Activities (MedDRA).

Knowledge Graph-a "knowledge graph" refers to a graph representation of data (e.g., using nodes to represent entities and edges to represent relationships between entities), wherein the graph representation is based at least in part on one or more datasets and/or ontologies pertaining to a particular information domain. In one aspect, a knowledge graph may be self-descriptive and may provide a single place to find data pertaining to an information domain and understand its meaning (e.g., by virtue of the one or more ontologies on which the knowledge graph is based); in this respect, a knowledge graph encodes the meaning of the data that it represents (e.g., by using node and edge identifiers, types and attributes that are familiar to those interested in, or practitioners of, the information domain). A knowledge graph can be queried to traverse nodes and edges and thereby discover how data from different parts of an information domain may relate to each other. To this end, various graph-computing techniques may be employed (e.g., shortest path computations, network analysis) to uncover "hidden" knowledge represented in the knowledge graph that may be too complex for human cognition. In another aspect, a knowledge graph may be queried in a style that is closer to a natural language (e.g., by virtue of the ontologies employed, which would include vocabulary familiar to practitioners in the domain of interest); this facilitates search and discovery of information encoded in the knowledge graph. In yet another aspect, characteristics pertaining to both nodes and edges in a knowledge graph (e.g., identifiers, types, attributes associated with nodes and edges) may be subjected to computer analytical operations (e.g., being passed as an argument, returned from a function, modified, and assigned to a variable). In yet another aspect, new data items or datasets may be added to a knowledge graph over time; in particular, one or more ontologies on which the knowledge graph is based may be extended and/or revised as new data is considered for addition to the graph, and new entities and/or entity types in datasets may be represented as nodes and connected via edges to existing nodes (based on existing or extended/revised ontologies). This makes knowledge graphs convenient for storing and managing data in use cases where regular data updates and/or data growth are important, particularly when data is arriving from diverse, heterogeneous sources. In yet another aspect, a knowledge graph is also able to capture diverse metadata annotations such as provenance or versioning information, which make a knowledge graph well-suited for working with dynamic datasets.

Roam Knowledge Graph—The "Roam Knowledge Graph" (RKG) is an innovative knowledge graph in which multiple subgraphs representing respective datasets in different namespaces are interconnected via a linking layer (also referred to as a "canonical layer" or "semantic layer," discussed below). In one aspect, the respective datasets represented by subgraphs in different namespaces of an RKG may pertain to a particular information domain and/or overlapping information domains. In other aspects, the respective datasets represented by subgraphs in different namespaces of an RKG may include heterogeneous datasets, and a given dataset represented by a subgraph in a particular namespace of an RKG may include heterogeneous data.

Canonical/Semantic/Linking Layer-A "canonical layer" (also referred to as a "semantic layer" or a "linking layer") of a Roam Knowledge Graph (RKG) refers to a set of linking nodes ("canonical nodes") of predetermined node types ("canonical node types"), wherein the canonical nodes are connected via edges to nodes in respective subgraphs in different namespaces of the RKG. The canonical node types for the canonical nodes of the canonical layer correspond to selected node types that: 1) are present in multiple subgraphs of the RKG, or present in one subgraph of the RKG and likely to appear in one or more other datasets pertaining to the information domain (that may be later added to the RKG as one or more new subgraphs); and 2) have some significance in the information domain(s) (e.g., ontology or ontologies) on which the RKG is based. In the health care information domain, examples of canonical node types include, but are not limited to: disease, drug, FDA device code, FDA device name, geography (e.g., address, census region, city, country, county, geocoordinates, MSA code, state, zip code), health care organization, health care professional, hospital, manufacturer, procedure, industry event, and specialization. The canonical node types present in the canonical layer do not necessarily include all of the node types present in the multiple subgraphs of the RKG (i.e., there may be some node types present in one or more subgraphs that do not have a corresponding canonical node type in the canonical layer of the RKG).

The canonical layer of an RKG generally includes a quantity of canonical nodes that is less than (and sometimes significantly less than) the sum of all nodes present in the multiple subgraphs of the RKG. Each canonical node is unique in the canonical layer (it is only found once in the canonical layer); stated differently, each canonical entity is represented uniquely by only one node in the canonical layer. In some implementations, identical or closely related nodes to a given canonical node appear in at least two subgraphs in different namespaces of the RKG; in this case, at least one canonical node in the canonical layer is connected via multiple edges to at least two corresponding nodes in respective subgraphs in different namespaces of the RKG (and in some implementations all of the canonical nodes are connected to multiple subgraphs in this manner). In other implementations, a given canonical node may be identical or closely related to, and hence connected via an edge to, a subgraph node that only appears in one namespace of the RKG; however, such a canonical node may nonetheless be of particular significance in the information domain(s) such that it is expected to be connected to one or more new subgraph nodes at a future time (e.g., as one or more additional datasets pertaining to the information domain(s) are added to the RKG in corresponding new namespaces).

In another aspect, each edge between a canonical node in the canonical layer and a node in one or more subgraphs of the RKG is one of the following types: "is," "is part of," or "contains." In some implementations, the direction of an edge between a node in one or more subgraphs and a canonical node may be toward the canonical node, but in other implementations the direction of an edge may be from the canonical node to one or more subgraph nodes.

Within the canonical layer of an RKG, a given canonical node may be connected to one or more other canonical nodes via respective edges of a wide variety of types, based at least in part on the diverse relationships that may exist between canonical nodes of the same type or different types. In some instances, edges between subgraph nodes and canonical nodes, or between any two canonical nodes, may be generated based on trained models that predict (based on a variety of criteria coded in logic for the model) that the nodes should be connected (with some corresponding probability).

Artificial Intelligence-Artificial intelligence (AI) is an area of computer science relating to the creation of intelligent machines that work and react like humans, sometimes referred to as "intelligent agents." Some of the activities computers with artificial intelligence are designed for include, but are not limited to, gaining knowledge, reasoning, perception (e.g., speech recognition), learning, planning, problem solving, and manipulating objects. Knowledge engineering is a core part of AI research and the design of intelligent agents; such agents can be designed to act and react like humans only if they have abundant information relating to the world. Artificial intelligence must have access to information regarding various entities (e.g., objects, categories, properties) and relationships between entities, to implement knowledge engineering. Intelligent agents often are designed based on one or more algorithms (i.e., a set of unambiguous instructions that a computer can execute). A complex algorithm for a given intelligent agent is often built on top of other, simpler, algorithms. Many AI algorithms are capable of learning from data; they can enhance themselves by learning new heuristics (strategies that have worked well in the past) or can themselves write other algorithms.

Machine Learning-Machine learning (ML) is a branch of artificial intelligence based on the idea that systems (e.g., intelligent agents) can learn from data, identify patterns and make decisions with minimal human intervention. Thus, ML relates to algorithms and statistical models that intelligent agents use to progressively improve their performance on a specific task. In more formal terms, an intelligent agent based on an ML model learns from experience E with respect to some class of tasks T and performance measure P if its performance at tasks in T, as measured by P, improves with experience E.

Machine learning tasks conventionally are classified into multiple categories. In "supervised learning," an ML algorithm builds a mathematical model of a set of "training data" that contains both the inputs and the desired outputs from performing a certain task. For example, if the task were determining whether an image contained a certain object, the training data for a supervised learning algorithm would include images with and without that object (the input), and each image would have a label (the output) designating whether it contained the object or not. "Semi-supervised learning" algorithms develop mathematical models from incomplete training data, where a portion of the sample inputs are missing the desired output. "Classification" algorithms and "regression" algorithms are types of supervised learning. Classification algorithms are used when the outputs are restricted to a limited set of values (e.g., represented by the Boolean values one and zero), whereas regression algorithms have continuous outputs (e.g., any value within a range of values).

In "unsupervised learning," an ML algorithm builds a mathematical model of a set of data which contains only inputs and no desired outputs. Unsupervised learning algorithms are used to find structure in the data, like grouping or clustering of data points. Unsupervised learning can discover patterns in the data, and can group the inputs into categories, as in "feature learning." "Dimensionality reduction" is the process of reducing the number of "features" (e.g., inputs) in a set of data. "Active learning" algorithms access the desired outputs (training labels) for a limited set of inputs based on a budget and optimize the choice of inputs for which it will acquire training labels. When used interactively, these inputs can be presented to a human user for labeling ("annotation"). Examples of various ML models known in the relevant arts include, but are not limited to, Binary Classification, Multiclass Classification, Linear Regression, Logistic Regression, Decision Tree, Support Vector Machine, Naive Bayes, kNN, K-Means, and Random Forest.

Natural Language Processing-Natural language processing (NLP) is a subfield of artificial intelligence (AI) concerned with the interactions between computers and human (natural) languages (e.g., how to program computers to process and analyze large amounts of natural language data).

NLP generally relies on machine learning (ML) to learn rules for processing languages through the analysis of large corpora (e.g., sets of documents) of typical real-world examples (that may have human or computer annotations). Various classes of ML algorithms have been applied to NLP tasks. These algorithms generally take as input a set of "features" that are generated from the input data. NLP research has increasingly focused on statistical models, which make probabilistic decisions based on attaching real-valued weights to each input feature. Such models have the advantage that they can express the relative certainty of many different possible answers rather than only one, generally producing more reliable results when such a model is included as a component of a larger system.

Roam Knowledge Graph (RKG) Architecture

FIG. 1 illustrates an example of an inventive graph-based data storage and retrieval structure referred to herein as a "Roam Knowledge Graph" (RKG) 100. As noted above, a "knowledge graph" refers to a graph representation of electronic information that may pertain to a particular "domain" or related/overlapping domains of activity and/or knowledge. In various aspects, a Roam Knowledge Graph (RKG) according to the inventive concepts disclosed herein is an effective and highly useful structure for storing and managing data for a variety of use cases and provides specific advantages particularly when data is dynamic (e.g., where regular data updates and/or data growth are important) and when data is heterogeneous and arriving from diverse sources. In other aspects, an RKG particularly facilitates the storage, and automated or semi-automated analysis and modeling, of large bodies of text corpora.

In view of the foregoing, examples of domains for which an RKG similar to that shown in FIG. 1 may be constructed and maintained include, but are not limited to, health care, finance, insurance, e-commerce, entertainment, law, sports, social media, transportation, energy resources and consumption, climate science, education, agriculture, housing, immigration, and other scientific/academic endeavors. In one example discussed herein, an RKG such as the RKG 100 shown in FIG. 1 may specifically pertain to the health care domain, which encompasses a wide variety of activity and knowledge relating to human health and well-being (e.g., the study and treatment of various ailments and diseases; mitigation and prevention of various ailments and diseases; various forms and techniques of care; diagnoses and administration of drugs; formulation of new drugs, diagnoses and treatments; genes and their relationship to phenotypic expression; various specializations and credentialing for health care practitioners; health care economics, insurance and regulation; and patient demographics).

As illustrated in FIG. 1, in example implementations the RKG 100 includes multiple subgraphs including at least a first subgraph 150A and a second subgraph 150B. The respective subgraphs include "nodes" and "edges" and represent corresponding datasets that pertain to the domain(s) of interest. Each of the subgraphs 150A and 150B is linked to a canonical layer 120 (also referred to herein as a "linking layer" or "semantic layer") of the RKG 100. Although only two subgraphs 150A and 150B are illustrated in FIG. 1 to facilitate an explanation of salient concepts pertaining to the RKG 100, it should be appreciated that other examples of RKGs pursuant to the various concepts disclosed herein may include more than two subgraphs linked to the canonical layer 120 (and in many instances significantly more than two subgraphs linked to the canonical layer 120). As discussed in greater detail below, the canonical layer 120 of the RKG 100 generally serves to strategically interconnect and unify information in the underlying datasets represented by the respective subgraphs 150A and 150B of the RKG 100 to provide broader context for the information and facilitate querying and discovery of relationships in the information; in some instances, such relationships may otherwise not be apparent (even to experts in the domain(s) to which the RKG pertains) and/or too complex for human cognition.

Subgraphs Representing Datasets

In general, each of the subgraphs 150A and 150B of the RKG 100 shown in FIG. 1 is a graph representation of a corresponding "dataset" from a particular source, according to a "graph schema." In one aspect, each dataset includes some amount of "structured data," i.e., multiple data elements that can be meaningfully aggregated and that generally are organized as a formatted repository of data elements. In view of the foregoing, a given dataset often includes one or more files representing one or more spreadsheets or database tables with rows and columns, wherein at least some of the rows and or columns include structured data (and wherein the spreadsheets and/or tables also may include row and/or column headers denoting a thing to which the structured data pertains).

A given dataset generally includes information relating to one or more "entities" (things) having particular "entity types" (categories or labels for entities sharing at least one common aspect) that pertain to the domain(s) of interest for which the RKG 100 is constructed and maintained. As shown in FIG. 1, using the health care domain for purposes of illustration, the first subgraph 150A of the example RKG 100 represents a first dataset including information relating to the entity type "diseases" and includes representations of the disease entities "Disease 1," "Disease 2," and "Disease 3" according to a first graph schema. The second subgraph 150B represents a second dataset including information relating to the entity type "drugs" and includes representations of the drug entities "Drug 1" and "Drug 2" according to a second graph schema.

More specifically, in the example RKG 100 of FIG. 1, each of the subgraphs 150A and 150B (as well as the canonical layer 120) includes multiple "nodes" represented as labeled circles (e.g., one node in the first subgraph 150A with the label "Disease 2" is shown as node 152A, and one node in the second subgraph 150B with the label "Drug 2" is shown as node 152B). Additionally, at least the first subgraph 150A of the RKG 100 also includes multiple edges, wherein each edge is represented as a labeled arrow between two nodes (e.g., one edge in the first subgraph 150A with the label "HAS_DESCENDENT" is shown as edge 154A). Thus, each node in the RKG 100 represents an entity having a particular entity type, each edge represents a relationship of a particular type between two entities, and a graph schema for a given subgraph specifies types for nodes and edges (e.g., corresponding to types of entities and relationships), and a particular arrangement of nodes and edges based on the entities and relationships represented in the corresponding dataset (consider an example in which, in the first subgraph 150A, "Disease 1" is cancer, "Disease 2" is lung cancer, and "Disease 3" is kidney cancer-so Disease 1 is a "parent" to both Disease 2 and Disease 3, thereby giving rise to the relationship "HAS_DESCENDENT").

Regarding nodes in the RKG 100, each node may have one or more "attributes" (i.e., an identifier, aspect, quality, or characteristic of an entity represented by the node). In example implementations, each node must have at least a primary identifier that is unique in the namespace for the dataset that includes the entity; the primary identifier for a node thus may be different from a name of the corresponding entity that the node represents. As with entities, nodes may be categorized according to different node types, and the node type may be included as an attribute of the node (or may serve as part of the definition for a certain class of nodes corresponding to a particular entity type). Additionally, the label for a node as it appears in a subgraph may be its primary identifier or another attribute associated with the node. For example, the node 152A in the first subgraph 150A (representing the entity "Disease 2" from the ICD10 dataset stored in the namespace "CMSICD10," discussed further below) may be defined as a member of the node type class "Disease," and have the unique primary identifier "DIS3265," a name attribute "Disease 2," and have the name attribute assigned as its label in a subgraph representation (as illustrated in FIG. 1). An example description of this node in pseudo-code may be as follows, in which A1, A2 and A3 denote respective attributes of the node:

A1-Node ID: "DIS3295"
A2-Type: "Disease"
A3-Name: "Disease 2"

Regarding edges in the RKG 100, edges may be similarly categorized according to different types (i.e., of relationships), and a given edge may be associated with a unique primary identifier and one or more attributes. In one aspect, a primary identifier for an edge may be denoted as a "triple" including the primary identifier of the from-node, a descriptor for the type of edge, and the primary identifier of the to-node. For example, the edge 154A in the first subgraph 150A shown in FIG. 1 may be denoted as "DIS2555, HAS_DESCENDENT, DIS3295," wherein "DIS2555" is the primary identifier for the node labeled as "Disease 1" and DIS3295 is the primary identifier for the node labeled as "Disease 2." In another aspect, one attribute of an edge may relate to a probability regarding the certainty of the relationship represented by the edge (e.g., a numerical value between 0 and 1, inclusive).

In FIG. 1, the respective datasets represented by the subgraphs 150A and 150B generally come from different sources and may be heterogeneous in nature (e.g., vary in data type and/or format). Accordingly, to facilitate data organization and provenance in the structure of the RKG 100, each of the subgraphs 150A and 150B may correspond to (and their underlying codification may be stored in) an isolated "namespace" in computer storage. In illustrative examples, a given namespace generally may be labeled in a manner that somehow identifies the source of the dataset.

For example, the first dataset represented in the first subgraph 150A of the example RKG 100 shown in FIG. 1 pertaining to diseases may be the International Classification of Diseases, 10th revision (ICD10) obtained from the Center for Medicare and Medicaid Services (CMS); accordingly, the first dataset (and the underlying codification for the first subgraph) may be logically stored in a first namespace 156A (e.g., labeled in the example of FIG. 1 as "CMSICD10"). Similarly, the second dataset represented in the second subgraph 150B pertaining to drugs may be the normalized naming system for generic and branded drugs referred to as RxNorm, obtained from the U.S. National Library of Medicine (NLM); accordingly, the second dataset (and the underlying codification for the second subgraph) may be logically stored in a second namespace 156B (e.g., labeled in the example of FIG. 1 as "RxNorm").

In view of the foregoing, in the discussion herein a given subgraph of the RKG 100 may be referred to in some instances by its corresponding namespace label (e.g., in the example of FIG. 1, "CMSICD10" for the first subgraph 150A, and "RxNorm" for the second subgraph 150B).

Additionally, a given entity type in a particular dataset, as well as a set of nodes having the same type in a corresponding subgraph, may be uniquely identified as a "namespaced entity type" using the hierarchical symbol or nomenclature "Namespace/Entity Type" (e.g., "CMSICD10/Diseases" or "RxNorm/Drugs"). Similarly, a given entity in a particular dataset, as well as a particular node representing that entity in a corresponding subgraph, may be uniquely identified using the hierarchical symbol or nomenclature "Namespace/Entity Type/Entity Identifier" (e.g., "CMSICD10/Diseases/Disease 3" or "RxNorm/Drugs/Drug 1").

Although the example of FIG. 1 illustrates two subgraphs representing datasets pertaining to the health care domain from two particular sources, it should be appreciated that a wide variety of sources may provide datasets pertaining to a wide range of different domains on which an RKG may be based; examples of such sources include, but are not limited to, business entities (public or private companies), academic institutions, research organizations, government agencies, non-profit organizations, news outlets, and individuals.

Additionally, in general, a dataset includes information relating to one or more entities having particular entity types (represented by nodes in a subgraph having particular node types corresponding to the entity types). Examples of different entity types that may be represented in a given dataset (and node types that may be included in a subgraph) include, but are not limited to, physical/tangible objects, places (geographical references), concepts, legal or professional constructs (e.g., companies, organizations, institutions, government agencies, groups and/or networks, and hierarchies within same), products and/or services and various specifications or other information relating to same, events, occupations or roles, professional and/or academic credentials or specialization, publications, financial information, demographic information, statistical information, health-related information (e.g., diagnoses, medical conditions, symptoms, medical research information), and ontologies. A dataset also may include information indicating certain "relationships" between multiple entities, i.e., a nexus between two entities of the same type or different types (represented in a subgraph by an edge/labeled arrow between two nodes). A given dataset may also include information relating to one or more attributes of a given entity or a particular relationship between multiple entities (e.g., an aspect, quality, or characteristic of an entity or a relationship).

In connection with the health care domain, although the datasets represented by the subgraphs 150A and 150B shown in FIG. 1 respectively relate to diseases and drugs for purposes of illustration, it should be appreciated that a wide variety of datasets pertaining in some fashion to the health care domain may be represented in the RKG 100. Examples of such datasets include, but are not limited to, public health statistics and databases, adverse event databases, regulatory documents, insurance company policy documents, electronic medical records, patient surveys, insurance claims, Medical Science Liaison (MSL) notes, Medical Information Requests (MIRs), and medical ontologies obtained from various sources (e.g., the Unified Medical Language System from the U.S. National Library of Medicine, RxNorm, SNOMED CT (Systemized Nomenclature of Medicine), SNOP (Systemized Nomenclature of Pathology), the GALEN Common Reference Model, the National Drug Data File (NDDF), the International Statistical Classification of Diseases and Related Health Problems (ICD10), Chemical Entities of Biological Interest (ChEBI), Current Procedural Terminology (CPT), the Anatomical Therapeutic Chemical (ATC) classification system including Defined Daily Doses (DDD), the International Classification of Functioning, Disability and Health (ICF), LOINC, and the Medical Dictionary for Regulatory Activities (MedDRA)).

Canonical Layer

In the example RKG 100 shown in FIG. 1, the canonical layer 120 (also referred to as a "semantic layer" or a "linking layer") includes a set of linking nodes 122A, 122B, 122C, 124A and 124B (also referred to as "canonical nodes") of predetermined node types ("canonical node types") logically stored in a separate namespace 126 of computer storage for the RKG (e.g., the namespace 126 is labeled in the example of FIG. 1 as "roam"). The canonical nodes in the canonical layer 120 are connected via linking edges to corresponding (or closely corresponding) nodes in the subgraphs 150A and 150B in respective isolated namespaces of the RKG 100.

In one aspect of an RKG according to the concepts disclosed herein, the canonical layer of an RKG is the only means by which multiple subgraphs of the RKG are interconnected. Stated differently, there is no direct connection via an edge between any node in one subgraph and any node in another subgraph; rather, all edges from a given subgraph in an isolated namespace of an RKG connect that subgraph only to the canonical layer of the RKG and not another subgraph. This aspect can be readily observed in the example of FIG. 1, in which there are no edges between any node in the first subgraph 150A in the namespace "CMSICD10" and any node in the second subgraph 150B in the namespace "RxNorm," and there are only edges between these subgraphs and the canonical layer 120 in the namespace "roam."

In various implementations of an RKG pursuant to the concepts disclosed herein, the canonical node types for the canonical nodes of the canonical layer of an RKG correspond to selected node types that: 1) are present in multiple subgraphs of the RKG, or present in one subgraph of the RKG and likely to appear in one or more other datasets pertaining to the information domain (that may be later added to the RKG as one or more new subgraphs); and 2) have some significance in the information domain(s) (e.g., ontology or ontologies) on which the RKG is based.

In general, for a given domain or domains on which an RKG may be based, canonical node types may be designated based at least in part on an initial analysis of the respective datasets in isolated namespaces to be joined by the canonical layer to assess the prevalence, and/or present or prospective significance in the domain(s), of certain entity types that appear in one or more of the datasets. For example, in an RKG based on multiple datasets relating to global economics, one entity type of prevalence and/or significance may be different countries present in the dataset; accordingly, one canonical node type may be "Country." Similarly, another canonical node type for an RKG based on multiple datasets relating to global economics may be "Currency Unit," another canonical node type may be "Reserve Chairperson," and another canonical node type may be "Exchange Rate." In some aspects, selection of canonical node types involves a strategic decision, based in part on knowledge of the domain(s) of interest, to choose entities that link multiple (and often otherwise isolated) datasets in meaningful ways to provide a broader context for the collection of information in the respective datasets. This linking of respective datasets via strategic selection of linking entities in turn facilitates identification of relationships in the collection of information that may otherwise not be apparent without the greater context provided by an RKG, and/or too complex for human cognition.

In view of the foregoing, examples of canonical node types for the health care domain include, but are not limited to: Disease (e.g., see the nodes 122A, 122B and 122C in the canonical layer 120 of FIG. 1), Drug (e.g., see the nodes 124A and 124B in the canonical layer 120 of FIG. 1), FDA device code, FDA device name, Geography (e.g., address, census region, city, country, county, geocoordinates, MSA code, state, zip code), Health Care Organization, Health Care Professional, Hospital, Manufacturer, Procedure, Industry Event, Time, and Specialty (e.g., specialization, classification, grouping). As noted above in connection with subgraphs, the respective canonical node types in an RKG may be uniquely identified using the hierarchical symbol or nomenclature "Canonical Layer Namespace/Canonical Node Type" (e.g., "roam/Disease" or "roam/Drug").

In the example RKG 100 of FIG. 1, two canonical node types (i.e., roam/Disease and roam/Drug) are present in the canonical layer 120, and these two node types exactly correspond to the different node types shown in the subgraphs 150A and 150B of the RKG 100. However, it should be appreciated that the canonical node types present in the canonical layer of an RKG according to the concepts disclosed herein need not necessarily include all of the node types present in the multiple subgraphs of the RKG (i.e., there may be some node types present in one or more subgraphs that do not have a corresponding canonical node type in the canonical layer of the RKG). Accordingly, unlike the example RKG 100 shown in FIG. 1, the canonical layer of another RKG may include (and generally does include) a quantity of canonical nodes that is less than (and sometimes significantly less than) the sum of all nodes present in the multiple subgraphs of the RKG. Additionally, there is no logical limit to the number of different canonical node types that may be selected for the canonical layer of an RKG (and corresponding number of canonical nodes themselves); again, as noted above, salient criteria for selecting canonical node types for the canonical layer is that they have some significance in the information domain(s) on which the RKG is based and are present in one or more subgraphs of the RKG. Regardless of its canonical node type, each canonical node is unique in the canonical layer (it is only found once in the canonical layer); stated differently, each canonical entity is represented uniquely by only one node in the canonical layer.

In the example RKG 100 shown in FIG. 1, a given canonical node in the canonical layer is identical to (e.g., a "clone" of, or deemed to be sufficiently related to) a corresponding subgraph node that appears in at least one subgraph of the RKG. Accordingly, the corresponding subgraph node is connected to the canonical node by an edge of the type "IS" (e.g., see the node 152A in the first subgraph 150A connected to the canonical node 122B in the canonical layer 120 via an arrow labeled as "IS"). More generally, for an RKG according to the concepts disclosed herein, each edge between a canonical node in the canonical layer and a corresponding node in one or more subgraphs of the RKG is one of the following types: "IS," "IS_PART_OF," or "CONTAINS" (or other terms designating substantially similar relationships, such as "INCLUDES," "IS_INCLUDED_IN," "ENCOMPASSES," "SUBSUMES," and the like). In some implementations, the direction of a labeled arrow denoting an edge between a node in one or more subgraphs and a canonical node may be toward the canonical node, as shown in FIG. 1; however, it should be appreciated that in other implementations the direction of a labeled arrow representing an edge may be from the canonical node to one or more subgraph nodes.

Although each of the canonical nodes in the canonical layer 120 of the example RKG 100 shown in FIG. 1 is connected to only one node in one subgraph of the RKG 100, these canonical nodes may nonetheless be of particular significance in the information domain such that they are expected to be connected to one or more new subgraph nodes at a future time (e.g., as one or more additional datasets pertaining to the information domain(s) are added to the RKG in corresponding new namespaces). In other implementations of an RKG, identical or closely related nodes to a given canonical node ("clone" nodes) appear in at least two subgraphs in different namespaces of the RKG; in this case, at least one canonical node in the canonical layer is connected via multiple edges to at least two corresponding nodes in respective subgraphs in different namespaces of the RKG (and in some implementations, most or all of the canonical nodes are connected to multiple subgraphs in this manner).

Figure 2:
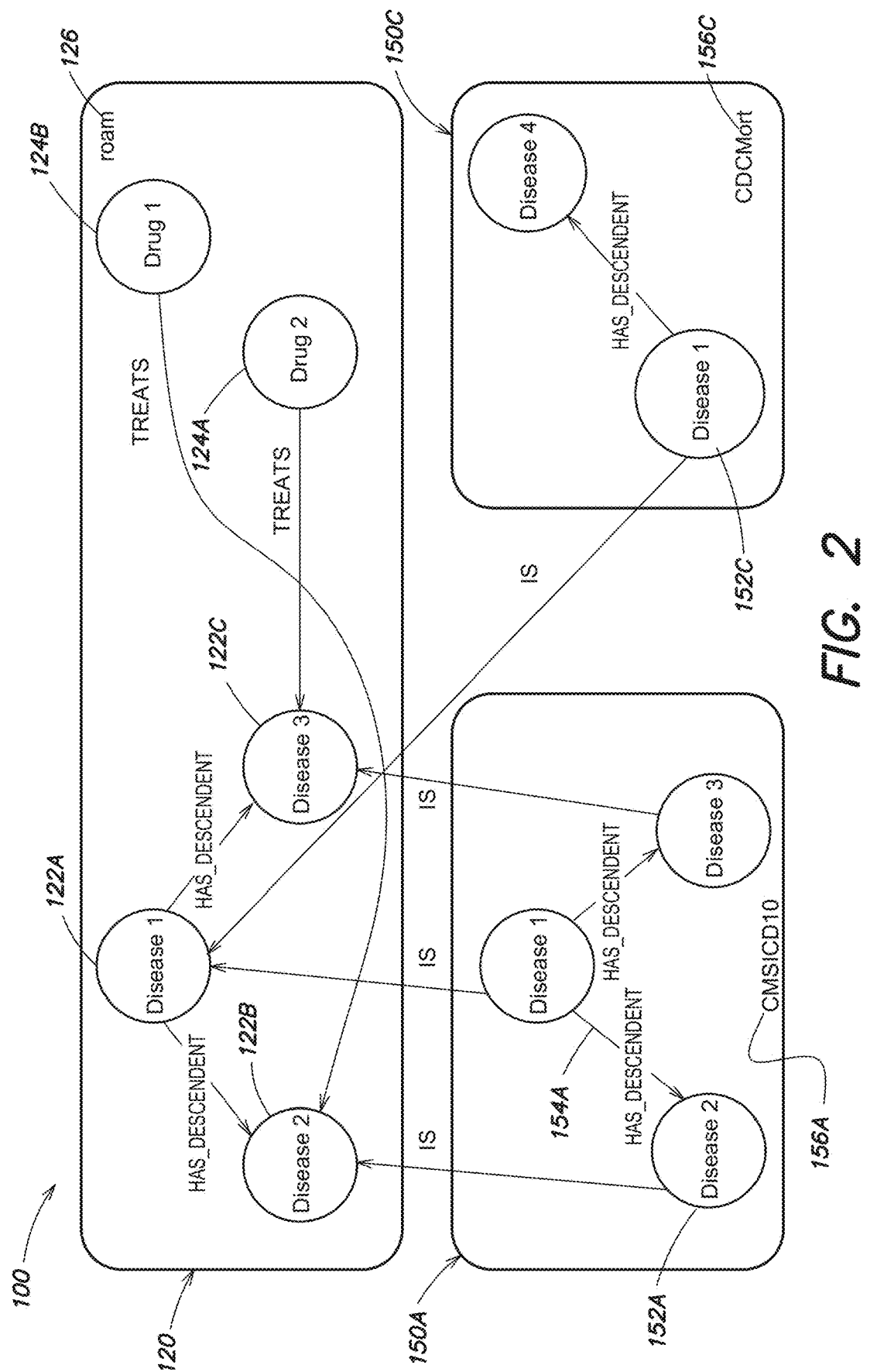
FIG. 2 illustrates the example RKG of FIG. 1 with an additional subgraph, according to one inventive implementation.

FIG. 2 illustrates the foregoing concept. FIG. 2 is based on the RKG 100 shown in FIG. 1, in which a new third subgraph 150C has been added to the RKG 100 (and the second subgraph 150B is not shown in FIG. 2 to facilitate clarity of the illustration). In FIG. 2, the third subgraph 150C represents a third dataset pertaining to underlying causes of death in the U.S. obtained from the U.S. Center for Disease Control, in which certain diseases appear as entities; accordingly, the third dataset (and the underlying codification for the third subgraph) is logically stored in a third namespace 156C (e.g., labeled in the example of FIG. 2 as "CDCMort"). The third subgraph 150C includes multiple nodes having a node type "Disease," such as the node 152C with the label "Disease 1." The node 152C corresponds to the canonical node 122A (also "Disease 1"-both nodes represent the same entity); accordingly, the canonical node 122A is not only connected via an "IS" edge (represented by an arrow labeled as "IS") to the node labeled as "Disease 1" in the first subgraph 150A, but it is also connected via an "IS" edge to the node 152C in the third subgraph 150C. In this manner, the canonical node 122A links the first subgraph 150A and the third subgraph 150C.

The example shown in FIG. 2 of the RKG 100 in which the canonical layer 120 links two (or more) subgraphs illustrates particular advantages of the canonical layer (and thus the RKG itself) in various implementations. For example, without the canonical layer, if one wanted to directly interconnect (with edges of the type "IS") respective nodes in different subgraphs representing (or deemed to represent) the same entity, one would need to rely on the conventional mathematical construct of a "combination" to determine the number of edges of the type "IS" that would be required to completely interconnect these nodes. More specifically, for a set of n nodes representing (or deemed to represent) the same entities in different subgraphs, the number of edges needed to directly and completely connect respective pairs of the n nodes between the different subgraphs is given by the binomial coefficient:

$$\binom{n}{k} = \frac{n!}{k!(n-k)!}$$

where k=2, and where the binomial coefficient is often colloquially referred to as "n choose k" (or, in the present example, "n choose 2"). In the example of FIG. 2 in which there are only two subgraphs and hence only two nodes to connect (n=2), without the canonical layer only one edge would be required to connect the two corresponding nodes. However, considering an example in which there are ten different subgraphs each containing the node "Disease 1," according to the binomial coefficient above 45 edges would be required to pairwise interconnect these nodes directly (10 choose 2=45).

With the foregoing in mind, using the canonical layer 120 containing the canonical node "Disease 1" to provide a linking node for the ten subgraphs in the example above, only ten edges would be required to fully interconnect each of the "Disease 1" nodes in the ten different subgraphs to the canonical node "Disease 1" in the canonical layer 120 (i.e., one edge per subgraph). In this manner, the canonical layer provides for a substantial reduction of graph complexity (e.g., number of edges) required to interconnect respective corresponding nodes in different subgraphs. This in turn offers distinct advantages as the number of subgraphs (and the number of corresponding nodes in different subgraphs) increases for the particular domain(s) of interest; examples of such advantages include, but are not limited to, reductions in data storage and retrieval times, enhanced query/search efficacy and discovery of relationships in different parts of the RKG, enhanced ability to infer relationships in different parts of the RKG, and enhanced ability to train data models for natural language processing (NLP) and other purposes (e.g., using machine learning techniques) based on information extracted from the RKG.

Within the canonical layer of an RKG, a given canonical node may be connected to one or more other canonical nodes via respective edges of a wide variety of types, based at least in part on the diverse relationships that may exist between canonical nodes of the same type or different types. For example, as shown in FIG. 1, the canonical node 124A ("Drug 2") is connected via an edge of the type "TREATS" to the canonical node 122C ("Disease 3"); similarly, the canonical node 124B ("Drug 1") is connected via an edge of the type "TREATS" to the canonical node 122B ("Disease 2").

More generally, as discussed in greater detail below, edges between subgraph nodes and canonical nodes, or between any two canonical nodes, may be generated based at least in part on: 1) one or more particular attributes of the respective nodes, 2) relationships between entities specified in some manner by the underlying information in the datasets represented by the subgraphs of the RKG, and/or 3) trained models that predict (based on a variety of criteria coded in logic for the model) that the nodes should be connected as having some particular type of articulated relationship (with some corresponding probability).

For example, edges may be generated between subgraph nodes and canonical nodes of certain types (or between two canonical nodes) pursuant to defined logic based on a variety of criteria (e.g., connect subgraph node of type X to canonical node of type X with an edge of type "IS" if the respective primary identifiers of the nodes match; connect subgraph node of type Y to canonical node of type Y with an edge of type "IS" if respective attributes A1, A3 and A5 have the same values for the respective nodes).

In other instances, an edge may be generated between a subgraph node and a canonical node, or between two canonical nodes, based on a trained model (also referred to herein further below as a "model-based connector") that predicts in some respect the relationship between the nodes. More specifically, a trained model may be codified to connect subgraph node A of type X to canonical node B of type X with an edge of type "IS" if the model predicts (based on a variety of criteria coded in the logic for the model) that these nodes should be connected with some degree of certainty (e.g., if at least one of respective attributes A1, A2 and A3 for each node is substantially similar, with some certainty), wherein the degree of certainty may be recorded as a probability attribute of the edge of type "IS" (e.g., using a number from 0 to 1, inclusive). Consider an example in which a canonical node A for a node type "Professional Practitioner" has the attributes {A1-First Name: "Erunia," A2-Last Name: "Agbekele," A3-Profession: "Biologist"}, and a subgraph node B of the same node type includes the attributes {A1-First Name: "E.," A2-Last Name: "Agbekle," A3-Profession: "Biol"}. A model-based connector (trained model) evaluating these nodes may be codified to generate an edge of type "IS" between these two nodes, with some appreciable certainty (e.g., the edge type "IS" may have a probability attribute of .93 pursuant to certain parameters of the model), even though none of the respective attributes is identical for the respective nodes.

In various instantiations, the RKG 100 illustrated in FIG. 1 may be created and maintained using a graph database management system, examples of which include, but are not limited to, Amazon Neptune, Neo4j, Open Link Virtuoso, and OrientDB. The RKG may be represented in a variety of graph-specific file formats, examples of which include, but are not limited to, GraphML, DOT (used by the program Graphvix), RDF (Resource Description Framework), OWL, and GML. The RKG also may be represented in more general file formats such as CSV, JSON and XML. In general, suitable file formats and database management systems for an RKG pursuant to the concepts disclosed herein allow for 1) various node types, 2) various edge types, 3) directed edges, 4) node and edge attributes having at least the types "string," "integer," "float," and lists thereof, and 5) multiple edges between pairs of nodes.

Building a Roam Knowledge Graph (RKG)

Having discussed above the general structure of an RKG pursuant to the inventive concepts herein, the disclosure now turns to inventive methods for building an RKG.

As an initial matter, the information domain(s) for which an RKG is desired is/are first specified, such that multiple datasets from one or more sources may be preliminarily identified that are available and germane to the domain(s) of interest. In one aspect, there is theoretically no limit on the number of datasets that may be considered in the first instance for an RKG (any such limitations may arise, based in at least in part, on the particular graph-specific file format and/or graph database management system employed to create and maintain an RKG). As a general premise, an RKG has notable utility in providing links between two or more datasets, particularly when one or more of the datasets includes dynamic information (e.g., where regular data updates and/or data growth are important) and when the datasets are heterogeneous and arriving from diverse sources.

As noted above, in one aspect, each dataset includes some amount of "structured data" (i.e., multiple data elements that can be meaningfully aggregated and that generally are organized as a formatted repository of data elements) or "semi-structured data" (e.g., having some organizational structure). In particular, a given dataset often includes one or more files, representing one or more spreadsheets or database tables with rows and columns, wherein at least some of the rows and or columns include structured data (and wherein the spreadsheets and/or tables also may include row and/or column headers denoting one or more entity types to which the structured data pertains). In some implementations discussed further below, some datasets or files that may be germane to the domain(s) of interest (and hence are suitable candidates for inclusion in an RKG) may contain significant amounts of "unstructured data" (e.g., free-form text). To facilitate inclusion in an RKG of information contained in unstructured data, datasets or files containing such unstructured data may be pre-processed (e.g., according to various machine learning or natural language processing techniques, as discussed further below) to provide at least some structured or semi-structured data in the datasets/files, such that these datasets would be suitable for the inventive graph-building methods discussed herein.

In a given implementation of an RKG, one or more datasets may be obtained from various sources of public information (e.g., government agencies, regulatory bodies, academic or professional institutions or consortia, private companies that maintain public databases, etc.) relating to a given domain or related domains. In some instances, one or more datasets under consideration may be deemed to be a "fundamental dataset" (also referred to herein as a "golden dataset"), i.e., a dataset of factual information from a trusted (and often public) source. In some implementations, one or more such fundamental datasets may be instructive, at least in part, toward the preliminary selection of canonical node types for the canonical layer of an RKG (given the particular entities included in the fundamental dataset(s) and the other information in the dataset(s) pertaining to these entities). In connection with the health care domain, examples of fundamental datasets include, but are not limited to, a list of United States zip codes obtained from the U.S. Postal Service, and National Provider Identifier (NPI) records of health care practitioners obtained from the National Plan and Provider Enumeration System (NPPES) of the U.S. Department of Health and Human Services. In some implementations of an RKG pursuant to the present disclosure, several (if not a majority or in some cases all) of the datasets on which the RKG is based may be fundamental or golden datasets.

Selection of Canonical Node Types

In general, for a given domain or domains on which an RKG may be based, in example implementations canonical node types for the canonical layer may be designated based at least in part on an initial analysis of the respective datasets in isolated namespaces to be joined by the canonical layer (and particularly fundamental datasets) to assess the prevalence, and/or present or prospective significance in the domain(s), of certain entity types that appear in one or more of the datasets. For example, in an RKG based on multiple datasets relating to the domain of "global economics," one entity type of prevalence and/or significance in multiple datasets may be different countries present in the datasets; accordingly, one canonical node type in an RKG pertaining to global economics may be "Country." Similarly, based on other entities present and of some significance in the multiple datasets, another canonical node type for an RKG relating to global economics may be "Currency Unit," another canonical node type may be "Reserve Chairperson," and another canonical node type may be "Exchange Rate."

As noted above, in some aspects selection of canonical node types involves a strategic decision, based in part on knowledge of the domain(s) of interest, to choose entities of certain types that link multiple (and often otherwise isolated) datasets in meaningful ways to provide a broader context for the collection of information in the respective datasets. This linking of respective datasets via strategic selection of linking entity types corresponding to canonical node types in the canonical layer of an RKG in turn facilitates identification, via the RKG once built, of relationships in the collection of information that may otherwise not be apparent without the greater context provided by the RKG and its inventive structure, and/or too complex for human cognition.

With reference again to the example RKG 100 shown in FIGS. 1 and 2 and the canonical layer 120 in the namespace "roam," two canonical node types are shown generally relating to the health care domain (i.e., "Disease" and "Drug"). Based on the foregoing discussion regarding the designation of canonical node types in a given domain, and in particular consideration of the health care domain, examples of canonical node types derived from an analysis of a variety of public datasets from different sources relating to the health care domain on which an RKG similar to the RKG 100 may be based, include, but are not limited to:

roam/Disease
roam/Drug
roam/FDADeviceCode
roam/FDADeviceName
roam/Geography
roam/HealthCareOrganization
roam/HealthCareProfessional
roam/Hospital
roam/Manufacturer
roam/Procedure
roam/IndustryEvent
roam/Time
roam/Specialty In another aspect, it should be appreciated that the canonical node types in the canonical layer of an RKG may change over time. For example, as one or more of the initial datasets on which an RKG is based are updated and/or evolve over time, and/or as one or more new datasets are identified (and stored in one or more new isolated namespaces) to be represented as subgraphs and connected to the canonical layer of an RKG, new entity types in the datasets may be identified as appropriate candidates for augmenting the canonical layer with additional canonical node types (e.g., based on various criteria similar to those discussed above).

Ingesting and "Cleaning" a Dataset

Figure 3:
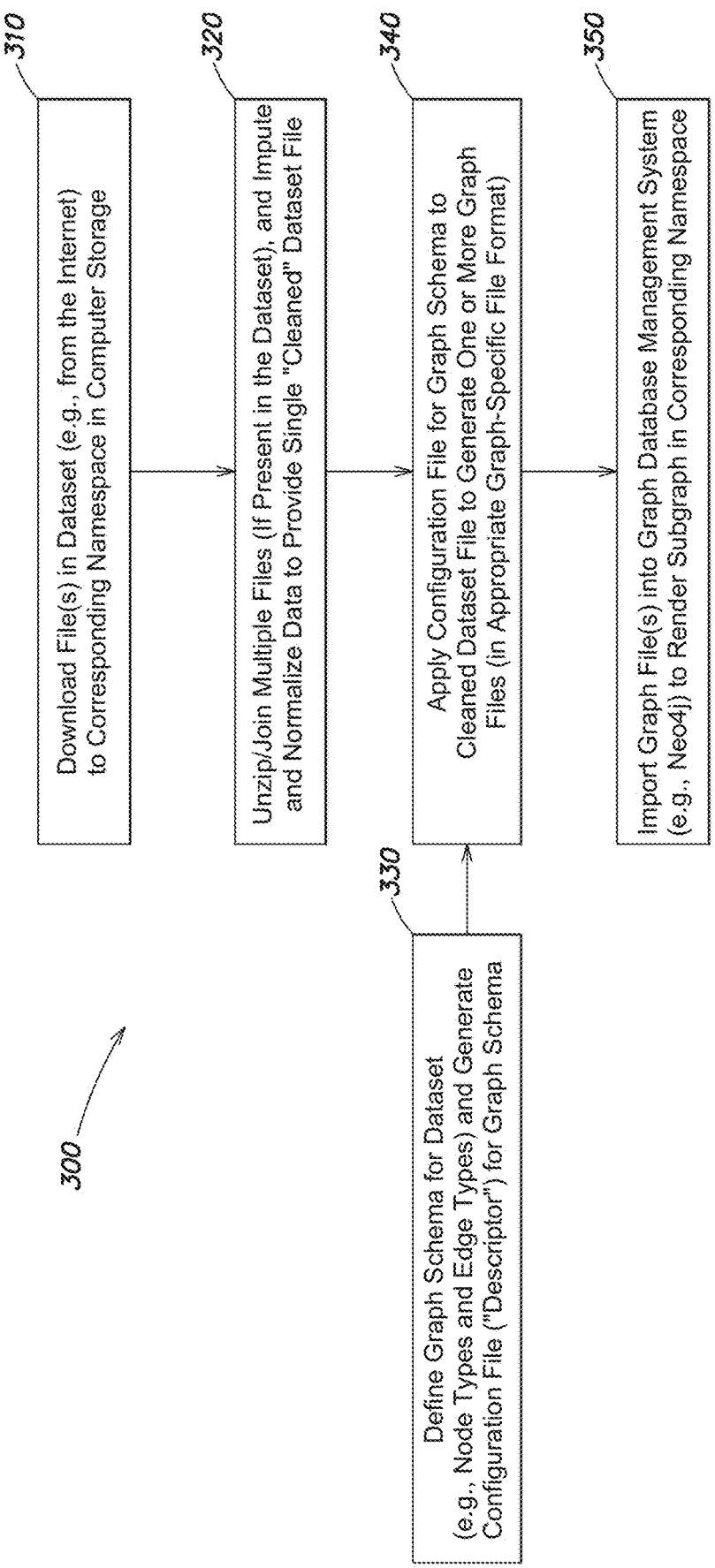
FIG. 3 illustrates an example method for ingesting datasets and generating subgraphs representing the datasets for the RKG of FIG. 1, according to inventive implementations.

Available datasets pertaining to the domain(s) of interest may be respectively downloaded (e.g., from the Internet) and imported into corresponding isolated namespaces of computer storage (which namespaces may be labeled, based at least in part, on the source of the dataset). Thereafter, a given dataset may be processed so as to generate a subgraph representing the dataset. FIG. 3 illustrates an example method 300 for ingesting a given dataset and generating a subgraph representing the dataset, according to inventive implementations. In the discussion that follows, it should be appreciated that the method 300 outlined in FIG. 3 may be applied, in whole or in part, in a parallel or serial fashion to ingest multiple datasets and generate corresponding subgraphs representing the datasets. For example, with reference again to the RKG 100 of FIG. 1, the method 300 may be applied to each of the two datasets in the respective namespaces "CMSICD10" and "RxNorm" (e.g., sequentially or contemporaneously) to generate the corresponding subgraphs 150A and 150B of the RKG 100.

In block 310 of FIG. 3, a given dataset may include one or more files that are downloaded to a corresponding namespace in computer storage. For example, one or more files in a dataset may be downloaded via the Internet from a website that provides a portal to an Internet-coupled server or servers maintained by (or providing hosting services to) the source of the dataset. In one example implementation, the method employs conventional techniques to crawl the Internet and download the one or more files relating to the dataset. In some instances, multiple files for a given dataset are obtained from the source as zipped files, and/or the file(s) may be in a particular file format or different file formats (e.g., .csv, .json).

In block 320 of FIG. 3, if the dataset includes related information spread across multiple files, and the files may be zipped, the files for the dataset are unzipped if necessary and joined (e.g., in the sense of a relational database) to create a single file for the dataset (e.g., a single .csv file). Missing values in the data that are known or readily obvious may be imputed (filled in) in a basic sense to generally maintain the integrity of the data in the dataset (e.g., if it is known that a zip file from a particular source includes one file per country, a "country" value can be entered into an appropriate field of the single file representing the joined and unzipped separate files of the ingested dataset). In some implementations, as part of block 320, at least some of the data in the single file representing the dataset may be "normalized" (or "canonicalized"), i.e., modified in some respect according to a predetermined standard or format so it may be more readily compared to other pieces of data (e.g., in other datasets) relating to the same or similar thing. This process in block 320 of joining, imputing and/or normalizing may be generally referred to herein as "cleaning," such that a single "cleaned" dataset file is generated in block 320 based on the originally-ingested dataset.

Building a Subgraph

In block 330 of the method 300 shown in FIG. 3, a "graph schema" is created for the dataset to define the node types and the edge types that are used in the subgraph to represent the dataset. In one aspect, the definition of node types and edge types in the graph schema for a given dataset may be based at least in part on the specification of canonical node types for the canonical layer of an RKG. This ensures that at least one of the node types defined in the graph schema for the dataset corresponds to an identical (or substantially similar) canonical node type in the canonical layer of the RKG, to thereby facilitate connection of the subgraph representing the dataset, via an edge of the type "IS" or similar type, to the canonical layer of the RKG, as discussed further below.

The graph schema for a given dataset may be encoded in various manners (e.g., using a suitable coding language and/or file format) to generate a configuration file (also referred to herein as a "descriptor file") defining the graph schema. For example, provided below is an excerpt of a descriptor file, using the Python programming language, to define a graph schema for generating a subgraph for the National Provider Identifier (NPI) dataset, obtained from the National Plan and Provider Enumeration System (NPPES) of the U.S. Department of Health and Human Services and ingested into a namespace "NPI" in computer storage. Although an NPI dataset is not represented in the example RKG 100 shown in FIGS. 1 and 2, the graph schema defined by the code reproduced immediately below for the NPI dataset illustrates a number of relevant concepts generally applicable to graph schema for subgraphs of an RKG (including the relatively simpler graph schema employed to generate the subgraphs 150A, 150B and 150C shown in FIGS. 1 and 2).

In particular, in creating the example graph schema for the NPI dataset, the descriptor file below defines the node types "Provider," "Address," "Specialization," "Credentials," "AuthorizedOfficial," and "State." For each of these node types, the descriptor file also defines one or more attributes of the node type. Given these node types, the descriptor file for the graph schema also defines edge types between particular pairs of node types as follows (using the "triple" format):

Authorized Official, REPRESENTS, Provider
Provider, HAS_CREDENTIALS, Credentials
AuthorizedOfficial, HAS_CREDENTIALS, Credentials
Provider, MAILING ADDRESS, Address
Provider, PRACTICE LOCATION, Address
Provider, SPECIALIZES_IN, Specialization
Provider, LICENSED_IN, State The code excerpt for this descriptor file, in the Python programming language, is as follows:

```python
namespace = Namespace('NPI')
# Provider
provider_abstract_node = AbstractNode(namespace, 'Provider')
provider_attr_keys = {
'entity_type',
'is_organization_subpart',
'is_sole_proprietor',
'last_updated_date',
'npi_deactivation_date',
'npi_reactivation_date',
'parent_organization_lbn',
'replacement_npi',
'NPI',
'organization_name',
'name_suffix',
'name_prefix',
'first_name',
'middle_name',
'last_name',
'gender.code',
'gender.value',
'credential',
'enumeration_date'}
provider_abstract_node.make_abstract_attributes(*provider_attr_keys)
provider_identifier = NodeIdentifier(
    provider_abstract_node,
    provider_abstract_node.get_abstract_attribute('NPI'),
    make_permanent_copy=False)
# Address (provider mailing address and provider practice location)
address_abstract_node = AbstractNode(namespace, 'Address')
address_attr_keys = {
'first_line',
'second_line',
'city_name',
'telephone_no',
'state_code',
'postal_code',
'country_code',
'fax_no',
'telephone_no',
'concatenated_address'}
address_abstract_node.make_abstract_attributes(*address_attr_keys)
address_identifier = NodeIdentifier(
    address_abstract_node,
    address_abstract_node.get_abstract_attribute('concatenated_address'),
    make_permanent_copy=False)
# Specialization
specialization_abstract_node = AbstractNode(namespace, 'Specialization')
specialization_abstract_node.make_abstract_attribute('taxonomy_code')
specialization_identifier = NodeIdentifier(
    specialization_abstract_node,
    specialization_abstract_node.get_abstract_attribute('taxonomy_code'),
    make_permanent_copy=False)
# Credentials
credential_abstract_node = AbstractNode(namespace, 'Credential')
credential_abstract_node.make_abstract_attributes('credential')
credential_identifier = NodeIdentifier(
    credential_abstract_node,
    credential_abstract_node.get_abstract_attribute('credential'),
    make_permanent_copy=False)
# Authorized official:
official_abstract_node = AbstractNode(namespace, 'AuthorizedOfficial')
official_attr_keys = {
'credential',
'first_name',
'middle_name',
'last_name',
'name_prefix',
'name_suffix',
'telephone_no'}
official_abstract_node.make_abstract_attributes(*official_attr_keys)
# AuthorizedOfficial-[:REPRESENTS]->Provider
official_provider_abstract_edge = AbstractEdge(
```

```
    official_abstract_node,
    provider_abstract_node,
    relation_type='REPRESENTS')
official_provider_abstract_edge.make_abstract_attribute('title_or_position')
official_provider_subgraph = AbstractSubgraph(
    provider_abstract_node, official_abstract_node,
    official_provider_abstract_edge)
official_identifier = NodeIdentifier(
    official_abstract_node,
    CombineFieldsTransformer(
    provider_abstract_node.get_abstract_attribute('NPI'),
    official_abstract_node.get_abstract_attribute('first name'),
    official_abstract_node.get_abstract_attribute('last name')),
make_permanent_copy=False,
subgraph=official_provider_subgraph)
# State
state_abstract_node = AbstractNode(namespace, 'USState')
state_abstract_node.make_abstract_attribute('code')
state_identifier = NodeIdentifier(
    state_abstract_node,
    state_abstract_node.get_abstract_attribute('code'),
    make_permanent_copy=False)
# Edges:
# Provider-[:HAS_CREDENTIALS]-> Credential
provider_credential_abstract_edge = AbstractEdge(
provider_abstract_node,
credential_abstract_node,
relation_type='HAS_CREDENTIALS')
# AuthorizedOfficial-[:HAS CREDENTIALS]-> Credential
official_credential_abstract_edge = AbstractEdge(
    official_abstract_node,
    credential_abstract_node,
    relation_type='HAS_CREDENTIALS')
# Provider-[:MAILING_ADDRESS1-> Address
provider_mailing_address_abstract_edge = AbstractEdge(
    provider_abstract_node,
    address_abstract_node,
    relation_type='MAILING_ADDRESS')
# Provider-[:PRACTICE_LOCATION]-> Address
provider_practice_address_abstract_edge = AbstractEdge(
    provider_abstract_node,
    address_abstract_node,
    relation_type='PRACTICE_LOCATION')
# Provider-[:SPECIALIZES_IN]-> Specialization
provider_specialization_abstract_edge = AbstractEdge(
    provider_abstract_node,
    specialization_abstract_node,
    relation_type='SPECIALIZES_IN')
provider_specialization_abstract_edge.make_abstract_attribute('specialty_rank
ing')
# Provider-[:LICENSED_IN]->State
provider_state_abstract_edge = AbstractEdge(
    provider_abstract_node,
    state_abstract_node,
    relation_type='LICENSED_IN')
provider_state_abstract_edge.make_ abstract_attribute('license_ranking')
```

Figure 4:
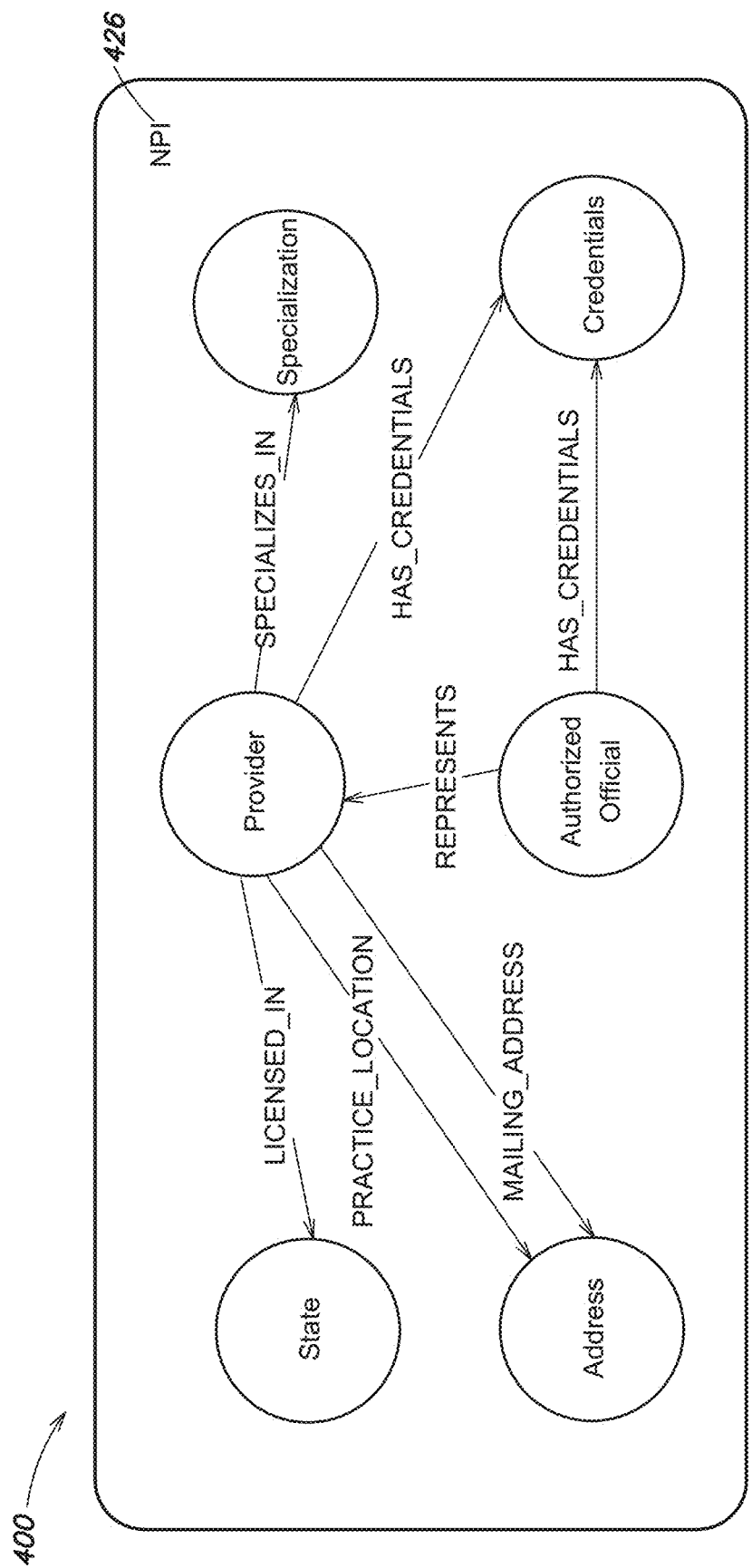
FIG. 4 illustrates an example graph schema for generating a subgraph representing an example public dataset, according to one inventive implementation.

FIG. 4 illustrates an example graph schema 400, defined by the above descriptor file, for generating a subgraph representing the NPI public dataset in the NPI namespace 426, according to one inventive implementation. It should be appreciated that FIG. 4 itself is not a subgraph of actual nodes and edges (e.g., as shown in FIGS. 1 and 2) representing the NPI dataset; rather, the graph schema 400 illustrates node types, edge types, and the particular placement of certain edge types between certain node types. Accordingly, in FIG. 4, the labeled circles do not represent nodes themselves, but rather node types; similarly, the labeled arrows do not represent edges themselves, but rather edge types. The actual subgraph for the NPI dataset is generated by applying the graph schema shown in FIG. 4 to a "cleaned" single file for the NPI dataset. Accordingly, there may be multiple nodes of each of the node types shown in FIG. 4 in a subgraph for the NPI dataset (and, correspondingly, multiple edges of each of the edge types shown in FIG. 4.

More generally, with reference again to FIG. 3, in block 340 a configuration file (or descriptor file) that defines a graph schema for a given dataset is applied to the cleaned single file for the dataset to generate one or more graph files (in an appropriate graph-specific file format). In block 350 of FIG. 3, these one or more graph files are in turn imported into a graph database management system to render the subgraph representing the dataset in the corresponding namespace. In one example implementation, with reference again to the subgraph 150A shown in FIG. 1, the one or more graph files generated by applying the graph schema to the cleaned single file for a given dataset include a "*_nodes .csv" file for each node type (e.g., for the CMSICD10 dataset, a file "disease_nodes .csv" would be generated) and a "*_edges .csv" file for each edge type (e.g., for the CMSICD data set, a file "disease_to_disease.edges .csv" would be generated). These .csv files may be imported, for example, into the Neo4j graph database management system (or another graph database management system) to render the subgraph representing the dataset.

The method 300 shown in FIG. 3 may be similarly implemented to ingest multiple datasets and generate corresponding subgraphs to be included in an RKG according to the inventive concepts disclosed herein. In some implementations, for a given dataset, the blocks 310 and 320 in FIG. 3 may be performed periodically (e.g., once a week, once a month), based at least in part on the dynamic nature of the dataset. Likewise, the blocks 340 and 350 in FIG. 3 may be performed periodically (in some cases with the same periodicity as performing blocks 310 and 320, but not necessarily with the same periodicity as performing the blocks 310 and 320).

Figure 5:
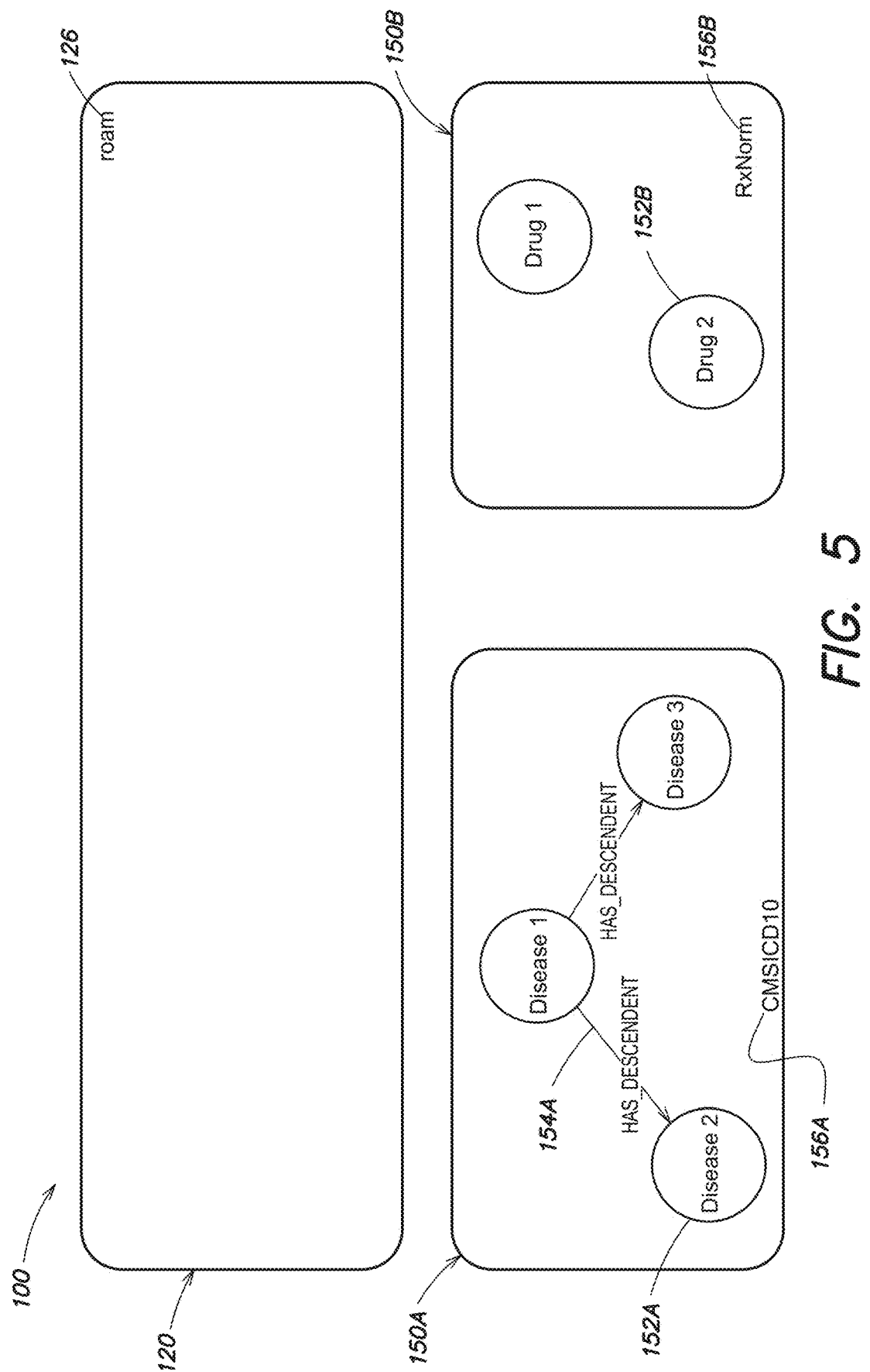
FIG. 5 illustrates the state of graph-building for the example RKG shown in FIG. 1, after the method of FIG. 3 has been applied to two datasets to generate corresponding subgraphs of the RKG, according to one inventive implementation.

Populating the Canonical Layer with Canonical Nodes and Connecting Subgraphs to the Canonical Layer FIG. 5 illustrates the state of graph-building for the RKG 100 shown in FIG. 1, after the method of FIG. 3 has been applied to the CMSICD10 dataset and the RxNorm dataset. In particular, in FIG. 5, each of the subgraphs 150A and 150B is fully rendered in a corresponding isolated namespace, but the canonical layer 120 is not yet populated and the subgraphs are not yet connected to the canonical layer. Once subgraphs are generated for respective datasets in isolated namespaces of an RKG, the next phases of graph-building involve populating the canonical layer of the RKG with canonical nodes and connecting the subgraphs to the canonical layer.

Figure 6:
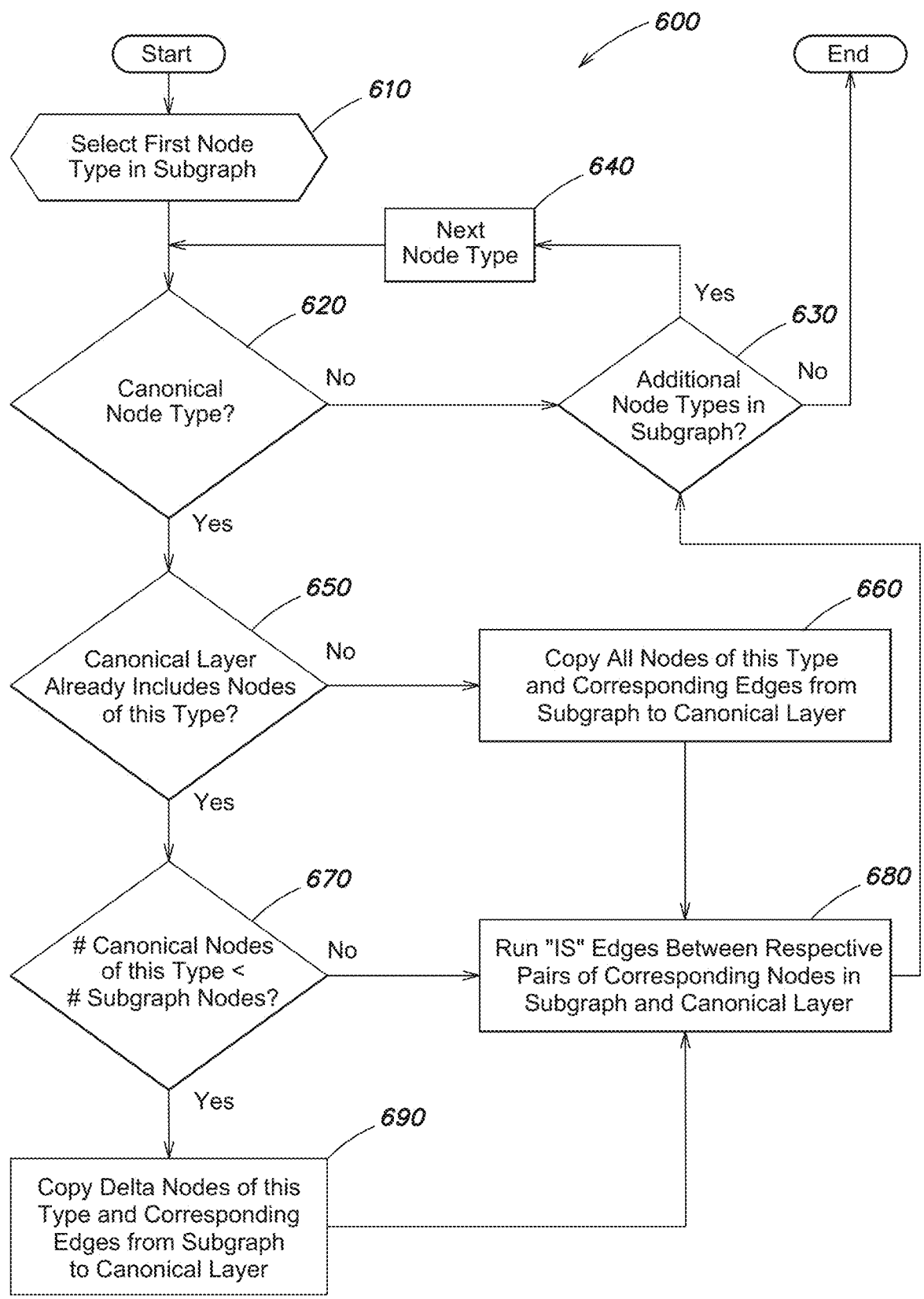
FIG. 6 illustrates an example method for populating a canonical layer of an RKG with canonical nodes and connecting subgraphs of the RKG to the canonical layer, according to one inventive implementation.

FIG. 6 illustrates such a method for populating the canonical layer of the RKG with canonical nodes that are copied from a subgraph representing a dataset and connecting corresponding nodes of the subgraph and the canonical layer with edges of the type "IS" (or edges of substantially similar types to "IS," as discussed above). It should be appreciated that the method of FIG. 6 is performed on a subgraph-by-subgraph basis and may be performed sequentially on a number of subgraphs in succession or contemporaneously on multiple subgraphs.

In block 610 of FIG. 6, a first node type is selected in the subgraph under consideration; in some implementations this selection may be made arbitrarily. If this first node type is not a canonical node type, as illustrated in blocks 620, 630 and 640 the method then proceeds to the next node type in the subgraph; if there are no more node types remaining for consideration, the method ends. If however the node type presently under consideration is a canonical node type, in block 650 of FIG. 6 the method considers if there are already nodes of this type in the canonical layer of the RKG. If not, in block 660 all of the nodes of this type and any edges coupled to these nodes are copied from the subgraph into the canonical layer, and in block 680 edges of the type "IS" are run between respective pairs of corresponding nodes in the canonical layer and the subgraph. If in block 650 it is determined that there are already canonical nodes of the type in question in the canonical layer, in block 670 the method considers if the number of canonical nodes of this type already present in the canonical layer is less than the number of subgraph nodes of this type. If not (i.e., if the set of canonical nodes of the type in question is a superset of the subgraph nodes of the same type), the method proceeds to block 680 and runs edges of the type "IS" between respective pairs of corresponding nodes in the canonical layer and the subgraph.

In block 670 of FIG. 6, if the number of canonical nodes of the type in question is less than the number of subgraph nodes of the same type (the set of subgraph nodes of the type in question is a superset of the canonical nodes of this type), then in block 690 those subgraph nodes of the type in question that are not already in the canonical layer ("delta nodes"), as well as any edges connected to these nodes, are copied into the canonical layer as canonical nodes and edges. In an alternative implementation of block 690, the entire set of subgraph nodes of the type in question (and their corresponding edges) may be copied into the canonical layer and thereby replace any preexisting canonical nodes of this type. Additionally, in some implementations, the dataset represented by the subgraph under consideration may be particularly identified as a fundamental dataset for this node type (and may replace another previously-designated fundamental dataset for this node type). The method 600 then proceeds to block 680 where, as noted above, edges of the type "IS" are run between respective pairs of corresponding nodes in the canonical layer and the subgraph. Once edges of the type "IS" are run between the corresponding nodes of the type in question, the method proceeds to block 630 to see if there are any remaining node types in the subgraph to consider for possible addition to the canonical layer. The method ends when all node types in the subgraph have been thusly considered.

Figure 7:
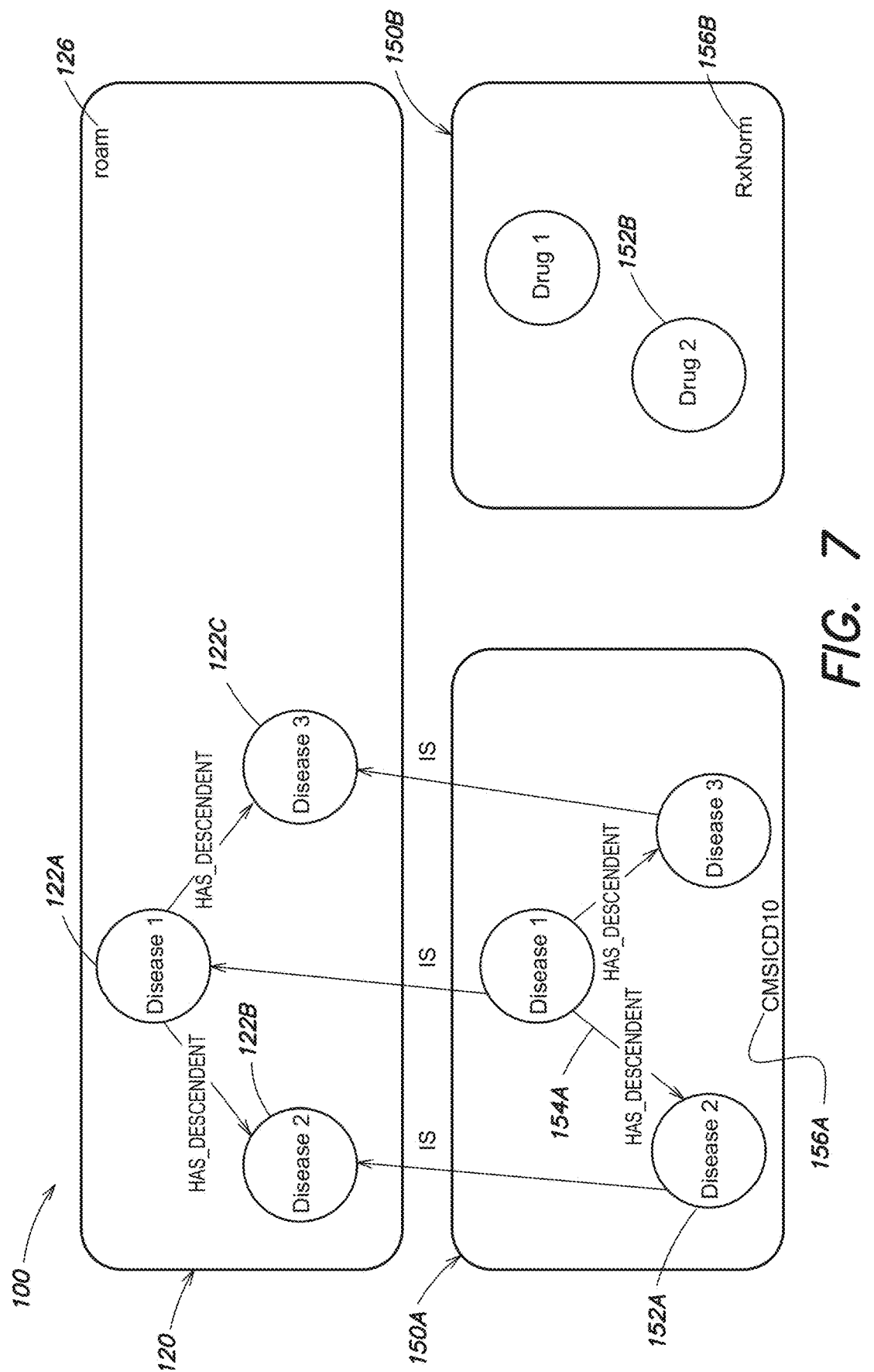
FIG. 7 illustrates the state of graph-building for the example RKG shown in FIG. 1 after the method of FIG. 6 has been applied to a first subgraph of the RKG, according to one inventive implementation.

To illustrate the application of the method 600 shown in FIG. 6 in the context of the example RKG 100 of FIG. 1, FIG. 7 illustrates the state of graph-building for the RKG 100 shown in FIG. 1 after the method of FIG. 6 has been applied to the subgraph 150A representing the CMSICD10 dataset. Similarly, FIG. 8 illustrates the state of graph-building for the RKG 100 shown in FIG. 1 after the method of FIG. 6 has been applied to both the subgraph 150A representing the CMSICD10 dataset and subgraph 150B representing the RxNorm dataset.

Figure 8:
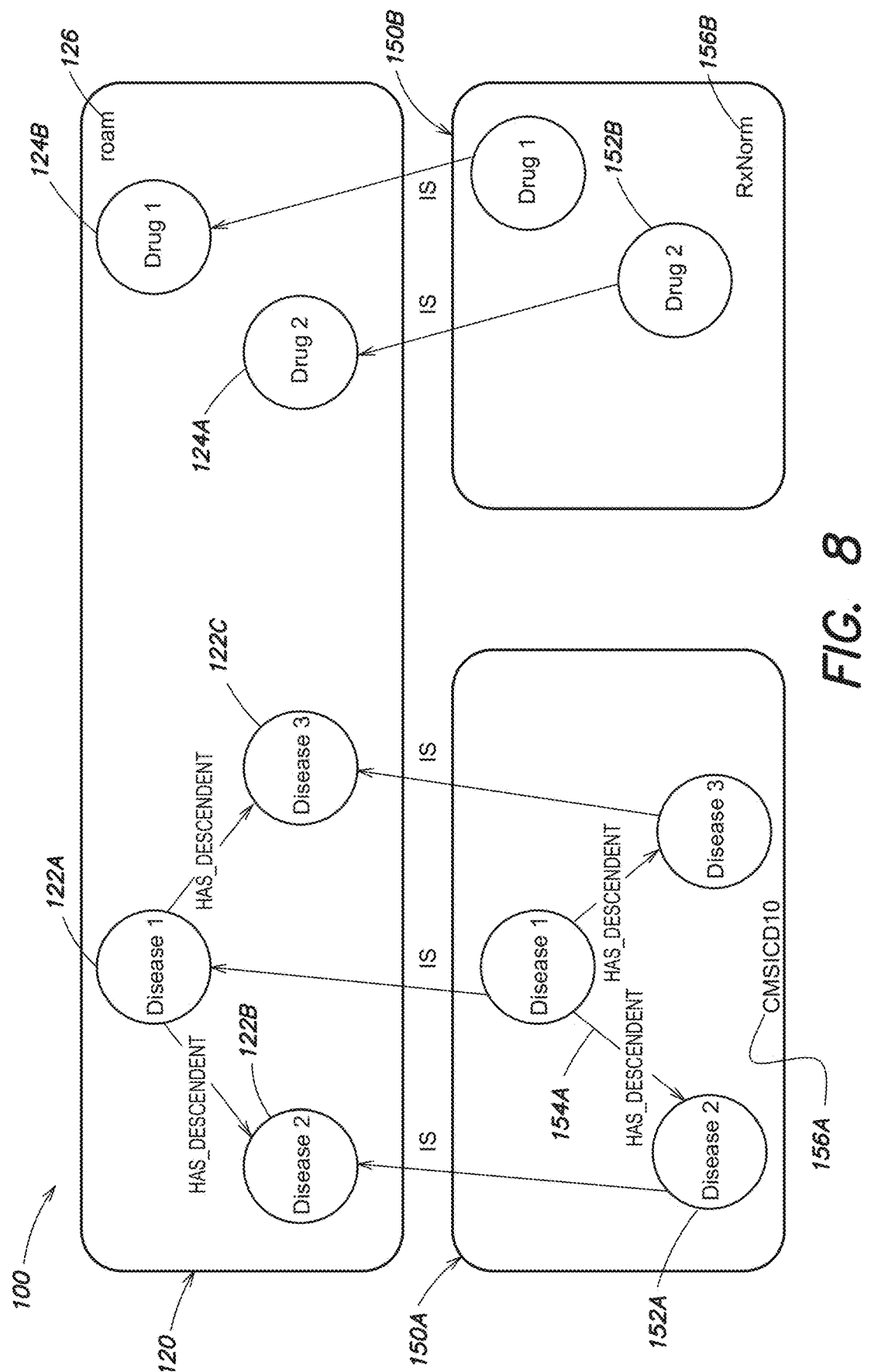
FIG. 8 illustrates the state of graph-building for the example RKG shown in FIG. 1 after the method of FIG. 6 has been applied to both a first subgraph and a second subgraph of the RKG, according to one inventive implementation.

In the discussion above of FIGS. 6, 7 and 8, the edges that are run between the subgraphs and the canonical layer in these examples may be based on relatively straightforward logic, specifically if the canonical layer is being populated with nodes of particular types for the first time (e.g., based on subgraphs of fundamental datasets). More generally, as noted above, edges may be generated between subgraph nodes and canonical nodes of certain types (or between two canonical nodes) pursuant to defined logic (e.g., in a suitable programming language) based on a variety of criteria. The codification of such logic to definitively generate an edge between two nodes is referred to herein as a "logic-based connector."

For example, a logic-based connector may be defined so as to connect a subgraph node of type X to canonical node of type X with an edge of type "IS" if the respective primary identifiers of the nodes match (e.g., when a subgraph node is copied to the canonical layer). Similarly, such logic may be defined so as to connect a subgraph node of type Y to a canonical node of type Y with an edge of type "IS" if respective attributes A1, A3 and A5 have the same values for the respective nodes (e.g., in some instances in which canonical nodes of the type Y already populate the canonical layer, and a new subgraph is being considered for connection to the canonical layer). In another example relating to connection of canonical nodes, logic for forming certain edges may be defined so as to connect canonical node J of the type "Person" having an attribute "A3-Residence State"

with canonical node K of the type "U.S. States" having an attribute "A1-State Name" with an edge of the type "LIVES_IN" if (J, A3=K, A1). Accordingly, a variety of edges between nodes can be generated with certainty based on matching one or more attributes of the respective nodes pursuant to a logic-based connector.

Model-based Connectors

In another inventive aspect, an edge may be generated between a subgraph node and a canonical node, or between two canonical nodes, based on a trained machine learning (ML) model that predicts, with some degree of certainty, the relationship between the two nodes. ML model-based definitions for generating an edge between two nodes, in the context of an RKG pursuant to the inventive concepts disclosed herein, is referred to as a "model-based connector." In general, the design of a given model-based connector supports the basic decision-making logic "should an edge be created between these two nodes or not?" In various implementations, a model-based connector may be defined (codified) using a suitable programming language (e.g., as discussed above, the Python programming language may be employed) and executed at an appropriate time as part of an overall RKG-building process.

In various aspects, the design of a model-based connector may be situation-based in that it may be tailored to particular node types and available attributes, one or more characteristics of particular datasets, target types of relationships (e.g., desired outcomes) and/or various information derived or inferred from node types other than those for which the edge is generated by the model-based connector. In some examples, a model-based connector may add one or more attributes to one or more of the nodes for which an edge may be generated (e.g., to interpolate missing information about a given subgraph node or canonical node) as a predicate for establishing the relationship between the nodes.

Various types of ML models suitable for purposes of designing a model-based connector according to the inventive concepts herein are known in the relevant arts, examples of which include, but are not limited to, Binary Classification, Multiclass Classification, Linear Regression, Logistic Regression, Decision Tree, Support Vector Machine, Naive Bayes, kNN, K-Means, and Random Forest.

With reference again to the example RKG 100 shown in a formative state in FIG. 8, after the canonical nodes have preliminarily populated the canonical layer 120, and respective subgraphs 150A and 150B have been connected to the canonical layer pursuant to the method 600 outlined in FIG. 6, a next phase of graph-building may involve one or more model-based connectors to generate edges between canonical nodes. For example, with reference again to FIG. 1, the two edges of the type "TREATS," one between the node 124B (roam/Drug/Drug 1) and the node 122B (roam/Disease/Disease 2), and another between the node 124A (roam/Drug/Drug 2) and the node 122C (roam/Disease/Disease 3), may be generated via a model-based connector.

For example, the model-based connector may be designed to add an attribute to each canonical node of the type "Drug" to specify one or more diseases that the drug treats, with some degree of certainty. In some implementations, the model-based connector may add such an attribute to canonical nodes of the type "Drug" based at least in part on information derived or inferred from one or more other datasets (that may or may not be part of the RKG) on which an ML model has been trained. In some implementations, the model-based connector also may add a probability attribute to the nodes of the type "Drug" in connection with the newly-added disease attribute. The logic for the model-based connector may then generate an edge of the type "TREATS" between a given canonical drug node and a given canonical disease node based on matching the model-based disease attribute newly added to the drug node with a corresponding attribute of the disease node. In some implementations, the probability attribute may also (or alternatively) be added as an attribute of the edge of the type "TREATS." The result of applying such a model-based connector as part of a graph-building process, as an additional step following the method outlined in FIG. 6, is illustrated in the example RKG 100 shown in FIG. 1.

Although the example discussed above illustrates the use of a model-based connector to generate an edge between two canonical nodes, it should be appreciated that model-based connectors may be employed liberally in the graph-building process to generate edges having a wide variety of types between subgraph nodes and canonical nodes, or between canonical nodes. Additionally, given the variety of ML algorithms that may be employed as a basis for a given model-based connector, as well as the range of training data that may be available to such algorithms, it should be appreciated that a wide variety of relationships may be inferred between entities represented by nodes in an RKG, using a model-based connector, to thereby generate edges between nodes with a certain degree of certainty ("confidence").

In another example of a model-based connector, consider a situation in which there are multiple nodes of a certain canonical node type already populating the canonical node layer of an RKG, and each of these nodes has a certain set of attributes. For this example, we consider a canonical node type "roam/Provider" representing various health care practitioners. Also for this example, consider that there are already multiple subgraphs in the RKG having nodes of the type "Provider," each with corresponding attributes and connected to a corresponding canonical node of the type "roam/Provider" via an edge of the type "IS."

Now consider a new dataset for addition to the RKG. Upon initial analysis of the new dataset, it is evident that there are health care professional entities prevalent in the dataset; however, there are no attributes of these entities in the new dataset that would permit exact matching to canonical nodes of the type "roam/Provider" (e.g., pursuant to the method outlined in FIG. 6). In this scenario, a model-based connector may be designed to determine nodes of the type "Provider" in a subgraph representing the new dataset that sufficiently correspond to respective ones of the set of nodes "roam/Provider," and then connect these nodes via an edge of the type "IS" with a corresponding probability attribute (or "confidence" value, e.g., from 0 to 1 inclusive). In one example implementation, the logic for such a model-based connector may be based on training an ML classifier.

To facilitate design of a model-based connector in the above example, the existing RKG prior to addition of the new dataset may be queried (as discussed further below) to extract entity types, entities, and attributes for entities that are deemed to be relevant in some manner to the new dataset, and these may be organized in tabular form. Similarly, early portions of the method 300 shown in FIG. 3 (e.g., blocks 310 and 320) may be performed on the new dataset to generate a single "cleaned" dataset file in a similar tabular form (or the new dataset may be used "as-is" if it is already in an appropriate tabular form). Thus, relevant information extracted from the existing RKG and the new dataset are represented as two tables (e.g., in which the column headers for the respective tables may represent in some manner one or more entity types included in the table, and in which respective rows in each table include values for the entities of the types represented by the column headers). For a given dataset, such tables may include relatively few or several rows, and in some instances hundreds if not thousands of rows. An example of one row for each such table is provided below for purposes of illustration:

| Existing RKG | | | | |
|---|---|---|---|---|
| Last | First | Zip | Affiliation | Specialty |
| Kim | Zoltani | 94304 | Stanford | Dental Surgeon |

| New Dataset | | | | |
|---|---|---|---|---|
| Last | First | Zip | Affiliation | Specialty |
| Kim | Zoltan | 94305 | Stanford Hospital | Dentistry |

Next, the process of designing a model-based connector to connect nodes of a subgraph representing the new dataset to sufficiently corresponding nodes in the canonical layer may employ "active learning." To this end, human annotators would be presented with pairs of entries from each of the two tables and asked to say "Yes, these rows respectively refer to the same person" or "No, these rows respectively refer to different people." Once the human annotators provide a relatively small number of such labels, an ML model (e.g., for a classifier) may be developed for the model-based connector and trained on the initial human annotations. As noted above, there are multiple algorithmic choices for developing such an ML model (e.g., Logistic Regression, Support Vector Machine, Decision Tree). Common to all of these models is the requirement that a feature function be created ("featurization") which is run on raw inputs (in the current example, table rows) to obtain purely numerical representations (e.g., degrees of certainty regarding a possible match). Below is an example of how the two example rows presented above may be "featurized:"

| Identical last names | Identical last initials | Identical first names | Identical first initials | Identical affiliation string | Specialty distance | Geo distance in miles |
|---|---|---|---|---|---|---|
| 1 | 1 | 0 | 1 | 0 | 0.8 | 2 |

In some implementations, the existing RKG itself may be used to build such feature functions. For example, the existing RKG might be used to obtain the 'Specialty distance' values, which indicate how far apart two specialties are in the canonical taxonomy of medical specialties. Similarly, the existing RKG may be useful in getting a distance estimate between two zip codes, in normalizing place and entity names, and in doing more sophisticated name comparisons (e.g., the likelihood of the name Zoltan Kim given the likelihoods of Zoltan as a first name and Kim as a last name).

An ML classifier for the model-based connector may now be trained on the feature representations of the human annotated examples. Fundamentally, this means learning to weight the features in the above table to maximize the likelihood of the human annotated examples. With the model initially trained, it can be used to more strategically select additional rows of the respective tables for the human annotators to label to iterate training cycles. Once the model is performing at an acceptable confidence level, it can then be deployed on the entire new dataset to predict corresponding nodes with sufficient certainty and generate edges of the type "IS" between such pairs of nodes (with the uncertainty recorded as an attribute of the edge of the type "IS"). For the above example, it is likely that a trained model for the model-based connector would say with relatively high confidence that a node in the subgraph representing the Zoltan Kim row in the new dataset identifies the same entity as indicated in the row extracted from roam/Provider; accordingly, the model-based connector would add an edge of the type "IS" between these corresponding nodes in the new dataset and the canonical layer, thereby enriching the RKG with all the information present in the new dataset.

Coordinating the RKG-building Process

Based on the foregoing discussion on the rudiments of building an RKG according to the inventive concepts disclosed herein, it should be appreciated that RKGs of varying and arbitrary complexity may be built according to these rudiments. For example, an RKG relating to a given domain or domains of interest may be based on several dozens of sizeable datasets from multiple different sources, and thus may include several millions of nodes and edges.

To coordinate and execute the various steps of the methods outlined in FIGS. 3 and 6 for multiple potentially large and complex subgraphs, as well as execute a substantial number of logic-based connectors and model-based connectors, a workflow management system may be employed to define and execute various tasks corresponding to these functions. In general, a "task" is a unit of work corresponding to a particular function relating to graph-building (e.g., "build a subgraph for dataset X," "populate the canonical layer with nodes of type Y from dataset Z," "run model-based connector Q to connect canonical nodes of type R to canonical nodes of type S"). In some implementations, many dozens if not hundreds of such tasks may be defined to build an RKG. As may be appreciated from the discussion above, some of these tasks may be performed contemporaneously (in parallel), while some tasks may depend on the completion of one or more other tasks and thus need to be performed in a particular sequence (in series).

In view of the foregoing, in some example implementations a workflow management system based on Directed Acyclic Graphs (DAGs) for organizing tasks and defining dependencies between tasks is employed to facilitate the process of building an RKG. In particular, one or more DAGs may be employed to schedule tasks that may be done periodically (e.g., see blocks 310 and 320 of FIG. 3), run tasks in parallel on multiple computing systems (to reduce execution time for graph-building), and facilitate changes to the RKG and reordering of tasks over time (e.g., as new datasets are considered for expansion of the RKG). One example of such a workflow management system suitable for purposes of RKG building according to the present disclosure is provided by Apache Airflow.

To facilitate the use of DAGs to organize and execute the graph-building process, in another inventive implementation a library of functions and other computational objects (collectively referred to as "graph-building tools") may be created (this library is also referred to herein as "Gryphon"). In one aspect, such a library may be considered a domain-specific programming language (e.g., implemented in Python) to define different "classes" and "objects" (in the sense of object-oriented programming) corresponding to various functions and definitions germane to graph-building (e.g., configuration files or descriptors for subgraph schema;

code for logic-based or model-based connectors). In another aspect, with respect to the database management system in which an RKG is created and maintained, the library may be essentially data format-agnostic and database-agnostic. As a DAG executes tasks, it may call on various objects in the library (e.g., via a pointer to a particular object) to execute a particular task.

In one example implementation, a library of such graph-building tools may include a class of objects referred to as "Downloaders," i.e., the set of all files that respectively codify the process of downloading (ingesting) datasets via the Internet to corresponding isolated namespaces in computer storage (e.g., see FIG. 3, block 310). In this respect, it should be appreciated that there is typically one downloader file in the class "Downloaders" for each dataset to be included in the RKG. Similarly, the library of graph-building tools may include a class of objects referred to as "Importers," i.e., the set of all files that respectively codify the process of creating a single "cleaned" dataset file for each dataset (e.g., see FIG. 3, block 320). A given downloader file and corresponding importer file may be called upon as a DAG executes one or more tasks directed to the ingestion and cleaning of a given dataset.

Another class of objects in the library of graph-building tools may be referred to as "Descriptors," i.e., the set of all configuration files respectively defining graph schemas for subgraphs representing ingested datasets (e.g., see FIG. 3 block 330). In this respect, it should again be appreciated that there is typically one configuration file in the class "Descriptors" for each subgraph in an RKG. Another class of objects may be referred to as "Builders," i.e., the set of all files that respectively apply the graph schema defined in a given configuration file in the "Descriptors" class to a corresponding single cleaned dataset file so as to generate one or more graph files representing a subgraph (e.g., see FIG. 3 block 340). Another class (or individual object) in the library of graph-building tools may be referred to as "RKG_Importer," i.e., a file that codifies the process of importing all subgraphs into isolated namespaces of the RKG (e.g., see block 350 of FIG. 3), to facilitate subsequent population of canonical nodes and generation of edges between subgraphs and the canonical layer.

Yet another class of objects of particular significance in the library of graph-building tools may be referred to as "Connectors," i.e., the set of all files that codify logic-based connectors and model-based connectors (particularly referred to in the library as MBCs) for populating canonical nodes in the canonical layer and generating edges between subgraphs and the canonical layer of an RKG, as well as edges between canonical nodes in the canonical layer (e.g., see block 680 of FIG. 6). Given the wide variety of logic-based connectors and model-based connectors that may be employed in an RKG, the number of files/objects in the class "Connectors" does not necessarily correspond to the number of datasets in an RKG (and generally significantly exceeds the number of datasets). Also, it should be appreciated that some connectors are dependent on other connectors being previously executed (e.g., there may be a strict dependency on the order in which certain connectors are run). The various dependencies of running connectors may be facilitated by the manipulation of tasks within a given DAG.

Figure 9:
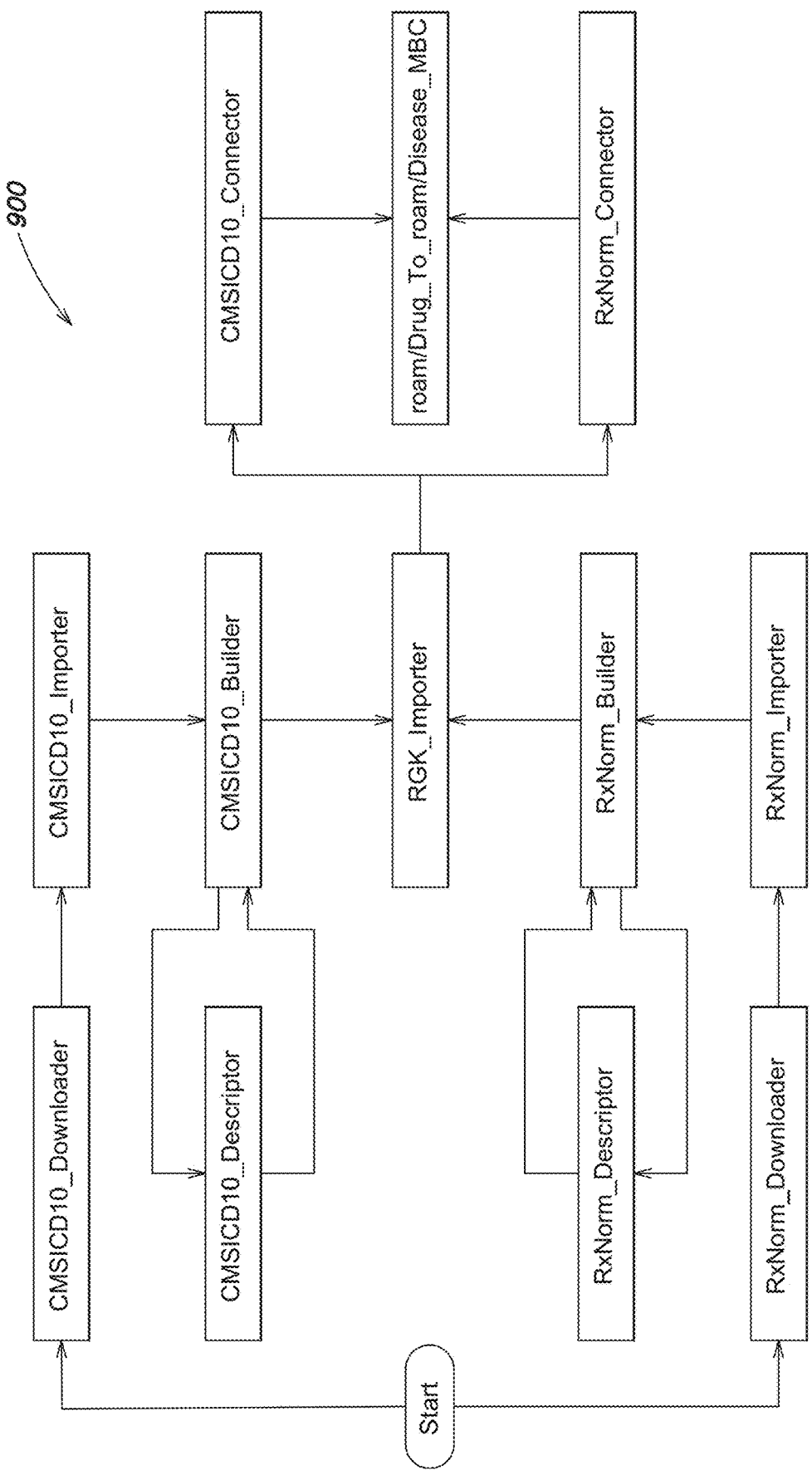
FIG. 9 illustrates an example of a Directed Acyclic Graph (DAG) for building the RKG shown in FIG. 1 using multiple graph-building tools to execute various tasks according to the methods of FIGS. 3 and 6, according to one inventive implementation.

Based on the foregoing example of a library of graph-building tools, FIG. 9 illustrates an example DAG 900 for building the RKG 100 shown in FIG. 1, according to one inventive implementation. As may be observed in FIG. 9, some of the tasks shown in the DAG may be executed in parallel (in which respective tasks call on various objects in the library of graph-building tools), while other tasks are executed in a particular sequence. For example, the tasks of downloading and importing datasets, as well as building subgraphs for datasets, may be executed in parallel. Subsequently, all subgraphs are imported into respective isolated namespaces of the RKG via "RKG_Importer." Thereafter, connectors for each subgraph (e.g., to populate canonical nodes of the canonical layer and connect respective pairs of subgraph nodes and canonical nodes with edges of the type "IS") may be run in parallel, after which a model-based connector (MBC) may be executed to generate edges of the type "TREATS" between canonical nodes of the type roam/Drug and canonical nodes of the type roam/Disease.

Querying a Roam Knowledge Graph (RKG)

In some implementations, the process of querying an RKG according to the concepts disclosed herein is dependent, at least in part, on the graph database management system used to create and maintain the RKG.

Cypher Queries

For example, the graph database management system Neo4j employs the "Cypher" declarative query language. An example query of an RKG stored in Neo4j using Cypher is reproduced below. In the RKG for which the query is constructed, there is a subgraph in the namespace "NPI" having nodes of the type "NPI/Provider," and the canonical layer of the RKG includes canonical nodes of the type "roam/HealthcareProfessional," "roam/Geography/Address" and "roam/Specialty/Specialization:"

```
MATCH(p: 'roam/HealthcareProfessional')
  -[:PRACTICE_LOCATION+->(a: 'roam/Geography/Addresss'{state_code: 'NY'})
MATCH(p)
  -[:SPECIALIZES_IN]->(s: 'roam/Specialty/Specialization')
MATCH(p)
  -[:IS]-(npi: 'NPI/Provider')
RETURN
  p.first_name AS first_name,
  p.last_name AS last_name,
  p.'gender.code' AS gender,
  a.city_name AS practice_city,
  a.state_code AS practice_state,
  s.code AS specialization_code,
  s.classification AS classification,
  npi.NPI AS NPI,
  npi.credential AS credential
```

The above query codifies the following request: "Find all health care professionals in the RKG who practice in New York state and have a practice specialization, and who are also listed in the NPI public dataset, and return various information about these health care professionals." This query starts a search in the canonical layer of the RKG to identify canonical nodes corresponding to health care professionals (node type p: "roam/HealthcareProfessional"), and continues a search within the canonical layer to identify the canonical node for New York state (a: 'roam/Geography/Address' {state_code: 'NY'}) that is coupled to canonical nodes practitioners via an edge of the type "PRACTICES_LOCATON." The search then continues within the canonical layer to further determine those canonical nodes for health care professionals that are not only coupled to the canonical node for New York state, but are also coupled to canonical nodes corresponding to their respective specializations (s: "roam/Speciality/Specialization") via an edge of the type "SPECIALIZES_IN." Based on the results obtained from the search of the canonical layer, the search responsive to the query then looks in the NPI subgraph for nodes of the type "NPI/Provider" corresponding to only those health care professionals identified in the canonical layer search results (i.e., who practice in New York state and have a specialization).

For each healthcare professional that satisfies the above query, the query extracts certain attributes from the respective nodes identified in the search of the graph to provide a results set. In particular, pursuant to the RETURN declarations specified in the query, some attributes are gathered from the canonical nodes of type "p" ("roam/Healthcare-Professional"), some attributes are gathered from the canonical nodes of type "a" ("roam/Geography/Address"), some attributes are gathered from the canonical nodes of type "s" ("roam/Specialty/Specialization"), and some attributes are gathered from the nodes in the NPI subgraph of the type "npi" ("NPI/Provider"). In the present query example, the query also dictates that the result is presented as a spreadsheet with column headers indicated by the RETURN declarations.

Given the size of the NPI dataset, the spreadsheet for the result set corresponding to the Cypter query example above includes hundreds of thousands of rows; a short illustrative excerpt from this spreadsheet is reproduced below:

| first_name | last_name | gender | practice_city | practice_state | specialization_code | classification | NPI | credential |
|---|---|---|---|---|---|---|---|---|
| MAY | KYI | F | BROOKLYN | NY | 390200000X | Student in an Organized Health Care Education/Training Program | 1588085567 | M.D |
| ANUDEEPA | SHARMA | F | BROOKLYN | NY | 282NC2000X | General Acute Care Hospital | 190225428 | |
| ANUDEEPA | SHARMA | F | BROOKLYN | NY | 261QM0855X | Clinic/Center | 1902225428 | |
| ANUDEEPA | SHARMA | F | BROOKLYN | NY | 261Q00000X | Clinic/Center | 1902225428 | |
| PRABHAVATHI | GUMMALLA | F | BROOKLYN | NY | 282NC2000X | General Acute Care Hospital | 1750700852 | M.D |
| O | RAFFO | M | COOPERSTOWN | NY | 207L00000X | Anesthesiology | 1134108244 | M.D. |
| HARISH RAJ | SEETHA RAMMOHAN | M | COOPERSTOWN | NY | 207RC0000X | Internal Medicine | 1497082697 | MD,MRCP |
| HERBERT | MARX | M | COOPERSTOWN | NY | 207RC0000X | Internal Medicine | 1164641254 | M.D. |
| AMIRA | ALFIL | F | BROOKLYN | NY | 390200000X | Student in an Organized Health Care Education/Training Program | 1285045120 | MD,MPH |
| YELVA | LYNFIELD | F | BROOKLYN | NY | 207N00000X | Dermatology | 1194767855 | MD |
| THERESE | MALCOLM | F | BROOKLYN | NY | 207V00000X | Obstetrics & Gynecology | 1558304246 | |
| JOHANNE | THOMAS | F | BROOKLYN | NY | 207L00000X | Anesthesiology | 1134162449 | MD |
| MICHAEL | PITEM | M | BROOKLYN | NY | 2084N0400X | Psychiatry & Neurology | 1225140155 | |
| ROBERT | SPATZ | M | BROOKLYN | NY | 207L00000X | Anesthesiology | 1316988421 | MD |
| MYRON | SOKAL | M | BROOKLYN | NY | 2080N0001X | Pediatrics | 1144263856 | |
| ARUN | KRISHNAN | M | BROOKLYN | NY | 390200000X | Student in an Organized Health Care Education/Training Program | 1790198265 | |

Semantic Parsing Engine

In other example implementations, a "semantic parsing engine" may be employed to formulate queries of an RKG.

In general, a semantic parsing engine according to the inventive concepts disclosed herein provides a mapping from relatively straightforward English language questions to graph queries (e.g., in Cypher). Each query implicitly identifies a "path" through the graph (as discussed above in connection with the Cypher example query); at the same time, the interactive natural language search capability provided by the semantic parsing engine allows users to pose sophisticated queries in English and receive multifaceted structured answers in response.

Semantic parsing engine is graph-backed in the sense that its grammar and semantic concepts are derived automatically from the graph schema, which is also used to guide the user in formulating and modifying natural English queries in a way that facilitates knowledge discovery. This provides a superior search experience compared to raw database queries.

An enormous amount of U.S. health data has been made available for public over the last few years. Taken together, these datasets have the potential to provide a comprehensive picture of the healthcare domain: drugs, procedures, diseases, providers, and so forth. Even if patient-level data is missing, because of privacy considerations, census and survey data can still support analyses based on fine-grained demographics.

An approach to developing semantic parsers over large health knowledge graphs (HKGs) derived from these public datasets is presented herein. These semantic parsers are graph-backed: the schema for the target graph is used to define the core space of entities, entity-types, and relations; it provides the initial seed sets for defining the semantic lexicon; and it helps delimit the space of rules for syntactic and semantic combination Thus, very large and complex grammars are easily instantiated, addressing one of the major bottlenecks for semantic parsing at scale. The graph schema also improves the interface: it feeds a front-end tool for guiding the user in writing English queries and modifying them in ways that facilitate intuitive discovery of the graph's contents.

A use case for the semantic parser can be natural language search into health knowledge graphs. The alternative is a database query language, which can be cumbersome even for experts and which puts most information out of reach for regular users. Natural language search can remove these obstacles.

The public health datasets under consideration here are not released by a single data source using a consistent set of identifiers. Rather, each dataset presents a partial, potentially biased view of the world, the union of all the information in them is likely to be inconsistent, and establishing even simple links between entities often must be cast as a model-based inference under uncertainty.

In this example, on graph-backed semantic parsers, a small subset of public health datasets was selected that can be assembled into a connected graph with high confidence. The approach disclosed herein can be extended easily to vastly larger graphs created with more complex statistical methods. However, the subset has been used to shine a light on the parser's accuracy and coverage.

Figure 10A:
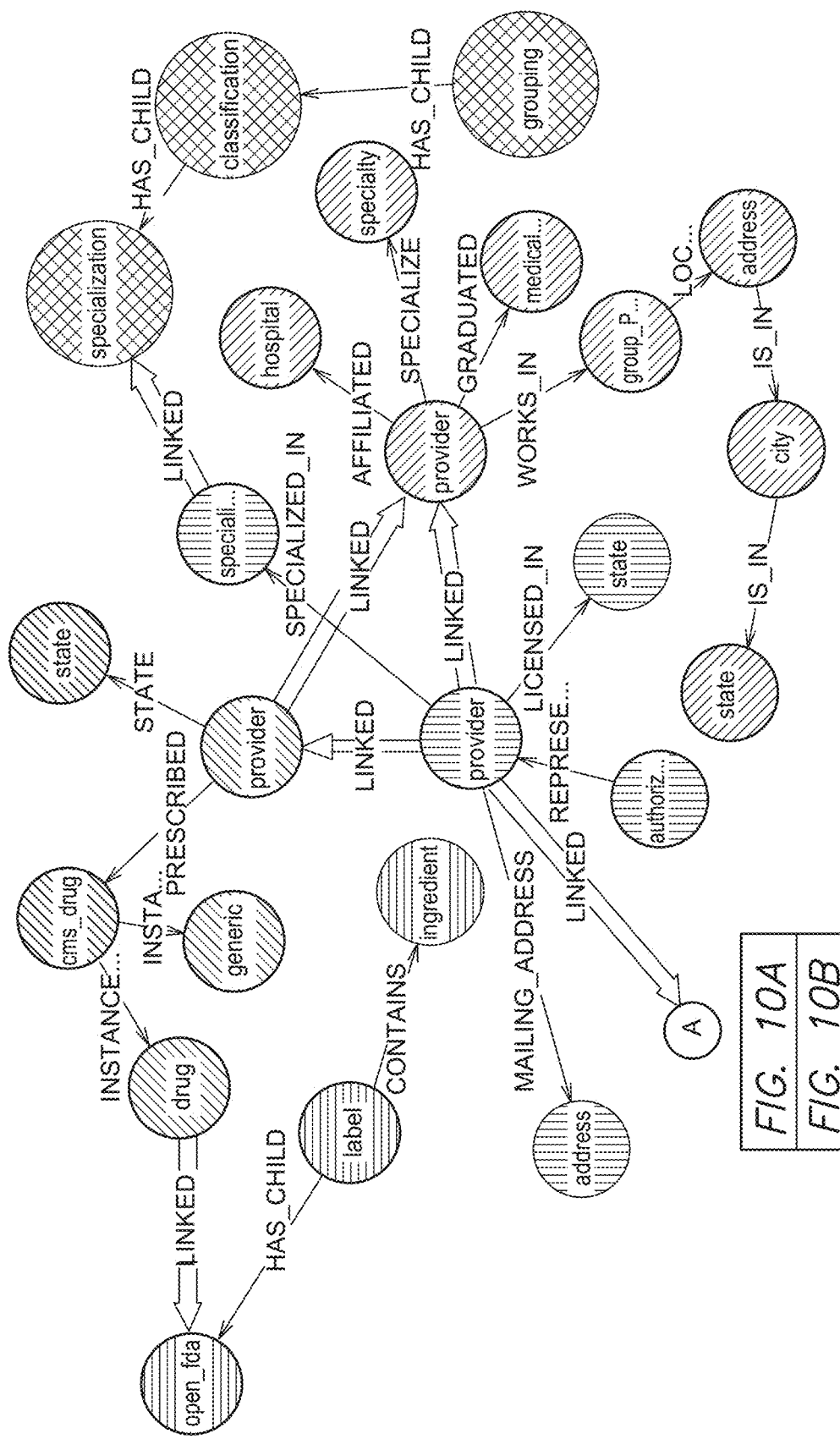
FIGS. 10A and 10B illustrate an example "health knowledge graph" to demonstrate inventive concepts relating to a semantic parsing engine for querying RKGs, according to one inventive implementation.
Figure 10B:
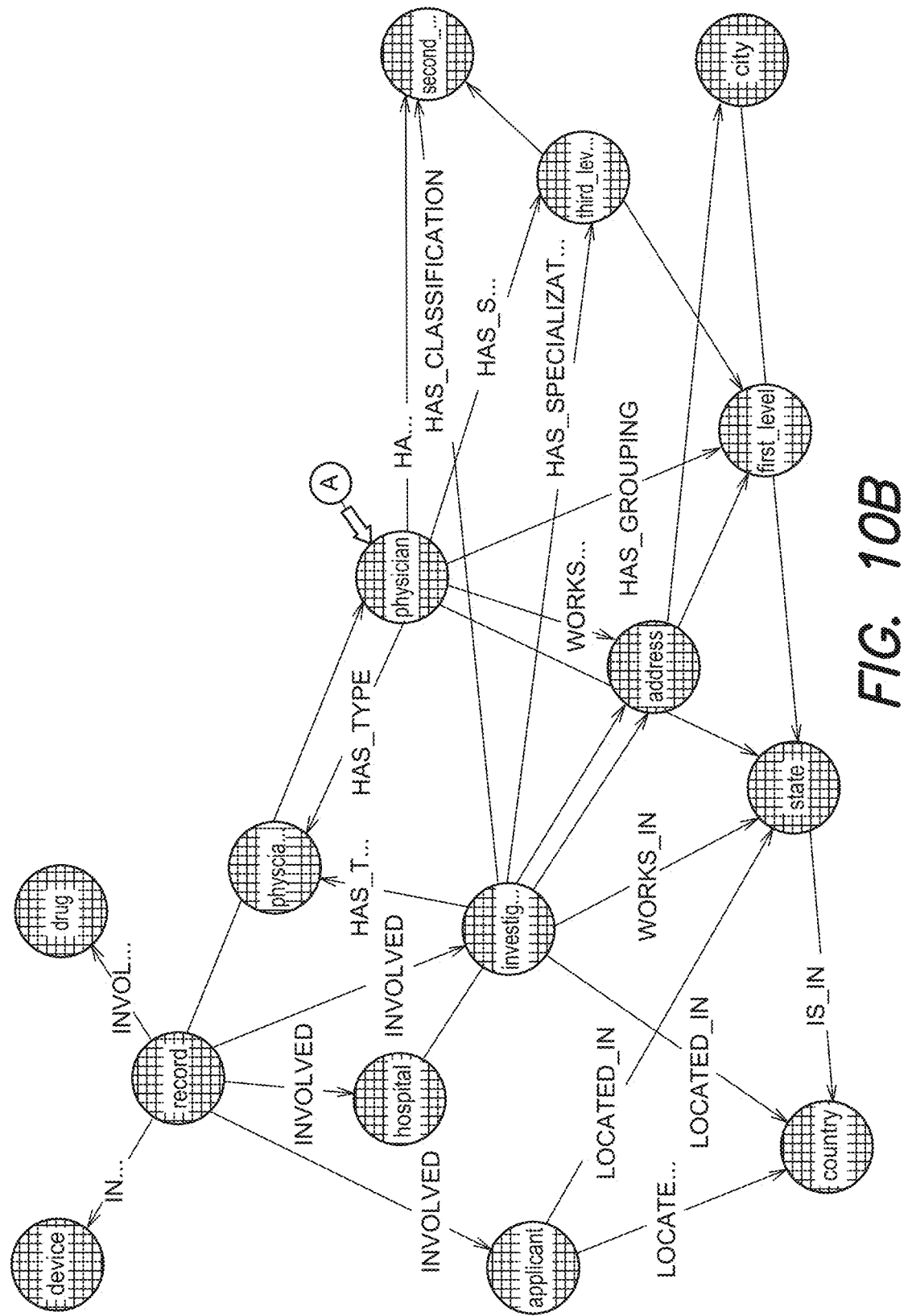

The six datasets that have been selected are summarized in table 1 (FIG. 10C). They are united thematically around physicians and their prescribing behavior. FIGS. 10A and 10B depict the node and edge spaces of the resulting graph. For the most part, these are determined by the structure of the underlying databases.

The edges were added to connect these isolated subgraphs and include the word "Linked". These edges are summarized here: NPI ids connect NPI, CMS Physician Compare, and CMS Prescriptions via providers; taxonomy codes connect the NPI with the Healthcare Taxonomy; brand and generic names connect CMS Prescriptions to FDA Drug Labels via drugs; the CMS Open Payments Research dataset, unlike CMS Prescriptions, does not contain NPI ids, so a log-linear classifier was trained using the Dedupe package, matching 4,263 NPI providers with high confidence. The resulting graph is instantiated in Neo4j, and has 4.6 million nodes and 21.2 million edges.

The Semantic Parsing Engine

Figure 11:
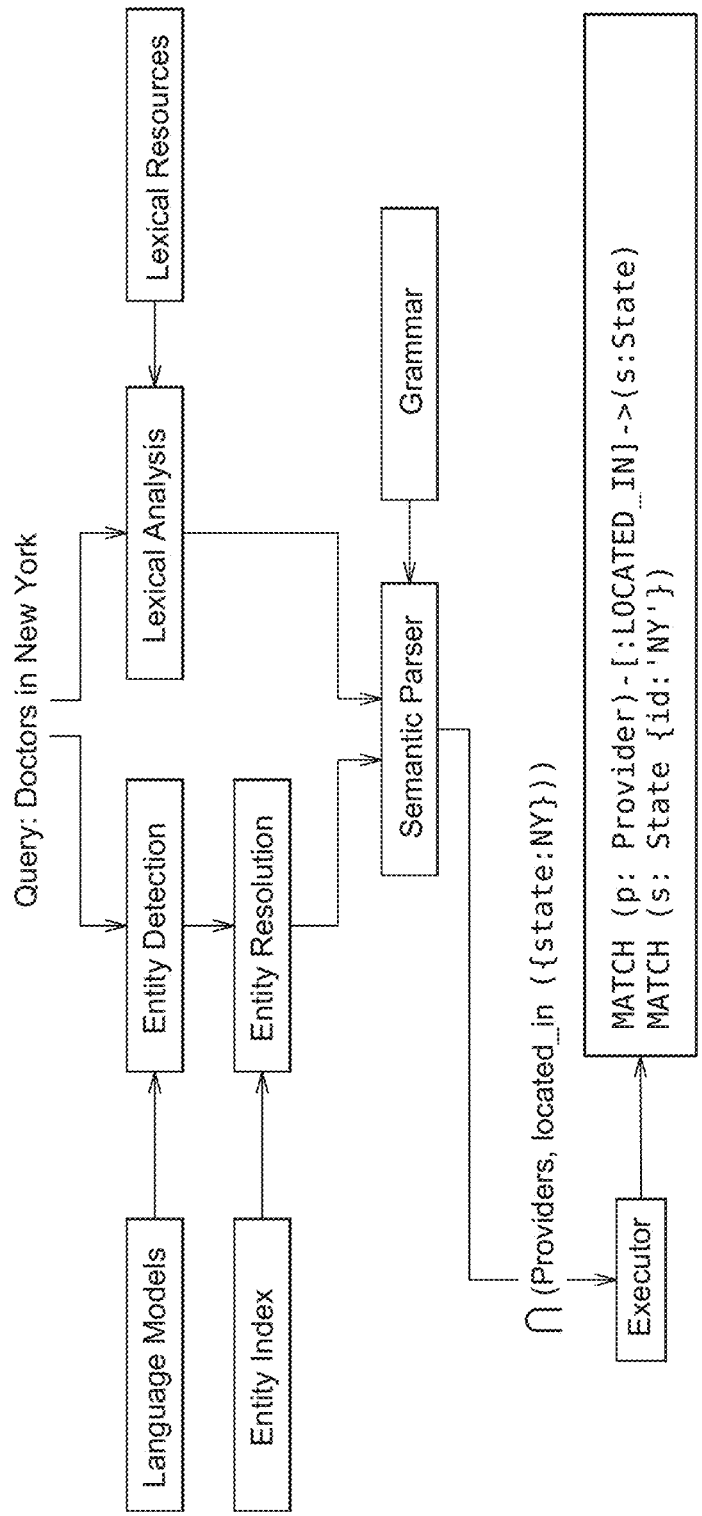
FIG. 11 illustrates a semantic parsing architecture for a semantic parsing engine, according to one inventive implementation.

The semantic parsing engine maps English texts to statements in the declarative Neo4j query language Cypher. FIG. 11 depicts the architecture. The boxes namely "Language models," "Entity index," "Lexical resources," and "Grammar" highlight the numerous ways in which the system is defined by its underlying graph. The language models used for entity detection are trained on 'name'-type attributes of nodes, and resolving those entities is graph-backed: the 'Entity index' is automatically created from the database and provides fast look-up. The 'Lexical analysis' step is similarly graph-backed: node and edge type-names provide the core lexicon, which can then be expand using Wiktionary, WordNet, and heuristic morphological expansion.

The grammar is the most important area of graph-backing; whereas entity and entity-type lists might be obtainable directly from health data resources, semantic grammars are intricate and specialized. Creating and maintaining them is a massive under-taking, and often can be done separately for each database. To avoid this bottleneck, the graph schema can define majority of the grammar rules.

For instance, where the schema contains  Works-in  the syntax rule PERSON→LOCATION PERSON and semantic rule ∩(Works-in {0}, {1}) can be created. Since relations that are intuitively direct sometimes correspond to long paths in the graph, BRIDGING CONCEPT terms are additionally allowed in the logical forms that have no syntactic realization but establish the desired semantic links, equivalently graph paths. The grammar for the example disclosed herein has 1,786 rules.

Figure 12A:
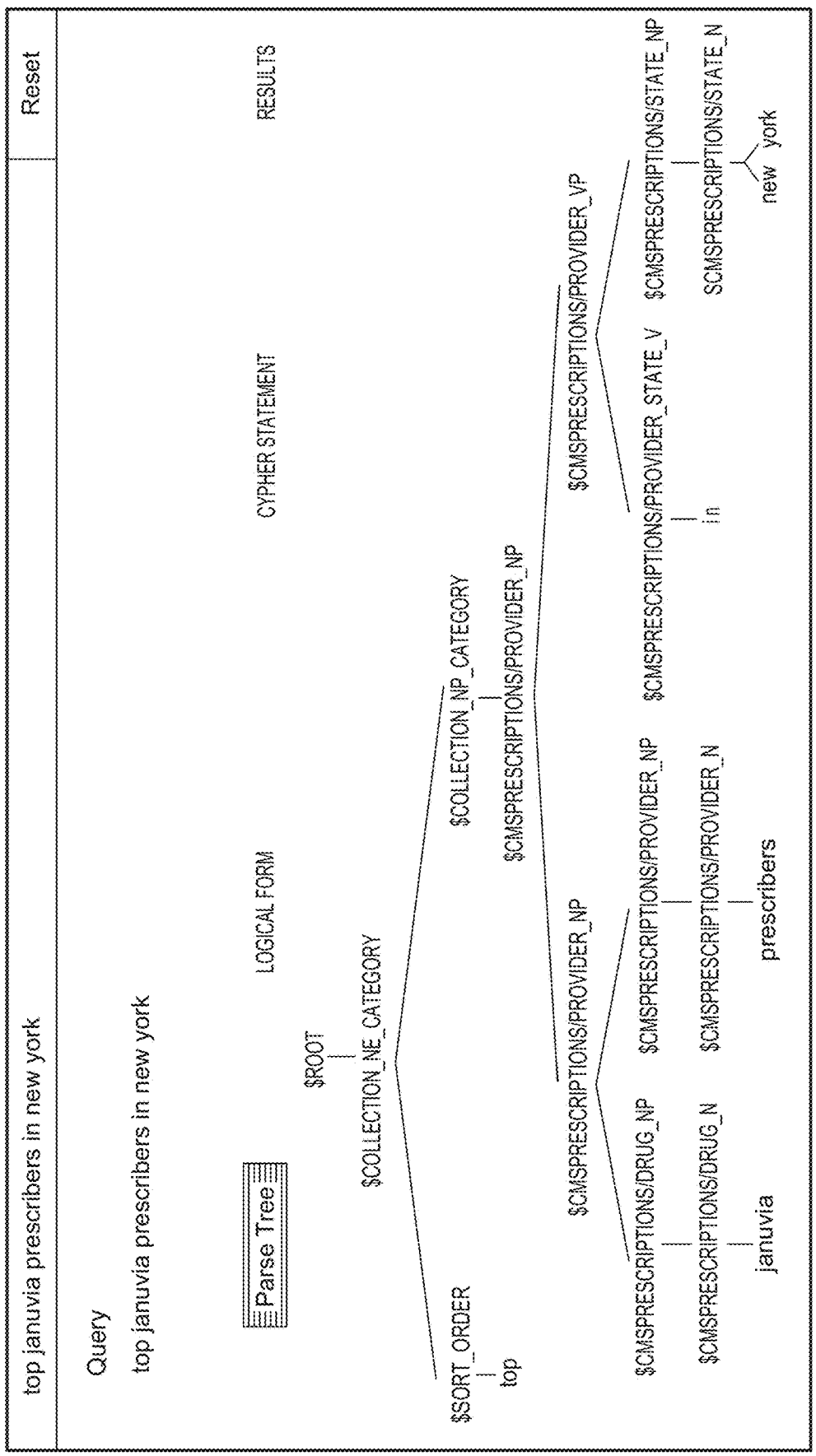
FIG. 12A illustrates an example of a syntactic structure generated by a semantic parsing engine, according to one inventive implementation.
Figure 12B:
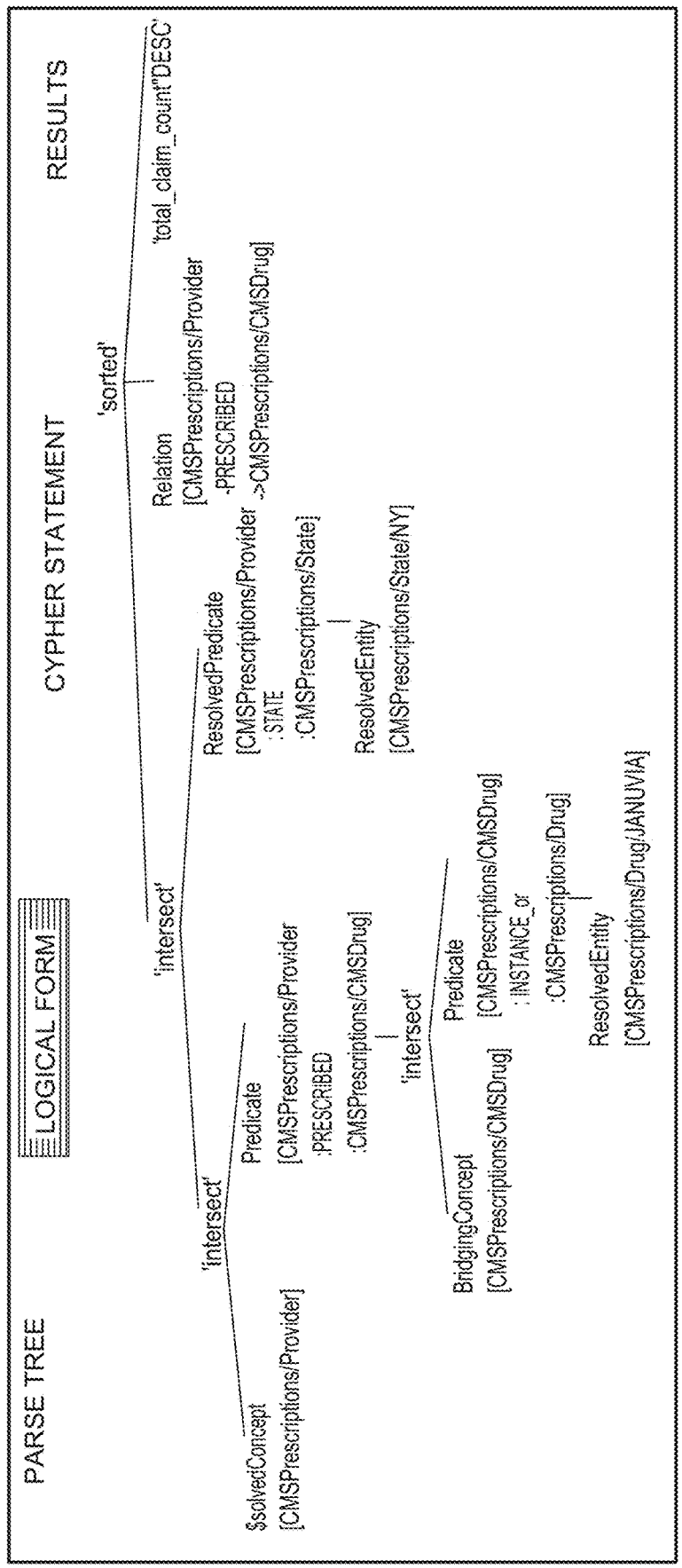
FIG. 12B illustrates an example of a logical form generated by a semantic parsing engine, according to one inventive implementation.

FIGS. 12A-12C illustrate these concepts with partial screenshots of the system's developer view, which exposes the syntax, logical form, and resulting Cypher query for the user's input (along with the database results as a table, not show here). The example is top Januvia prescribers in New York. This query involves three uses of the intersect operator as well as one use of sorted, triggered by the superlative modifier top. Because the CMS Prescriptions sub-graph uses internal 'cms drug' nodes (seen near the top of FIGS. 10A and 10B), a BRIDGINGCONCEPT is triggered to relate provider to drug in the expected way. Where the engine is unable to generate a complete parse, it backs off a search strategy that looks for valid paths in the HKG that include the detected entities and entity types.

Figure 13:
FIG. 13 illustrates an example user interface for a semantic parsing engine showing query expansion and modification, according to one inventive implementation.

The graph is also essential to the user interface. In general, a user's query will reflect a general question. The query is an attempt to sharpen that question in pursuit of actionable intelligence. Presenting the query's results in isolation often doesn't do much to serve this goal; the more the search engine's response can reveal about the underlying graph, the more useful it is. To achieve this, the graph schema can be relied on. FIG. 13 is a snapshot of the user interface that shows how this is done. For any entity-type ("concept") or relation in the query, the user can click on it to see alternatives to it from the graph, as determined by the entity types and graph structure. In FIG. 13, the user has clicked on a state, and the interface has suggested other states that could be put in that position, also giving guidance on how they can be typed in and providing a free text field for making other substitutions. This facilitates rapid query exploration, with the interface accumulating the results for high-level comparisons.

"Graphitect"-Methods and Systems for Defining Graph Schemas

With reference again to block 330 of the method 300 shown in FIG. 3, a graph schema is created for a dataset to define the node types and the edge types that are used in the subgraph to represent the dataset. An example of such a graph schema is shown in FIG. 4 (representing the NPI public dataset).

As noted above, the graph schema for a given dataset may be encoded in various manners (e.g., using a suitable coding language and/or file format) to generate a configuration file (also referred to herein as a "descriptor file") defining the graph schema. In particular, to store and maintain a dataset as a subgraph in a graph database, in various aspects a programmer/developer/designer (referred to herein as "developer") generally needs to: (1) pre-process the dataset; (2) mentally visualize the graph schema for the dataset; (3) manually draw the graph structure (e.g., to provide an illustrative preliminary example for themselves); (4) hardcode the graph schema in a suitable programming language (i.e., hardcode the nodes, edges, and often times the attributes of the nodes and edges); and (5) import the hardcoded graph schema files to a suitable graph database management system. This process typically is lengthy and arduous, and often requires multiple iterations and "code quality control" interventions at different phases of the development project to ultimately generate an appropriate graph schema for the dataset (e.g., that may be effectively joined to an RKG to augment the information contained therein and facilitate queries of the RKG based at least in part on the augmented information).

In view of the foregoing, the Inventors have also developed inventive methods and systems for defining graph schemas that significantly facilitate the development process for defining such schemas (e.g., by significantly increasing the efficiency of the development process and thereby dramatically reducing development time and increasing the efficacy of the resulting graph schema). In the discussion below, such methods and systems for defining graph schemas are referred to generally herein as "Graphitect." In exemplary inventive implementations, Graphitect can include a Graphical User Interface (GUI) and a graph schema visualization interface. In this manner, Graphitect enables a developer to define graph schema for a dataset while simultaneously visualizing the graph structure before importing the graph schema to a suitable database management system. In example implementations, the development tools provided by Graphitect in some instances obviate the need for the time-consuming and arduous work of manually drawing the graph structure and hardcoding the graph schema.

The GUI in Graphitect enables developers to generate graph schemas by allowing the developers to simultaneously create and visualize a graph structure for a dataset. Thus, the graph structure can be visualized before, or in tandem with, the creation of the graph schema. The output of Graphitect may be a configuration file (e.g., JSON file) that defines nodes, edges, and attributes for a dataset. The configuration file along with the original dataset can seamlessly create the graph of nodes and edges in a suitable graph database management system (e.g., Neo4j).

Graphitect Provides Technological Improvements to Existing Computer Technology

Hardcoding the graph schema for a dataset can be a lengthy process involving writing many lines of code and subsequent deployment of the code. Graphitect significantly facilitates this process by automatically generating the code for the graph schema and thereby saving time.

Hardcoding the graph schema also implies that the developer will have to pay attention to the syntax while defining the nodes and edges. Generation of nodes and edges can be an issue if the hardcoded graph schema includes syntactic errors and bugs. Graphitect can eliminate syntactic errors by automatically transforming the output code to appropriate suitable syntax.

In addition, Graphitect reduces the computational time for building a graph for a new dataset and testing connections within the graph as well as connections between the graph and one or more already existing graphs. Stated differently, when ingesting a new dataset and connecting to an already existing graph (e.g., already existing higher order graph such as RKG) in the same information domain, it can in some instances be difficult to visualize a graph for the new dataset. It can also be difficult to determine how that graph might fit into this already existing graph. Since the GUI platform in Graphitect allows the developer to easily visualize nodes and edges before concretely defining the graph schema, the computational time for defining/changing the nodes and edges before connecting to the already existing graph is reduced significantly.

Graphitect Overview

Graphitect facilitates importing and ingesting a new dataset into a suitable graph database management system without having to manually code graph schema for the new dataset. In some cases, as noted above, a dataset may include a single .csv file, or a dataset may include multiple .csv files that includes information that is related to and relevant to the source of the dataset. Datasets may include structured data or a combination of structured and unstructured data.

Graphitect is particularly applicable to structured elements or structured fields of data. In some cases, these structured fields of data may find themselves in a particular format (e.g., a given table or file) mixed together with other unstructured data elements (e.g., data that contains free text). For instance, to illustrate with a simple example—Emails (and data from Emails) can be converted into a simple spreadsheet with columns "To," "From," and "message content." The fields "To," and "From" may qualify as structured data. However, the field "message content" that includes the message portion (text) of the email the may be unstructured data. Graphitect is applicable to datasets with structured fields of data, whether these fields appear exclusively in a given dataset or appear in a dataset mixed together with other unstructured fields. In some implementations, Graphitect may use structured fields to create nodes and/or edges. Unstructured fields may contribute as an attribute to an existing node and/or edge.

The GUI in Graphitect allows a developer to create nodes based on a dataset. For instance, a developer may determine nodes based on the type of data in the dataset, the data source from which the dataset is obtained, the information domain that the dataset pertains to, column headers/fields in the dataset, and/or knowledge of node types in an already existing graph (e.g., node types in Roam Knowledge Graph (RKG)). In one aspect, every node defined in Graphitect requires at least one attribute as a primary identifier. A primary identifier can also be a combination of one or more attributes. In some examples, the developer can assign one or more attributes to the nodes based on the column headers/fields in the dataset.

In a similar manner, the developer can choose to connect two nodes with an edge. In some implementations, if two nodes have at least one attribute each from a same file in the dataset, Graphitect may recommend connecting the two nodes with an edge. For instance, if node A is assigned attribute 1 from a first .csv file and node B is assigned attribute 2 from the same first .csv file, then Graphitect may recommend that the developer connect node A and node B with an edge. Therefore, if any two nodes in Graphitect draws data from the same file, then Graphitect recommends connecting the two nodes with an edge.

The developer can also choose one or more attributes for each of the edges. In this manner, Graphitect allows a developer to visualize the graph structure and make necessary edits/changes to the graph structure in a simple and user-friendly manner. Once the graph structure is defined by the developer, Graphitect automatically generates a configuration file with the graph schema that defines the nodes and edges for the dataset. A graph database management system (e.g., Neo4j) can generate a graph for the dataset based on the configuration file from Graphitect and a reference to the original dataset.

Roam Knowledge Graph (RKG) and Graphitect

As discussed in previous sections, an RKG is an innovative knowledge graph in which multiple subgraphs representing respective datasets in different namespaces are interconnected via a linking layer (also referred to as a "canonical layer"). In order to import and ingest a new dataset to the RKG, a subgraph representing the new dataset may need to be created. The new subgraph representing the new dataset can then be connected to the overall RKG.

As discussed in the paragraphs above, traditionally, a developer hardcoded the graph schema for new datasets. However, this makes it difficult to determine if the graph structure that is defined by the hardcoded graph schema is a suitable graph structure for incorporation into an RKG. Specifically, a developer can analyze if the subgraph for a new dataset fits into the RKG only after the graph schema and the subsequent subgraph is merged into the RKG. Having the ability to visualize the subgraph before merging into the RKG makes it easier to determine a suitable manner in which the new dataset can effectively augment the RKG.

Thus, Graphitect can create graph schemas for subgraphs representing a dataset in a relatively simpler, faster, and user-friendly manner. In some example implementations, graph schemas for subgraphs in an RKG are generated based on the developer's analysis of the dataset and knowledge of the RKG. These graph schemas are not necessarily generated based on specific strict rules. Therefore, Graphitect is particularly applicable for flexibly and efficiently creating subgraphs that ultimately connect to the RKG.

Graphitect can be used and run multiple times for every dataset. Thus, a graph schema can be generated for every namespace that defines the corresponding nodes and edges for each of the namespaces. A Python script can be run in a pipeline fashion (e.g., as one or more tasks of a DAG) to generate graph schemas using Graphitect for every subgraph and to ultimately interconnect each of subgraphs to the canonical layer in the RKG.

Illustrative Example

The following example illustrates generation of a graph schema for a dataset using Graphitect. The following example is presented primarily for illustrative purposes. The example described below is not mean to limit the scope of the present implementation to a single implementation.

Although some previous examples of datasets discussed herein are related in some manner to the health care domain, an alternative dataset related to musical performance and concerts is considered to demonstrate the various inventive concepts underlying Graphitect. It should be appreciated, however, that the inventive concepts underlying Graphitect may be applied to datasets pertaining to virtually any domain, including the health care domain.

Figure 14:
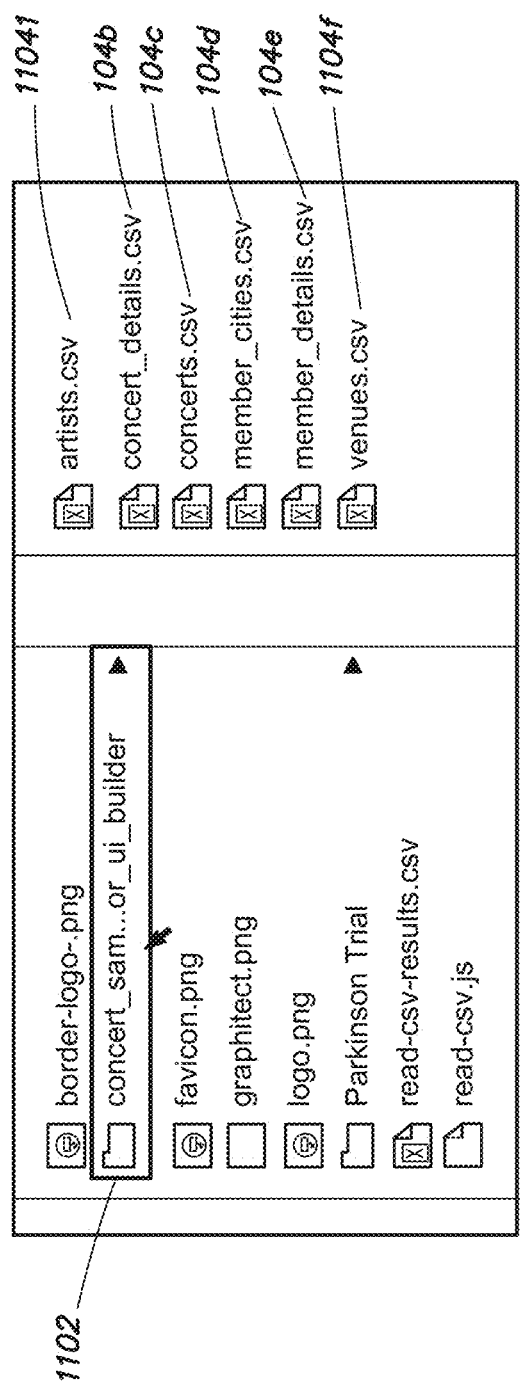
FIG. 14 is a screenshot of a graphical user interface (GUI) illustrating a list of files containing an example dataset to illustrate the "Graphitect" graph development tool for representing a dataset as a graph of nodes and edges, according to one inventive implementation.

FIG. 14 is a screenshot of a graphical user interface (GUI) illustrating a list of files containing an example dataset relating to musical concerts to illustrate the "Graphitect" graph development tool. Concert dataset 1102 is divided into multiple .csv files 1104a-1104f (collectively, .csv (concert data) files 1104). The .csv file 1104a (reproduced below) contains information about bands in the concert dataset 102. Specifically, .csv file 1104a includes band names and band identifiers (the .csv file 1104a maps band names to their corresponding band identifiers).

| Band name | Band identifier |
|---|---|
| Pink Martini | Pm |
| Bread | Bre |
| Wild Nothing | Wn |
| One Direction | Od |

The .csv file 1104b (reproduced below) contains information about different concerts. Specifically, the .csv file 1104b includes concert identifiers, corresponding date of the concert, corresponding venue identifier for the concert (indicating venue for the concert), and corresponding band identifier (indicating the band that plays at the concert).

| Concert identifier | Concert date | Venue | Band |
|---|---|---|---|
| ljk23h1s | Dec. 12, 2017 | fill | Pm |
| 9ybf812 | Dec. 6, 2017 | idp | Bre |
| klyj11234 | Nov. 17, 2017 | bh | Wn |
| p71hj23 | Nov. 13, 2017 | oa | Od |
| j7u1231 | Nov. 14, 2017 | oa | Od |

The .csv file 1104c (reproduced below) indicates the number of tickets that a person bought to a specific concert. Specifically, the .csv file 1104c maps person identifier, concert identifier, and the number of tickets that person bought to the corresponding concert.

| Person Identifier | Concert identifier | Tickets |
|---|---|---|
| dev12345 | ljk23h1s | 2 |
| dev12345 | 9ybf812 | 2 |
| mor12345 | klyj11234 | 4 |
| mor12345 | ljk23h1s | 2 |
| abh12t51 | p71hj23 | 3 |
| alxs2156 | j7u1231 | 1 |

The .csv file 1104d (reproduced below) contains member identifier and the city that member is from (e.g., the .csv file 1104d maps identifiers associated with each person to the city that they are from).

| Member Identifier | City |
|---|---|
| dev12345 | Colombo |
| mor12345 | San Mateo |
| abh12t51 | Mountain View |
| alxs2156 | San Francisco |

The .csv file 1104e (reproduced below) contains person identifier, name, and gender.

| Person Identifier | Name | Gender |
|---|---|---|
| dev12345 | Devini | F |
| mor12345 | Morgan | F |
| abh12t51 | Abhi | M |
| alxs2156 | Alex | M |

The .csv file 1104f (reproduced below) maps venues with venue identifier.

| N | Venue Identifier |
|---|---|
| Fillmore | Fill |
| Independent | Idp |
| Bottom of the Hill | Bh |
| Fillmore | Fill |
| Oracle Arena | Oa |

Figure 15:
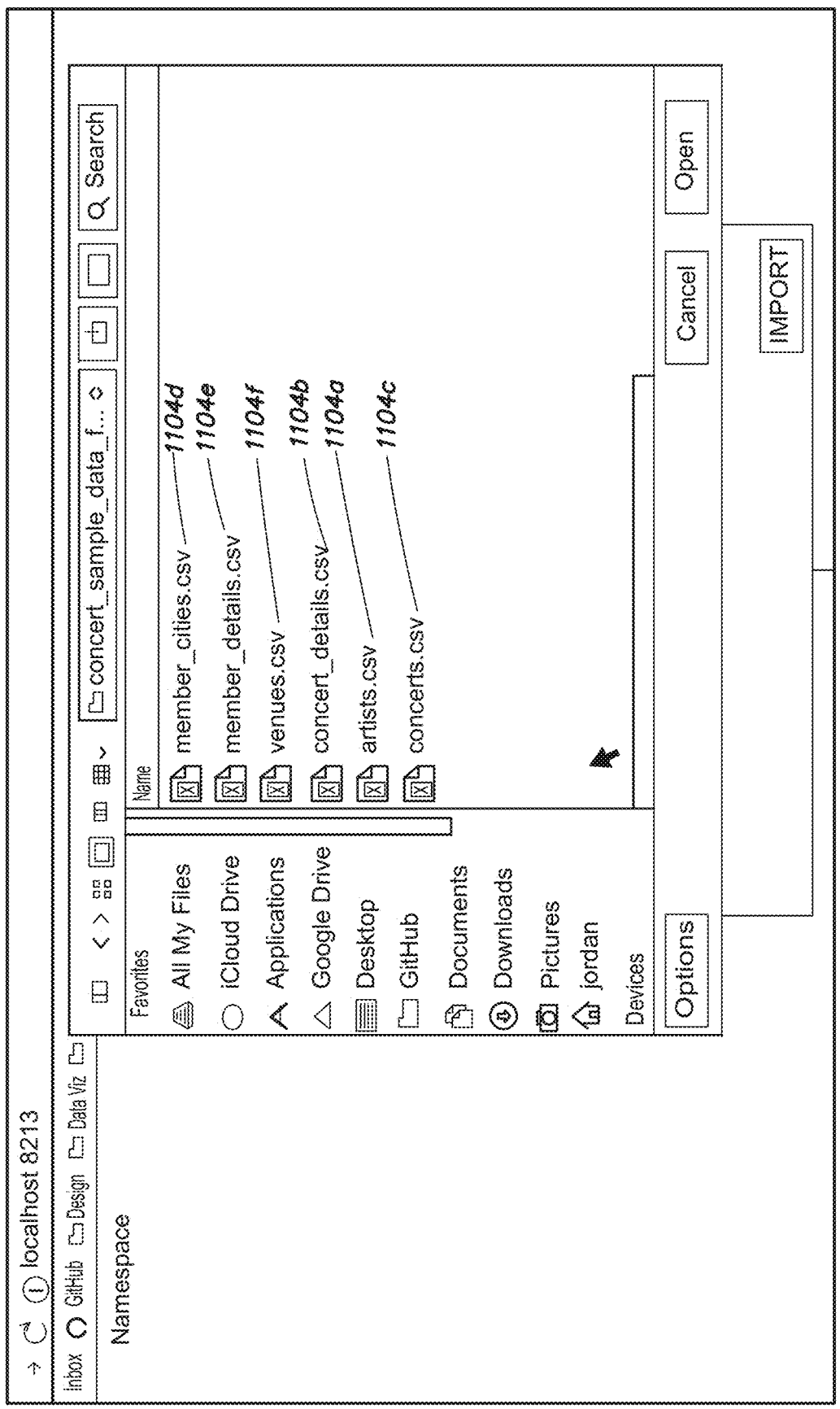
FIG. 15 illustrates importing the files in FIG. 14 to Graphitect, according to one inventive implementation.

The .csv (concert data) files 1104 are imported into Graphitect as shown in FIG. 15.

Figure 16:
FIGS. 16 through 34 illustrate creation of a graph structure for the example dataset using Graphitect, according to one inventive implementation.
Figure 17:
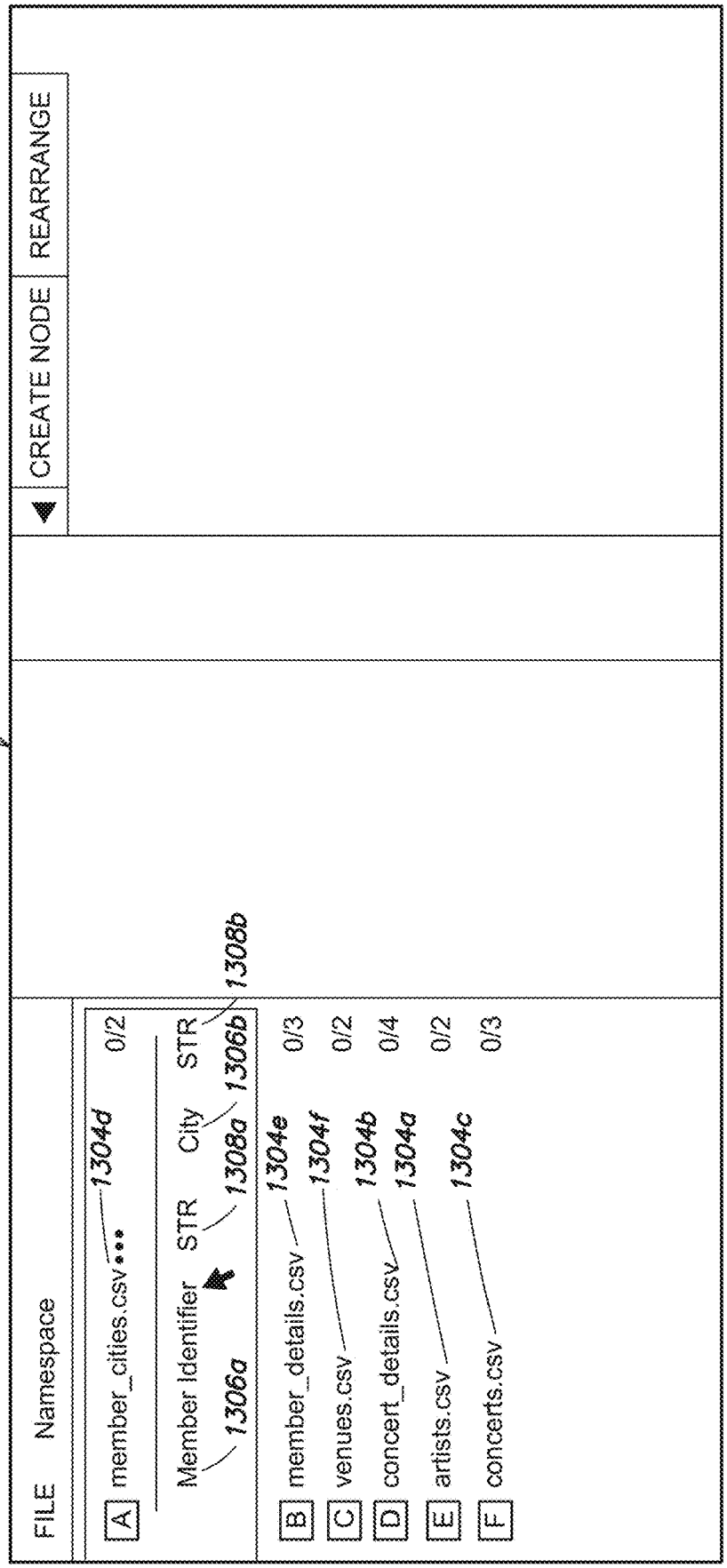

FIG. 16 illustrates GUI 1302 for Graphitect. The imported .csv (concert data) files 1104 are displayed in the left corner of GUI 1302 as 1304a-1304f. Graphitect also displays the column headers in each of the .csv (concert data) files 1104. For instance, in FIG. 17 Graphitect identifies that .csv file 1104d displayed as 1304d in GUI 1302 includes column headers "Member Identifier" 1306a and "City" 1306B. Additionally, Graphitect also determines the type of data in each of the columns. For example, in FIG. 17, Graphitect identifies that the column with column header "Member Identifier" 1306a contains data of type "String" (e.g., 1308a). Similarly, Graphitect identifies that the column with column header "City" 1306b also contains data of type "String" (e.g., 1308b).

The developer can determine nodes for the concert data based on the developer's knowledge of the dataset, column headers, and understanding of the information domain. Every node must have at least one primary identifier. At least one attribute or a combination of one or more attributes can be assigned as a primary identifier to a node.

Figure 18:
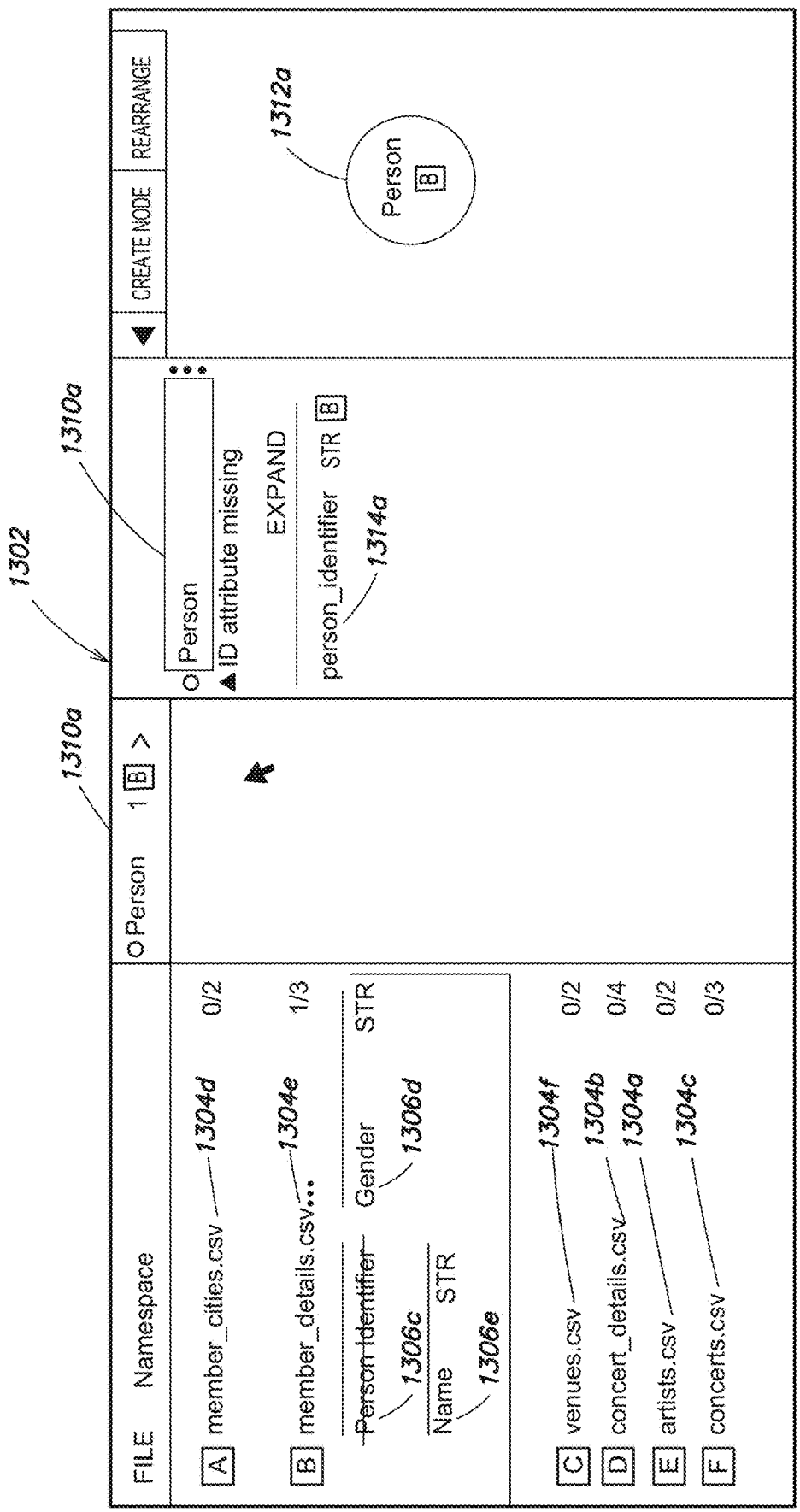

FIG. 18 illustrates creation of a node "Person" 1312a by a developer using Graphitect. The developer may determine that a node of type "Person" 1312a could be advantageous for querying and discovering relationships within the concert dataset. In this example, the developer creates the node "Person" 1312a also represented in tab 1310a. The developer can determine one or more attributes for node "Person" 1312a. In this case, the developer decides that the column with column header "Person Identifier" 1306c from .csv file 1104e represented as "members_details.csv" 1304e in GUI 1302 can be assigned an attribute for node "Person" 1312a. Thus, the developer can drag and drop "Person Identifier" 1306c on tab 1310a (representing node "Person" 1312a) thereby adding "person_identifier" 1314a as an attribute to node "Person" 1312a.

Figure 19:
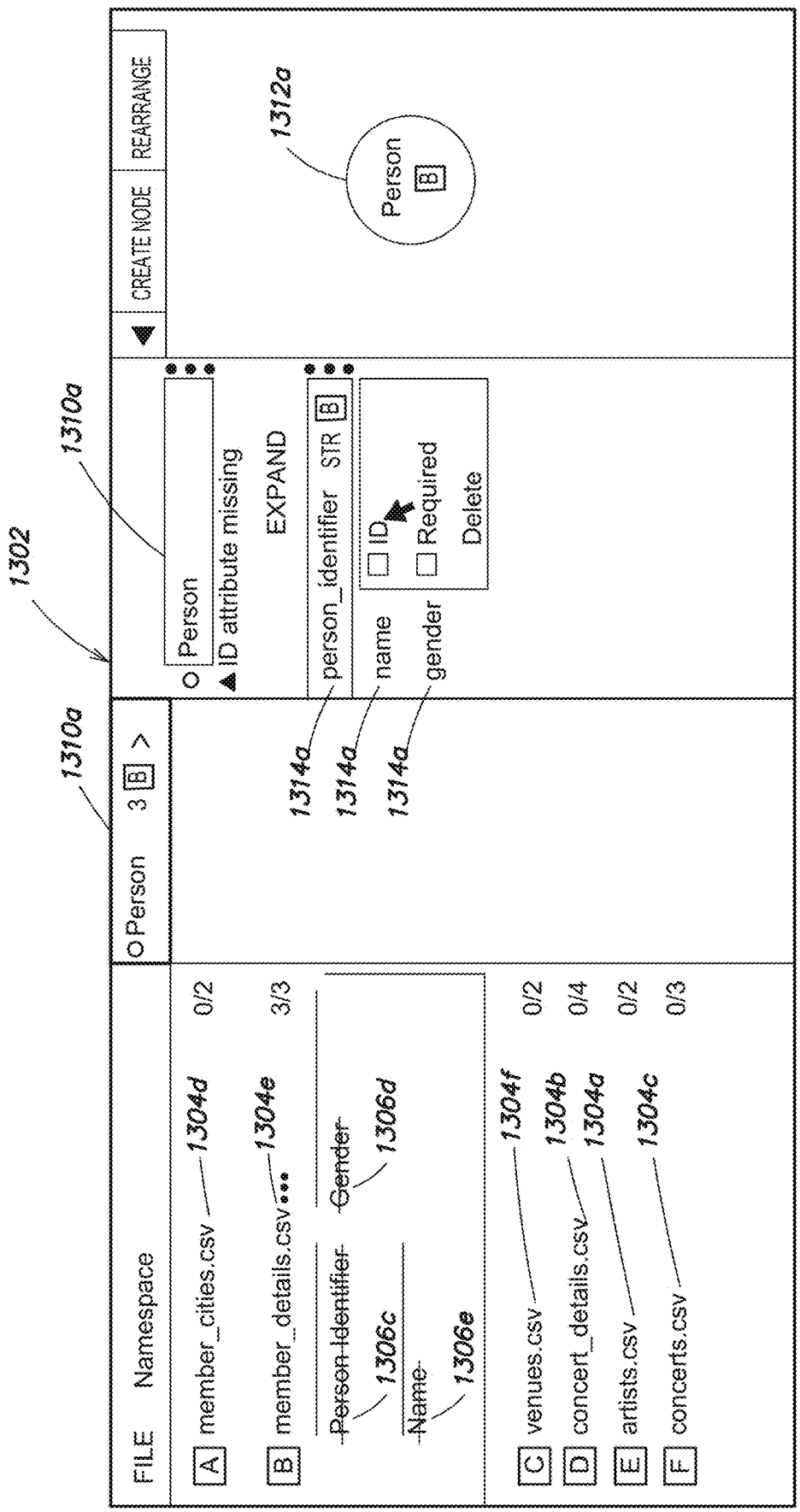

FIG. 19 illustrates addition of attributes to node "Person" 1312a. The developer may also add "Gender" 1306d and "Name" 1306e from .csv file 1104e represented as "members_details.csv" 1304e in GUI 1302 as attributes (e.g., 'name' 1314b, and "gender" 1314c) to node "Person" 1312a. As seen in FIG. 19, the developer may choose "person_identifier" 1314a corresponding to column header "Person Identifier" 1306c as the primary identifier for node "Person" 1312a.

Figure 20:
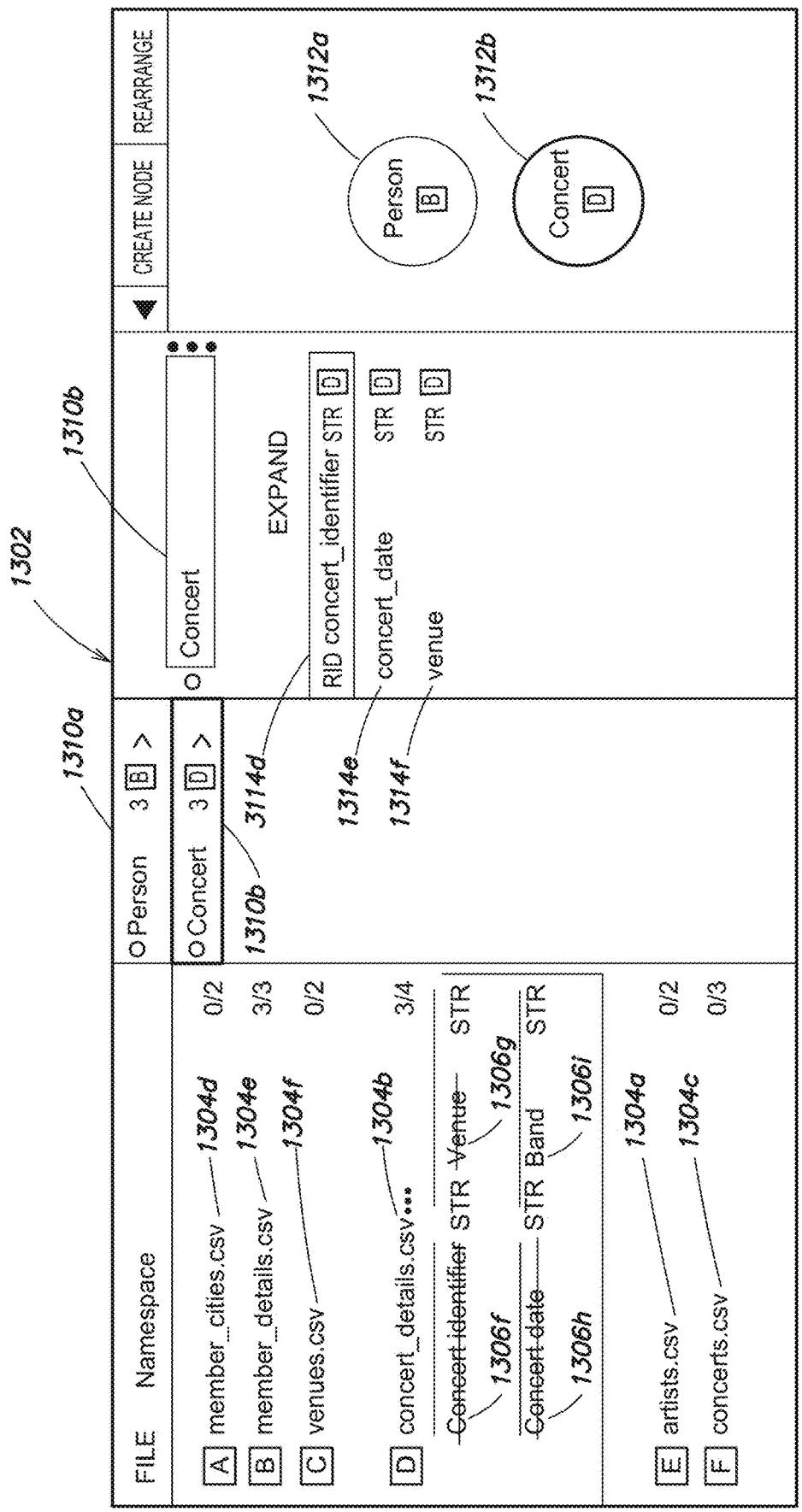

FIG. 20 illustrates creation of node "Concert" 1312b using Graphitect. The developer may create node "Concert" 1312b. In this case, as shown in FIG. 20, the developer decides that "Concert Identifier" 1306f, "Concert date" 1306h, and "Venue" 1306g from .csv file 1104b represented as "concerts_details.cv" 1304b in GUI 1302 can be added as attributes (e.g., "concert_identifier" 1314d, "concert_date" 1314e, and "venue" 1314f) to node "Concert" 1312b.

Figure 21:
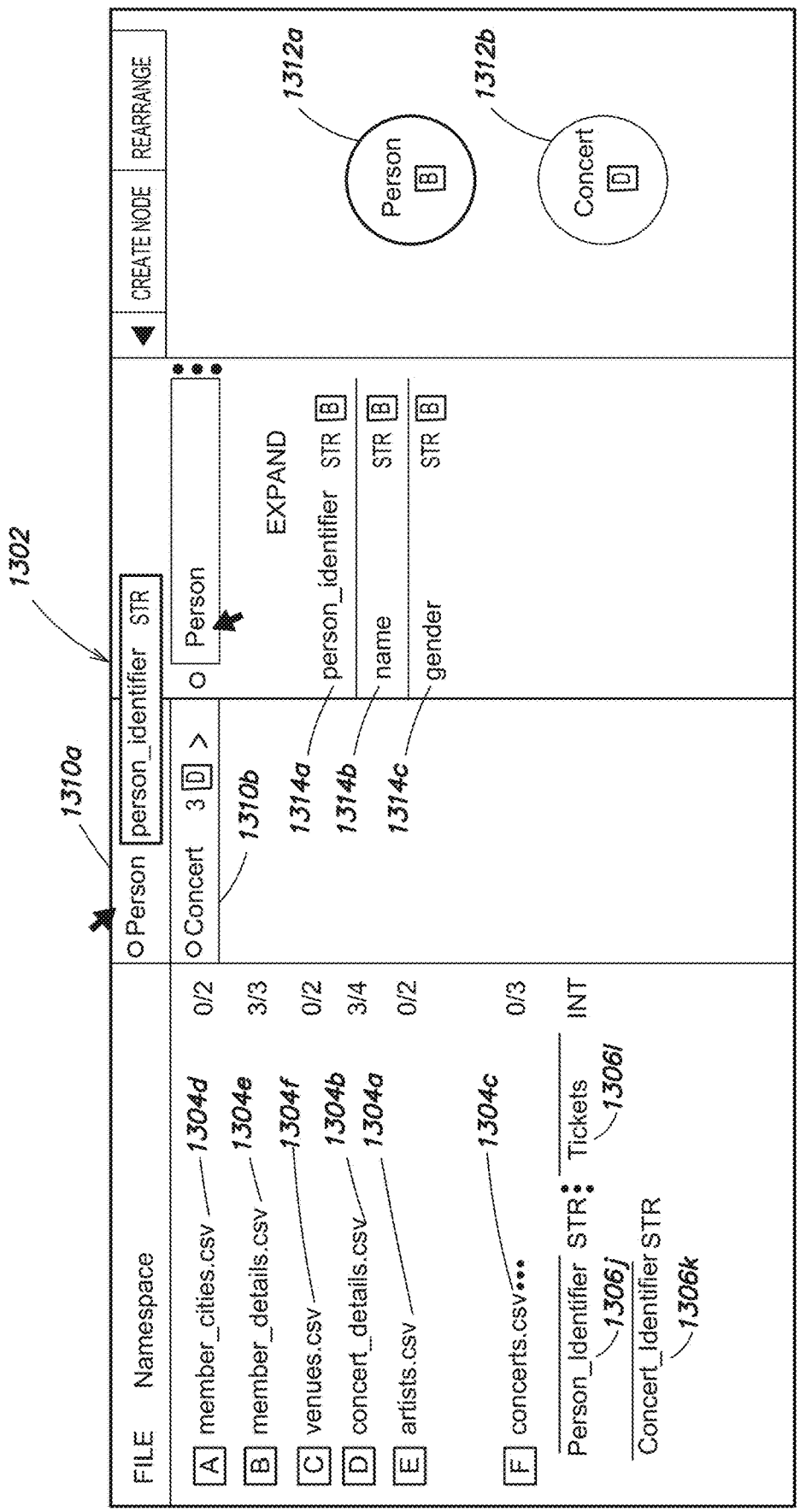
Figure 22:
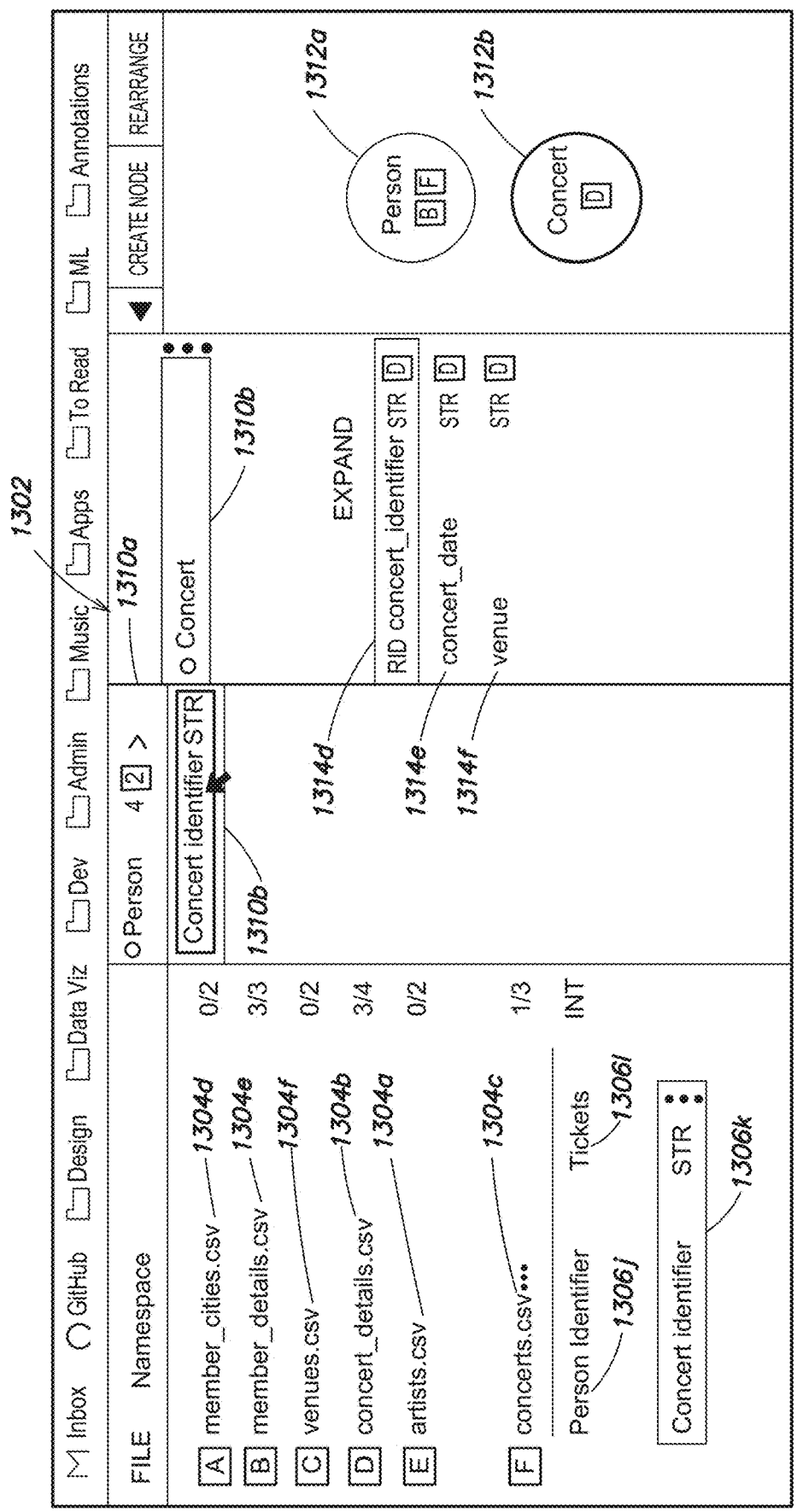

As shown in FIG. 21, the developer may decide that "Person Identifier" 1306j from .csv file 1104c represented as "concerts .csv" 1304c in GUI 1302 can be added as another attribute to node "Person" 1312a. As shown in FIG. 22, the developer may decide that "Concert Identifier" 1306k from .csv file 1104c represented as "concerts .csv" 1304c in GUI 1302 can be added as another attribute to node "Concert" 1312b.

Figure 23:
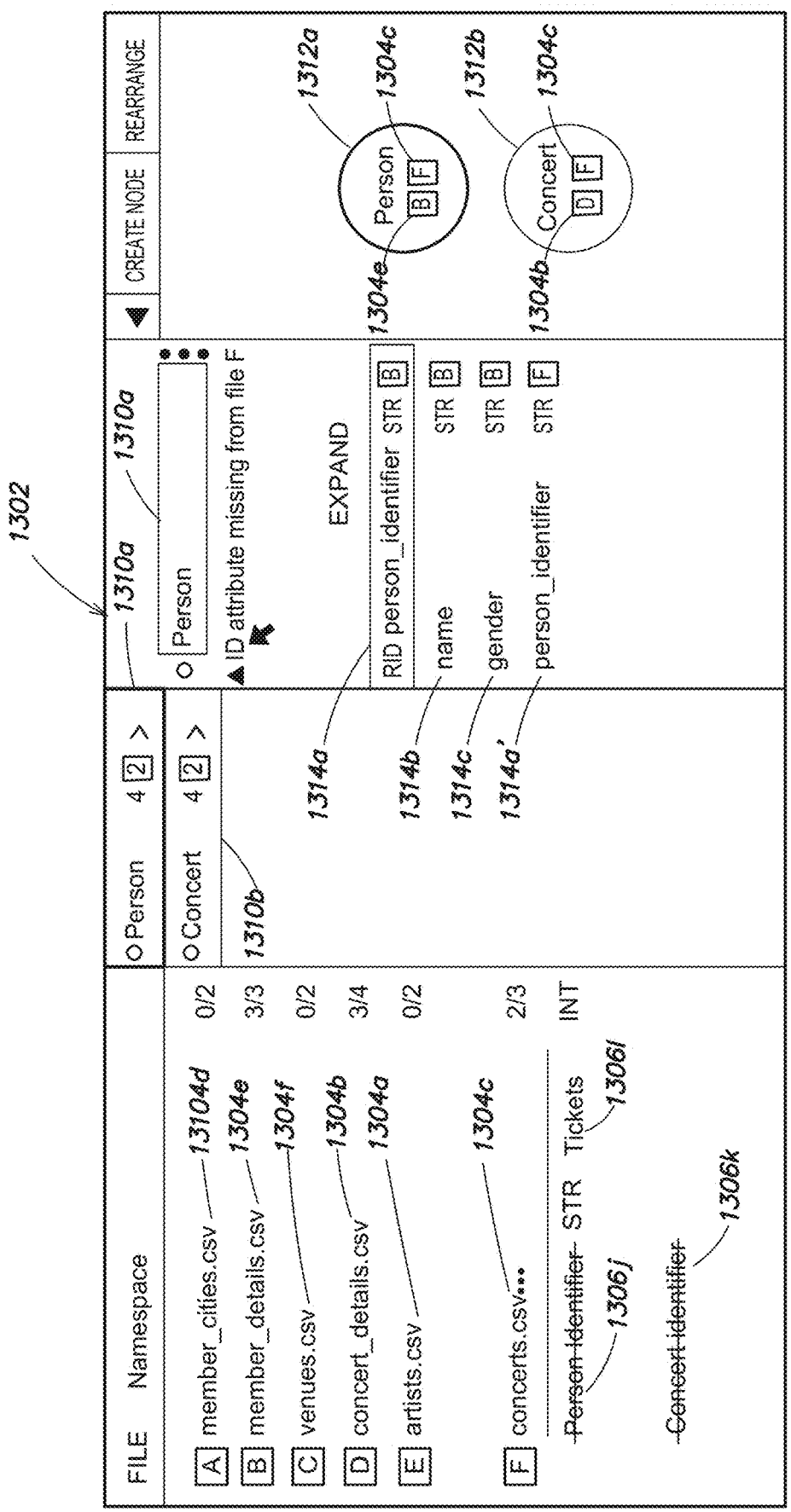

As seen in FIG. 23, both node "Person" 1312a and node "Concert" 1312b draws data from the .csv file 1104c represented as "concerts .csv" 1304c in GUI 1302. As indicated in FIG. 21 and FIG. 22, "Person Identifier" 1306j from "concerts .csv" 1304c is added as an attribute to node "Person" 1312a and "Concert identifier" 1306k from "concerts .csv" 1304c is added as an attribute to node "Concert" 1312b. Therefore, both these nodes include attributes that are drawn from the same .csv file 1104 (i.e. .csv file 1104c).

The .csv files from which attributes are drawn are also represented in the circles representing node "Person" 1312a and node "Concert" 1312b. For example, node "Person" 1312a includes attributes drawn from "member_details.csv" 1304e (see FIG. 18 and FIG. 19). Node "Person" 1312a also includes attributes drawn from "concerts .csv" 1304c (see FIG. 21). Similarly, node "Concert" 1312b includes attributes drawn from "concerts_details.csv" 1304b (see FIG. 20). Node "Concert" 1312b also includes attributes drawn from "concerts .csv" 1304c (see FIG. 22).

Figure 24:
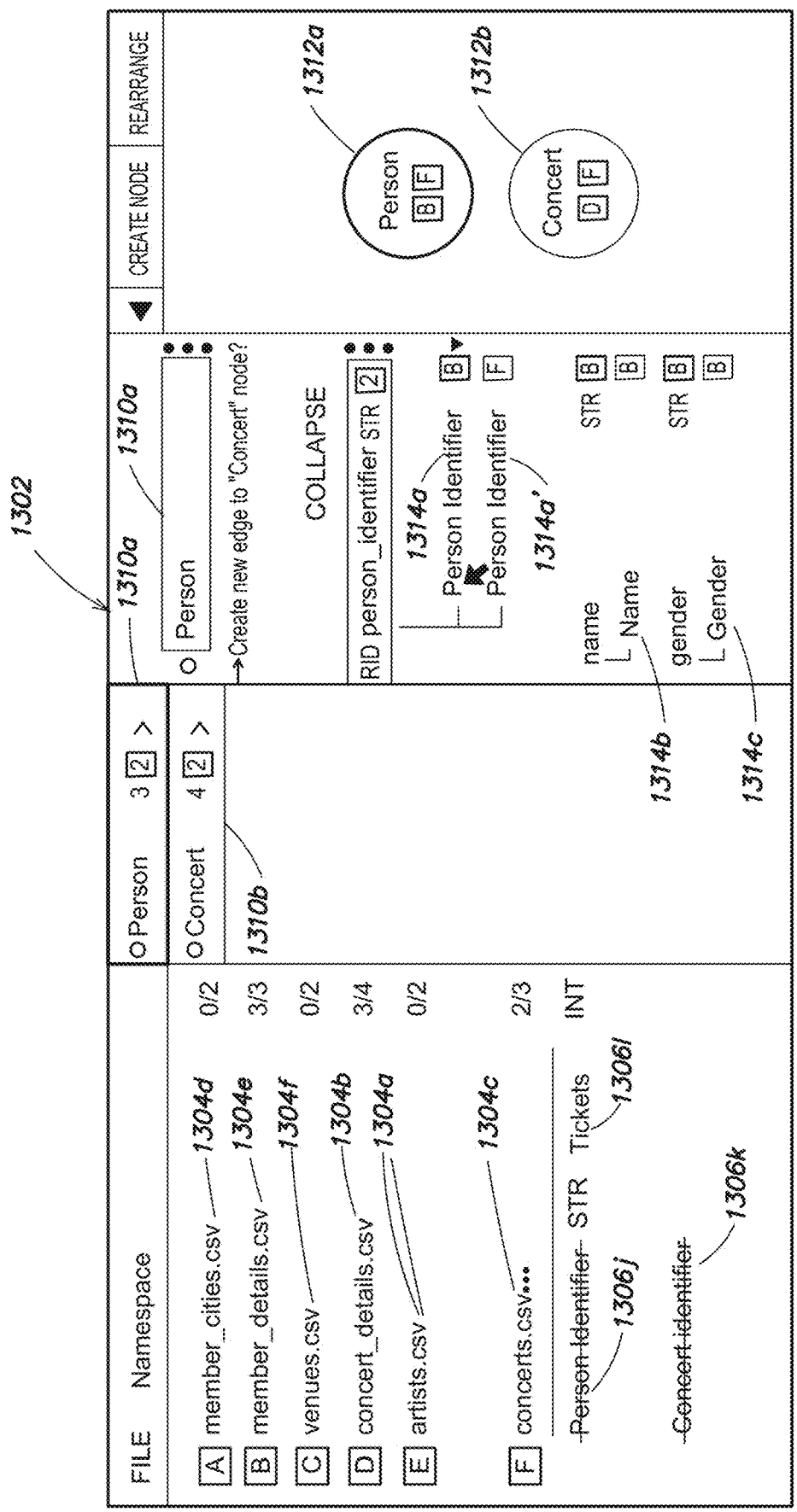

FIG. 24 illustrates that the developer can decide to merge two or more attributes. Graphitect makes note of the fact that the merged attributes are one and the same. For example, the developer may choose to merge "Person Identifier" 1306c from .csv file 1104e represented as "members_details.csv" 1304e in GUI 1302 and "Person Identifier" 1306j from .csv file 1104c represented as "concerts .csv" 1304c in GUI 1302 (seen in FIG. 24 as Person Identifier 1314a and Person Identifier 1314a' respectively).

Figure 25:
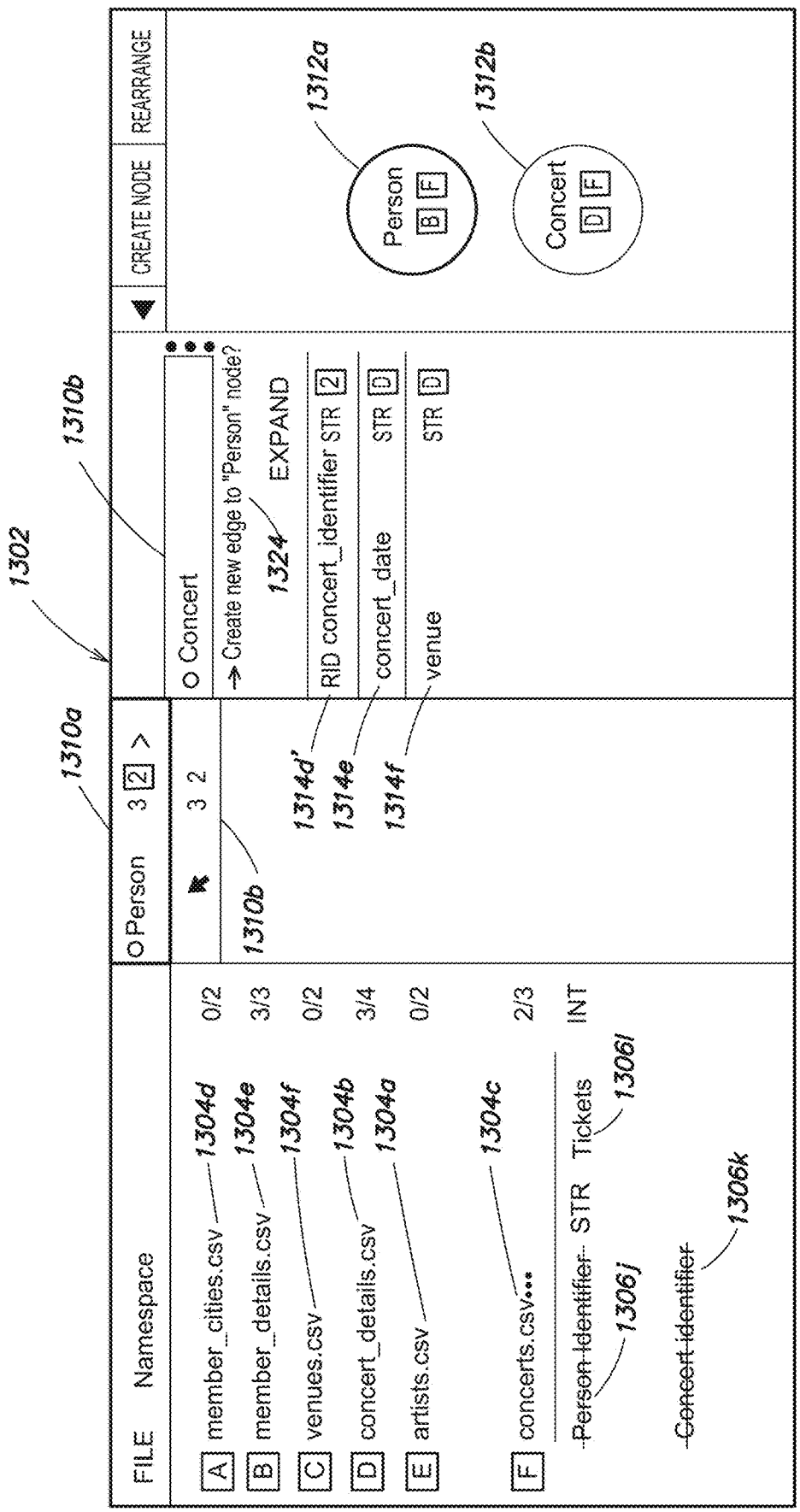

This process can be repeated for "Concert Identifier" 1306f from "concert_details.csv" 1304b and "Concert Identifier" 1306k from "concerts .csv" 1304c. The merged attribute is represented as "concert_identifier" 1314d" in FIG. 25. Graphitect having identified that two nodes (i.e., node "Person" 1312a and node "Concert" 1312b) have at least one attribute each (i.e., "Person Identifier" 1306j and "Concert Identifier" 1306k) from the same file in the concert dataset (i.e., .csv file 1104c represented as "concerts .csv" 1304c) recommends that the two nodes be connected with an edge (as seen as 1324 in GUI 1302). Put differently, Graphitect recommends linking two nodes (e.g., node "Person" 1312a and node "Concert" 1312b) if at least one attribute (e.g., "Person Identifier" 1306j) of a first node (e.g., node "Person" 1312a) and at least one attribute (e.g., "Concert Identifier" 1306k) of a second node (e.g., node "Concert" 1312b) are present in the same file (e.g., .csv file 1104c).

Figure 26:
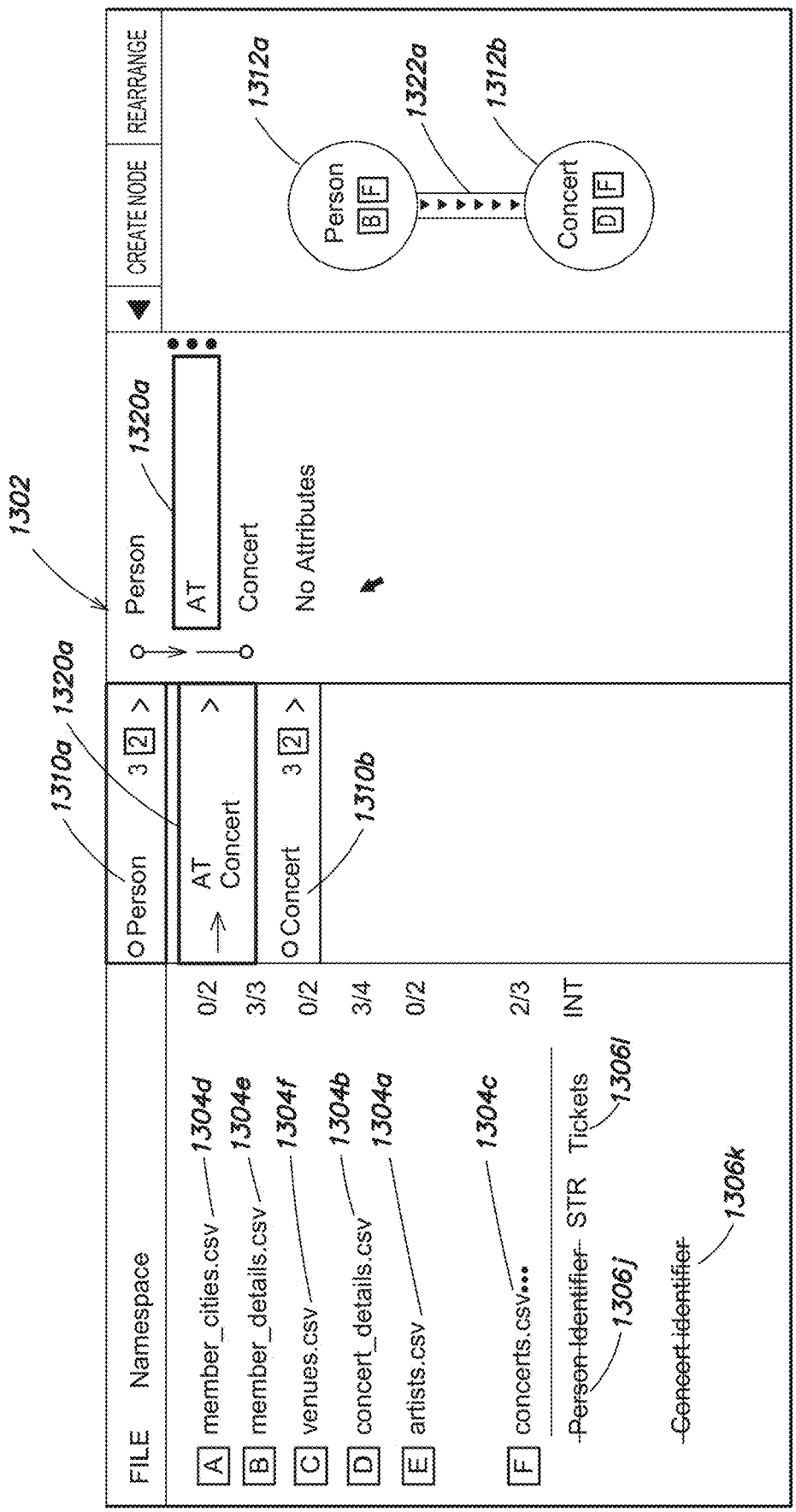

FIG. 26 illustrates creation of an edge between node "Person" 1312a and node "Concert" 1312b in Graphitect. Thus, as seen in FIG. 26 the developer may connect node "Person" 1312a and node "Concert" 1312b with an "AT" edge 1322a to semantically represent "Person AT Concert."

Figure 27:
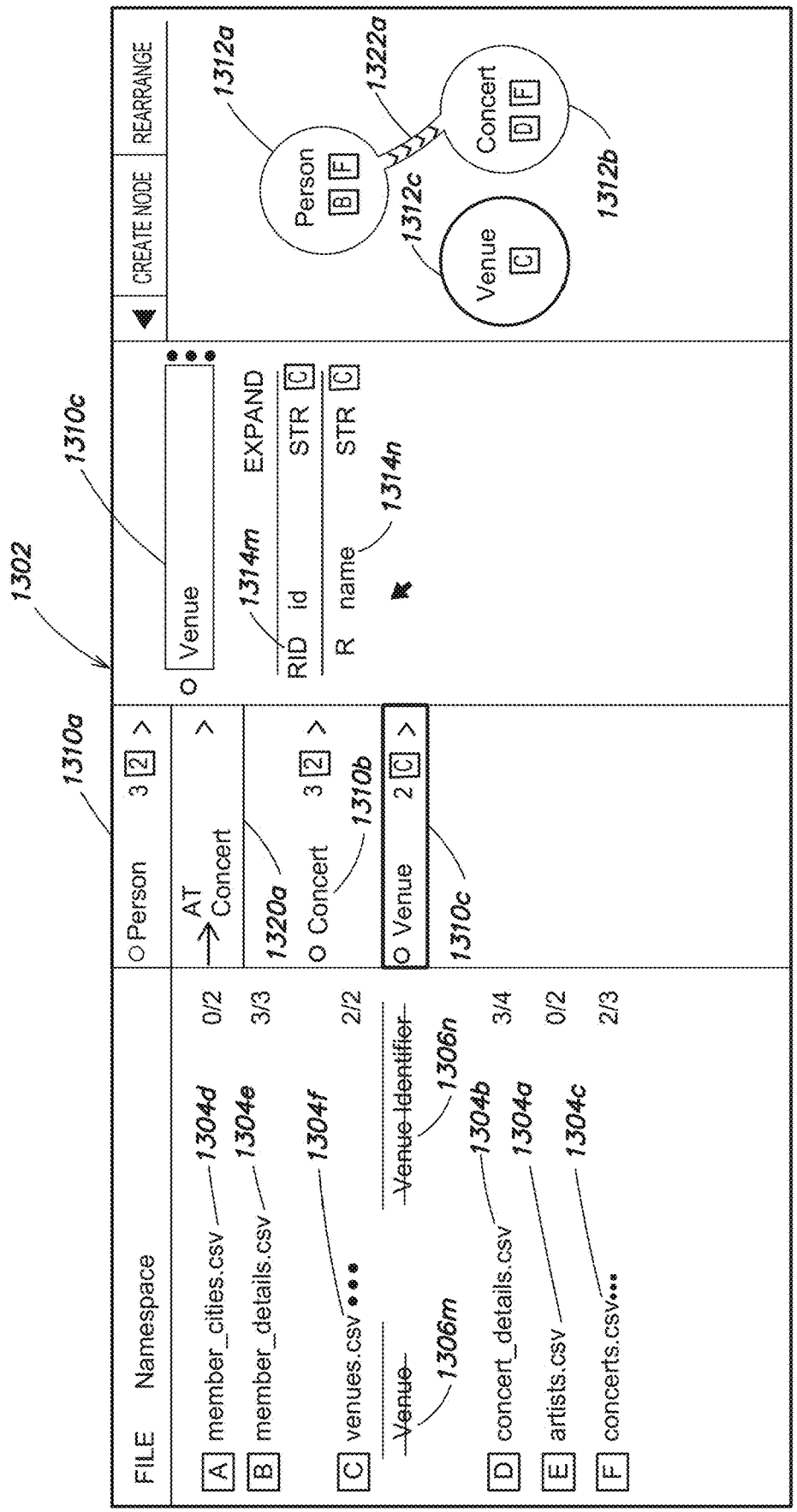

FIG. 27 illustrates creation of a node "Venue" 1312c using Graphitect. In a manner similar to creation of node "Person" 1312a and node "Concert" 1312b, the developer may determine that creation of node "Venue" 1312c may be useful for querying and discovering relationships within the data. As shown in FIG. 27, the developer may add columns with column header "Venue" 1306m and "Venue Identifier" 1306n from .csv file 1104f represented as "venues .csv" 1304f as attributes (renamed as "id" 1314m and "name" 1314n respectively) to node "Venue" 1312c.

Figure 28:
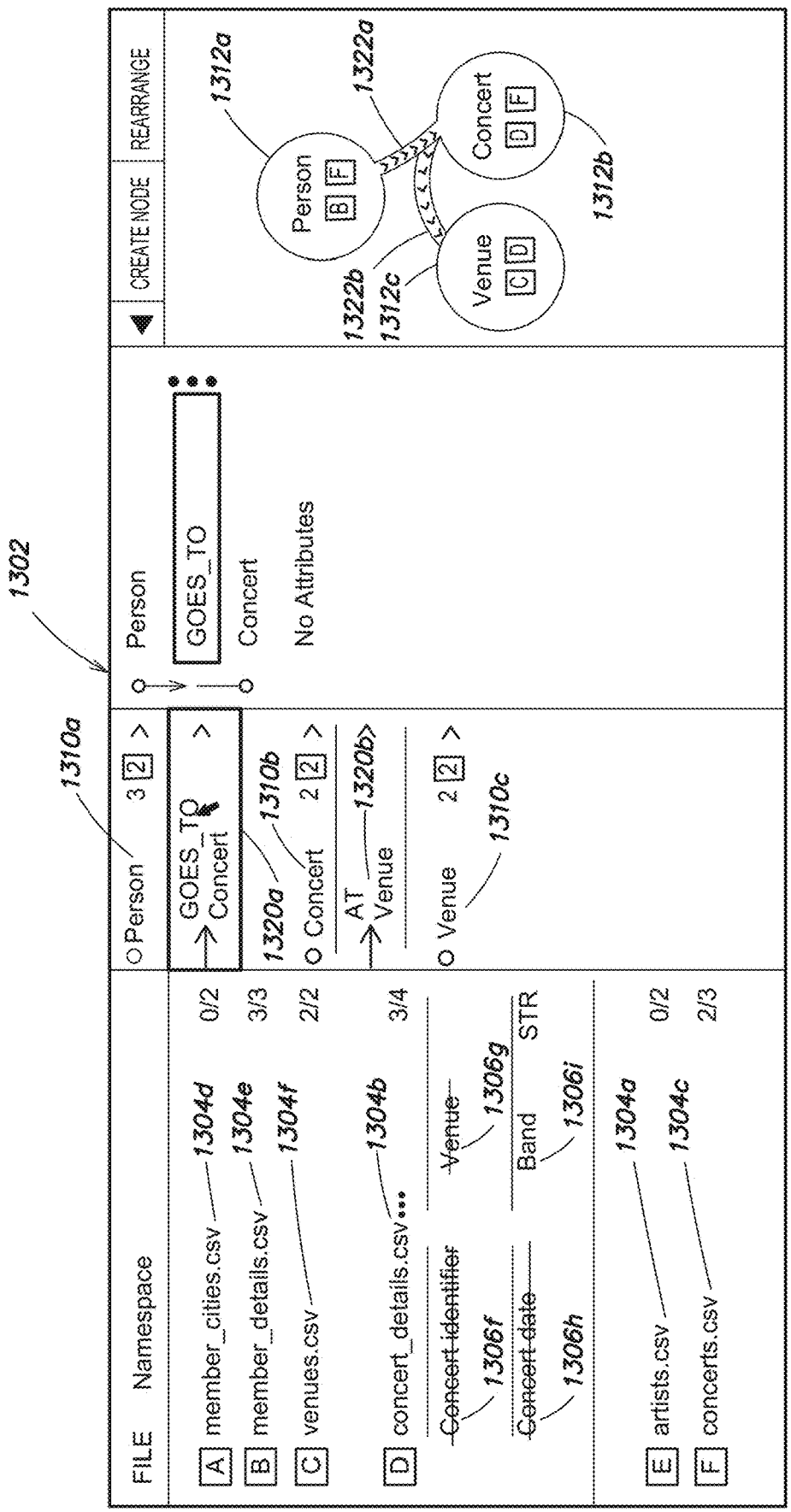

FIG. 28 illustrates creation of an edge connecting node "Venue" 1312c and node "Concert" 1312b using Graphitect. The developer may add column with column header "Venue" 1306g as an attribute to node "Venue" 1312c. Thus, node "Venue" 1312c has one attribute (e.g., "Venue" 1306g) from .csv file 1104b represented as "concerts_details.csv" 1304b. Similarly, node "Concert' 1312b has at least one attribute "Concert Identifier" 1306f from .csv file 1104b represented as "concerts_details.csv" 1304b. Therefore, Graphitect recommends connecting node "Venue" 1312c and node "Concert" 1312b with an edge. In this example, the developer may edit the edge between node "Person" 1312a and node "Concert" 1312b from "AT" to "GOES_TO" 1320a to semantically represent "Person GOES_TO Concert." The developer may create an edge "AT" 1320b between node "Concert" 1310b and "Venue" 1310c to semantically represent "Concert AT Venue."

Figure 29:
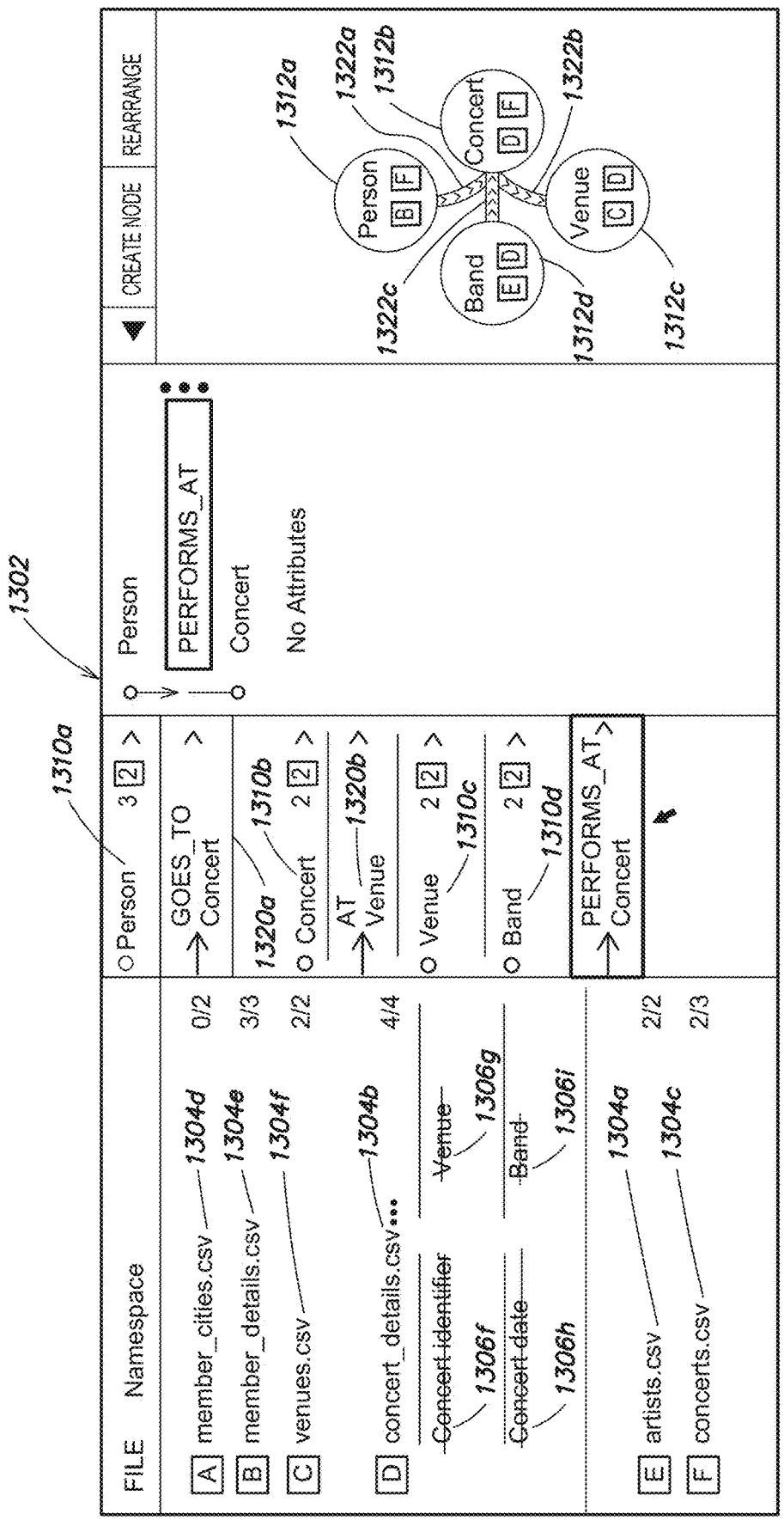

FIG. 29 shows creation of node "Band" 1312d and an edge connecting node "Band" 1312d and node "Concert" 1312b. The creation of node "Band" 1312d and the assignment of attributes is similar to other nodes discussed above. In this example, node "Band" 1312d is connected to node "Concert" 1312b with an edge "PERFORMS_AT" 1320c to semantically represent "Band PERFORMS_AT Concert."

Figure 30:
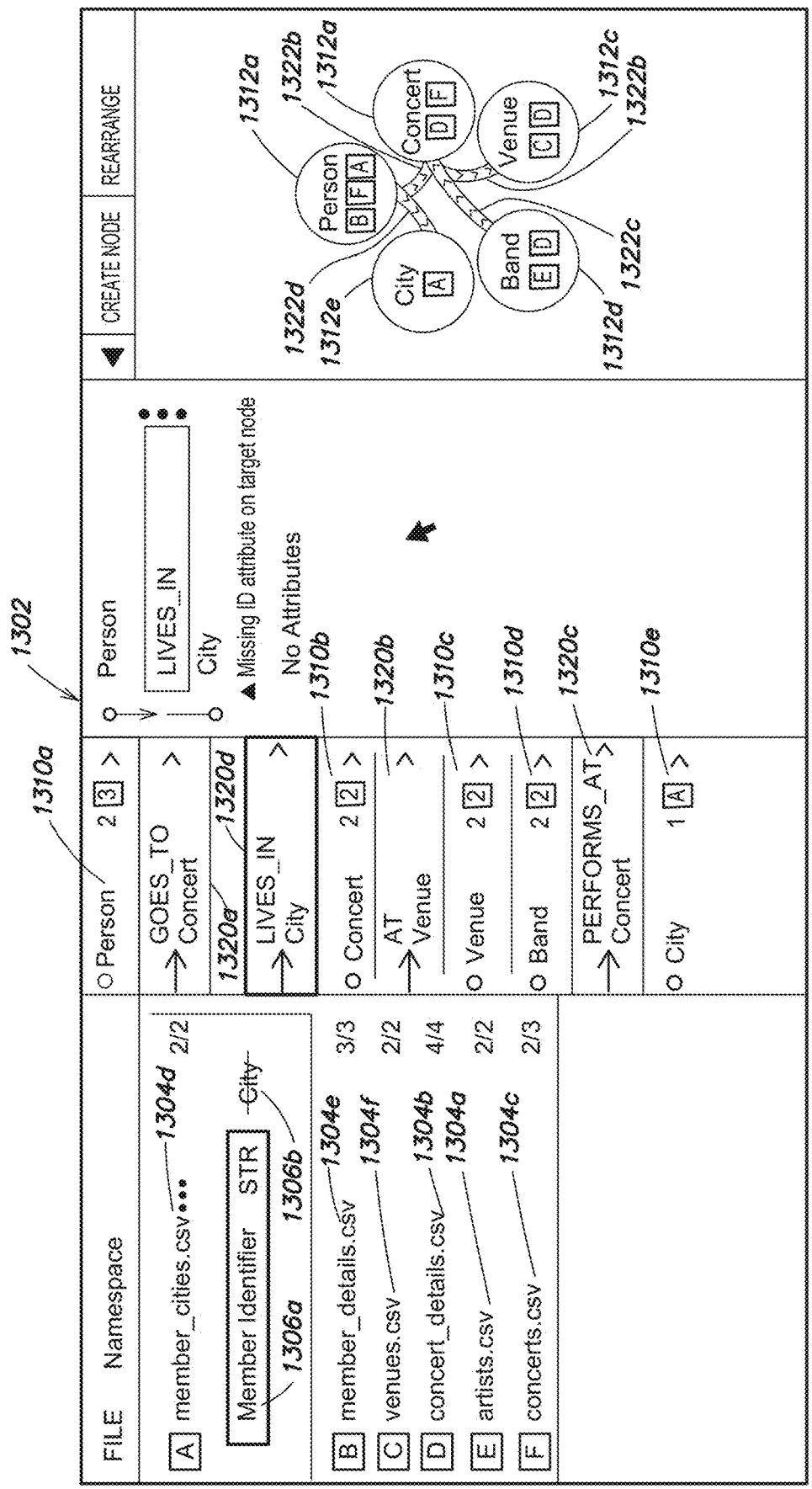

FIG. 30 shows creation of node "City" 1312e and the creation of an edge that connects node "City" 1312e to node "Person" 1312a. In this example, node "Person" 1312a is connected to node "City" 1312e with an edge "LIVES_IN" 1320d to semantically represent "Person LIVES_IN City."

Figure 31:
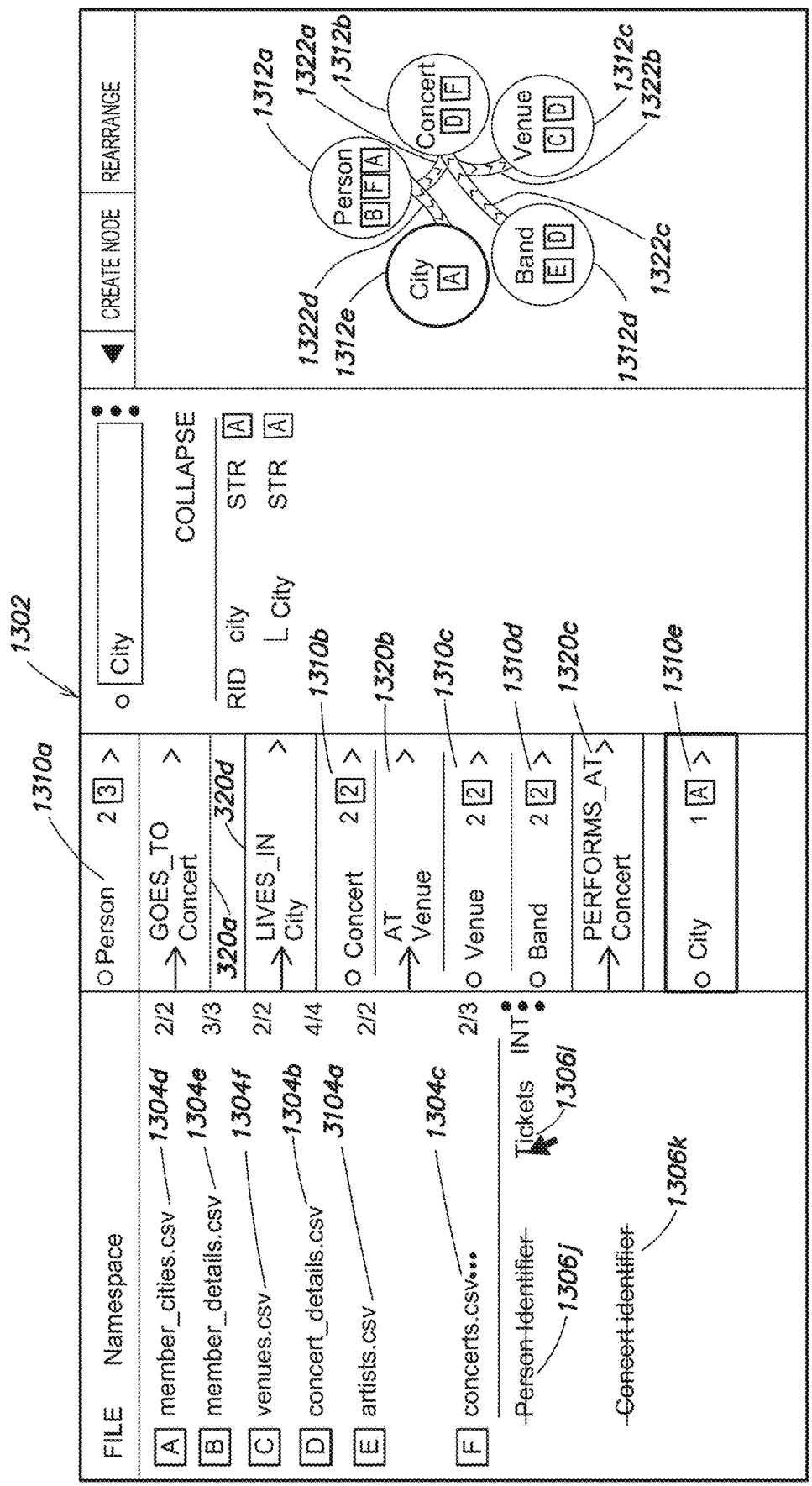

As seen in FIG. 31, column with column header "Tickets" 13061 in .csv 1104c represented as "concerts .csv" 1304c in GUI 1302 is not yet been assigned as a node, attribute, or an edge.

Figure 32:
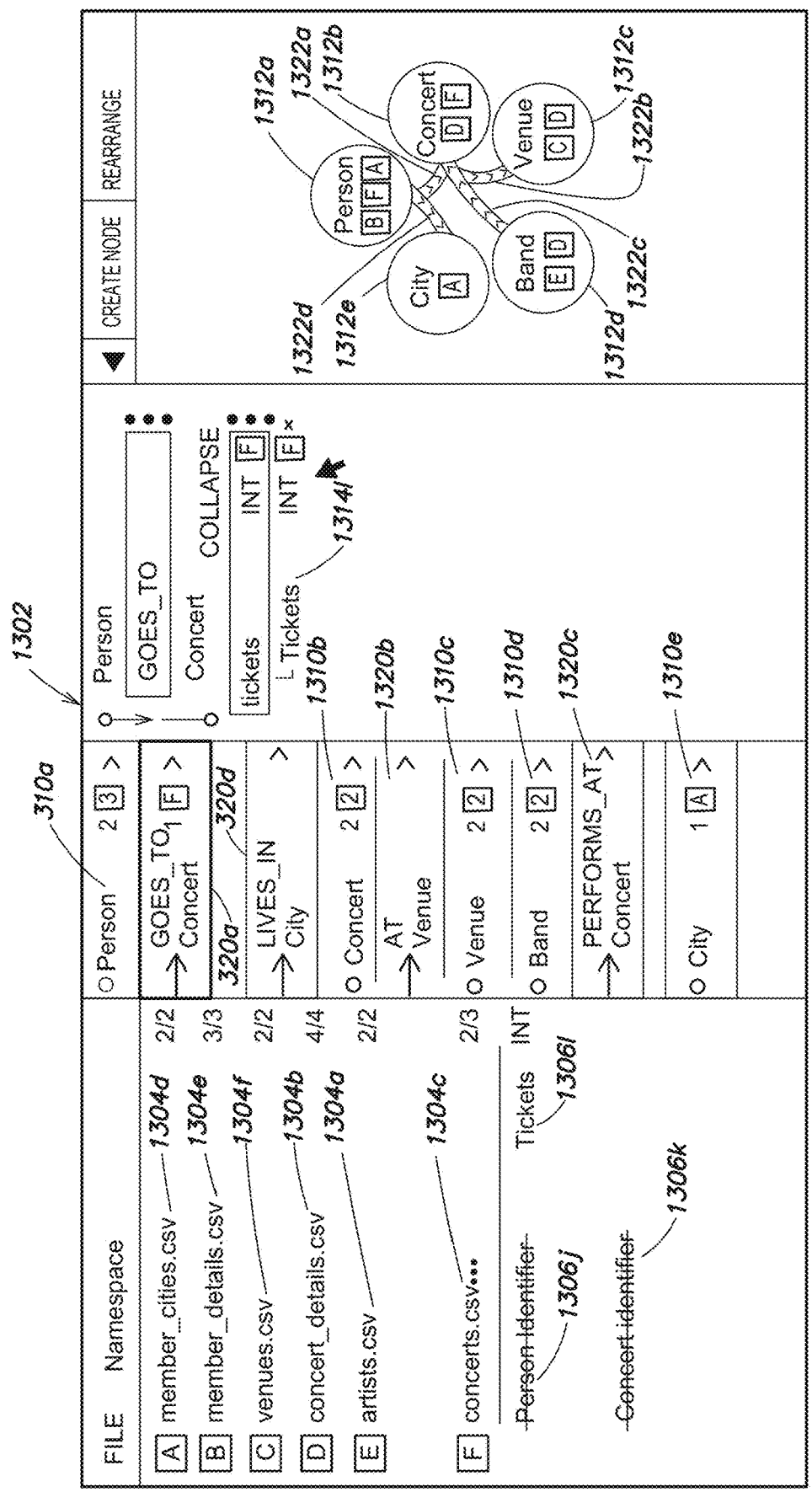
Figure 33:
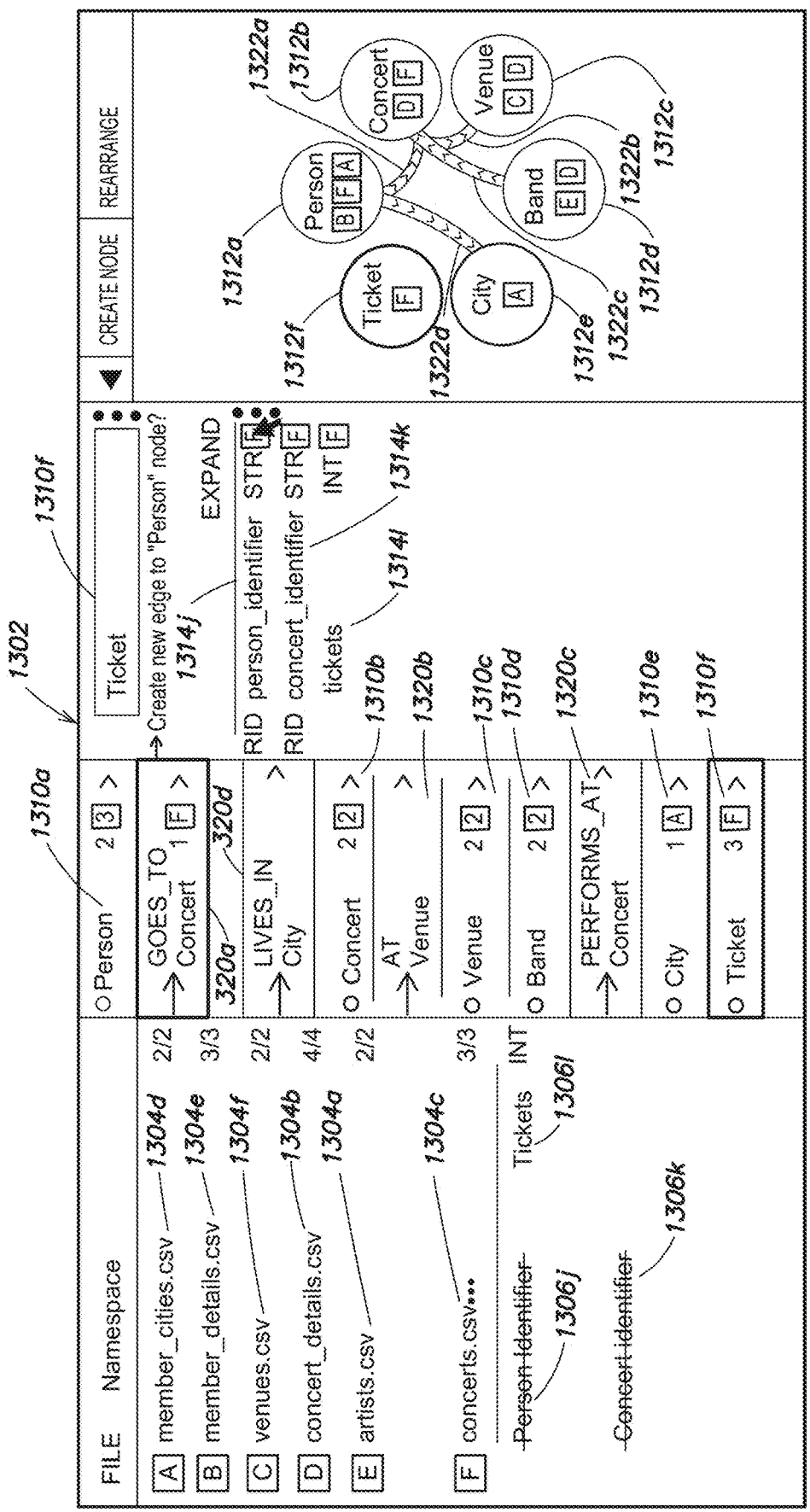
Figure 34:
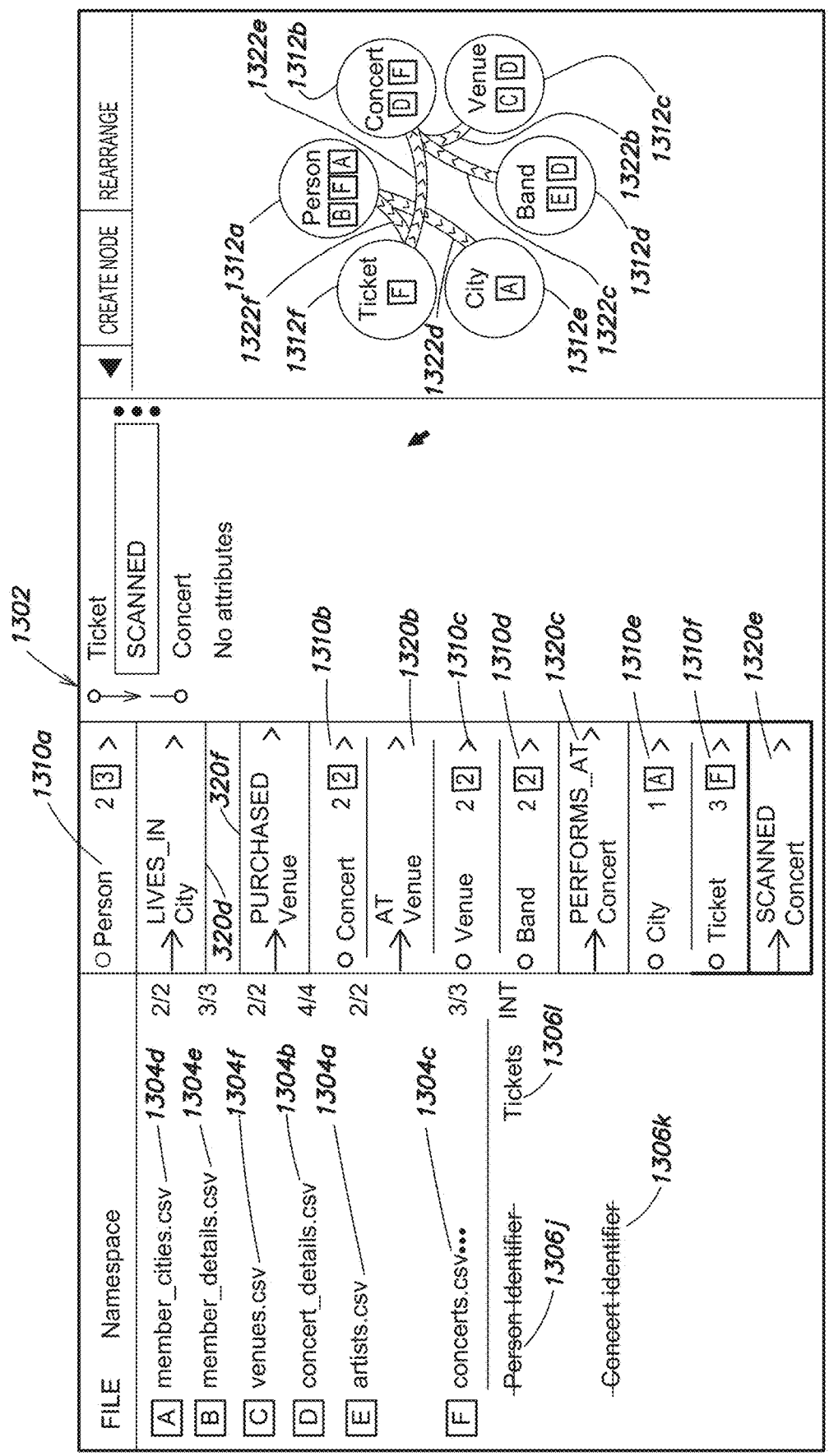

FIGS. 32-34 illustrate two possible ways for ingesting "Tickets" 13061 in .csv file 104c and defining it in the graph structure. In one implementation, the developer may add "Ticket" 13061 as an attribute to edge "GOES_TO" 1320a. Therefore, the edge "GOES_TO" 1320a includes information about the number of tickets that a person bought to a concert (see FIG. 32).

In a second implementation, the developer may add "Tickets" 13061 in .csv file as a node. For instance, in FIG. 33, the developer creates node "Ticket" 1312f. The developer then adds columns with column headers "Person Identifier" 1306j, "Concert Identifier" 1306k, and "Tickets" 13061 from .csv file 1104c represented as "concerts .csv" 1304c in GUI 1302 as attributes of node "Ticket" 1312f (e.g., represented as attributes "person_identifier" 1314j, "concert_identifier" 1314k, and "tickets" 13141 respectively). In one implementation, the developer may define a combination of attributes "person_identifier" 1314j and "concert_identifier" 1314k as the primary identifier to node "Ticket" 1312f. The combination of "person_identifier" 1314j and "concert_identifier" 1314k can form a unique identifier for node "Ticket" 1312f. As shown in FIG. 33, in this example, both "person_identifier" 1314j and "concert_identifier" 1314k are listed as identifiers in Graphitect.

As shown in FIG. 34, node "Person" 1312a, node "Concert" 1312b, and node "Ticket" 1312f include attributes from the same file (i.e., .csv file 1104c represented as "concerts .csv" 1304c in GUI 1302). Therefore, instead of linking node "Person" 1312a with node "Concert" 1312b, node "Ticket" 1312f can be linked with both node "Person" 1312a with node "Concert" 1312b. In this example, the developer may add an edge "PURCHASED" 1320f between node "Person" 1312a and node "Concert" 1312b to semantically represent "Person PURCHASED Ticket". The developer may also add an edge "SCANNED" 1320e between node "Concert" 1312b and node "Ticket" 1312f to semantically represent "Ticket SCANNED at Concert."

FIGS. 32-34 illustrate that the same dataset can have multiple potential graph structures. The example above shows that there are two different ways to visualize the same concert dataset-one with "Ticket" 13061 as an attribute to "GOES_TO" edge and the second with "Ticket" 13061 as a node. Thus, a query to determine if a person bought tickets to a concert can be built by looking at either of the two graph structures (e.g., FIG. 32 or FIG. 34).

Following the creation of the graph structure, Graphitect outputs a configuration file that defines the graph schema.

An example output configuration file for the above example is shown below.

```
{
    "namespace": "Concerts",
    "files": [
        {
            "id": "A",
            "source": {
                "file_name": "member_cities.csv",
                "type": "local"
            },
            "fields": [
                {
                    "id": "hggdqoosh",
                    "name": "Member Identifier",
                    "type": "str",
                    "is_computed": false
                },
                {
                    "id": "xvpwuwm",
                    "name": "City",
                    "type":"str",
                    "is_computed": false
                }
            ]
        },
        {
            "id": "B",
            "source": {
                "file_name": "member_details.csv",
                "type": "local"
            },
            "fields": [
                {
                    "id": "hgesvxmd",
                    "name": "Person Identifier",
                    "type": "str",
                    "is_computed": false
                },
                {
                    "id": "oivibus",
                    "name": "Name",
                    "type": "str",
                    "is_computed": false
                },
                {
                    "id": "kvtrajtj",
                    "name": "Gender",
                    "type": "str",
                    "is_computed": false
                }
            ]
        },
        {
            "id": "C",
            "source": {
                "file_name": "venues.csv",
                "type": "local"
            },
            "fields": [
                {
                    "id": "wmbtoliie",
                    "name": "Venue",
```

```
            "type": "str",
            "is_computed": false
          },
          {
            "id": "hqkdo",
            "name": "Venue Identifier",
            "type": "str",
            "is_computed": false
          }
        ]
      },
      {
        "id": "D",
        "source": {
          "file_name": "concert_details.csv",
          "type": "local"
        },
        "fields": [
          {
            "id": "tnaspnp",
            "name": "Concert identifier",
            "type": "str",
            "is_computed": false
          },
          {
            "id": "foumdlifd",
            "name": "Concert date",
            "type": "str",
            "is_computed": false
          },
          {
            "id": "vgwibfaok",
            "name": "Venue",
            "type": "str",
            "is_computed": false
          },
          {
            "id": "aavfqwkw",
            "name": "Band",
            "type": "str",
            "is_computed": false
          }
        ]
      },
      {
        "id": "E",
        "source": {
          "file_name": "artists.csv",
          "type": "local"
        },
        "fields": [
          {
            "id": "ktjsoqo",
            "name": "Band name",
            "type": "str",
            "is_computed": false
          },
          {
            "id": "cyseqrrg",
            "name": "Band identifier",
            "type": "str",
            "is_computed": false
          }
        ]
      },
      {
        "id": "F",
        "source": {
          "file_name": "concerts.csv",
          "type": "local"
        },
        "fields": [
          {
            "id": "umbrtypt",
            "name": "Person Identifier",
            "type": "str",
            "is_computed": false
          },
          {
            "id": "xgmjmkit",
            "name": "Concert identifier",
            "type": "str",
            "is_computed": false
          },
          {
            "id": "sosakg",
            "name": "Tickets",
            "type": "int",
            "is_computed": false
          }
        ]
      }
    ],
    "nodes": [
      {
        "id": "utcnejwrw",
        "name": "Venue",
        "attributes": [
          {
            "id": "aznlfdb",
            "name": "id",
            "field_ids": [
              "hqkdo",
              "vgwibfaok"
            ],
            "is_id": true,
            "is_required": true,
            "is_computed": false
          },
          {
            "id": "myuv",
            "name": "name",
            "field_ids": [
              "wmbtoliie"
            ],
            "is_id": false,
            "is_required": true,
            "is_computed": false
          }
        ]
      },
      {
        "id": "ryeqgxa",
        "name": "Concert",
        "attributes": [
          {
            "id": "atmedevl",
            "name": "id",
            "field_ids": [
              "tnaspnp",
              "xgmjmkit"
            ],
            "is_id": true,
            "is_required": true,
            "is_computed": false
          },
          {
            "id": "njzpzhski",
            "name": "concert_date",
            "field_ids": [
              "foumdlifd"
            ],
            "is_id": false,
            "is_required": false,
            "is_computed": false
          }
        ]
      },
      {
        "id": "zspusoxlr",
        "name": "Band",
        "attributes": [
          {
            "id": "dhxlpwjfl",
            "name": "id",
            "field_ids": [
              "cyseqrrg",
              "aavfqwkw"
```

```
        ],
        "is_id": true,
        "is_required": true,
        "is_computed": false
      },
      {
        "id": "lqxdsk",
        "name": "band_name",
        "field_ids": [
          "ktjsoqo"
        ],
        "is_id": false,
        "is_required": false,
        "is_computed": false
      }
    ]
  },
  {
    "id": "jlrgxvvmm",
    "name": "Ticket",
    "attributes": [
      {
        "id": "ctxgsssyy",
        "name": "person_identifier",
        "field_ids": [
          "umbrtypt"
        ],
        "is_id": true,
        "is_required": true,
        "is_computed": false
      },
      {
        "id": "mjnhohp",
        "name": "concert_identifier",
        "field_ids": [
          "xgmjmkit"
        ],
        "is_id": true,
        "is_required": true,
        "is_computed": false
      },
      {
        "id": "aybukglv",
        "name": "tickets",
        "field_ids": [
          "sosakg"
        ],
        "is_id": false,
        "is_required": false,
        "is_computed": false
      }
    ]
  },
  {
    "id": "jazhseh",
    "name": "Person",
    "attributes": [
      {
        "id": "huqpjamug",
        "name": "person_identifier",
        "field_ids": [
          "hgesvxmd",
          "umbrtypt",
          "hggdqoosh"
        ],
        "is_id": true,
        "is_required": true,
        "is_computed": false
      },
      {
        "id": "chltslr",
        "name": "name",
        "field_ids": [
          "oivibus"
        ],
        "is_id": false,
        "is_required": false,
        "is_computed": false
      },
      {
        "id": "xzxlqsnpr",
        "name": "gender",
        "field_ids": [
          "kvtrajtj"
        ],
        "is_id": false,
        "is_required": false,
        "is_computed": false
      }
    ]
  },
  {
    "id": "lfuxxoo",
    "name": "City",
    "attributes": [
      {
        "id": "tnbplzgw",
        "name": "city",
        "field_ids": [
          "xvpwuwm"
        ],
        "is_id": true,
        "is_required": true,
        "is_computed": false
      }
    ]
  }
],
"edges": [
  {
    "id": "gwxjlp",
    "name": "AT",
    "source_node_id": "ryeqgxa",
    "target_node_id": "utcnejwrw",
    "attributes": []
  },
  {
    "id": "ncdggvjti",
    "name": "PERFORMS_AT",
    "source_node_id": "zspusoxlr",
    "target_node_id": "ryeqgxa",
    "attributes": []
  },
  {
    "id": "eyudgrj",
    "name": "LIVES_IN",
    "source_node_id": "jazhseh",
    "target_node_id": "lfuxxoo",
    "attributes": []
  },
  {
    "id": "tezifiojy",
    "name": "PURCHASED",
    "source_node_id": "jazhseh",
    "target_node_id": "jlrgxvvmm",
    "attributes": []
  },
  {
    "id": "bjdbezjhd",
    "name": "SCANNED",
    "source_node_id": "jlrgxvvmm",
    "target_node_id": "ryeqgxa",
    "attributes": []
  }
],
"connections": []
}
```

FIG. 35 illustrates an example Python code to generate one or more graph files (in appropriate graph-specific file format). The output of Graphitect is a configuration file that defines the graph schema. The Python script illustrated in FIG. 35 takes the path to the configuration file output from Graphitect as an argument. The Python script also includes a reference to a directory that contains the dataset that is imported into Graphitect. (e.g., .csv files- .csv 1104 files in the previous example). This Python script creates one or more intermediate graph files (in appropriate graph-specific format) for that particular namespace. For example, the Python script may create a file that defines the nodes for a namespace and another file that defines the edges for the namespace such that these files can be imported to a graph database management system such as Neo4j. In this manner, the subgraph for a namespace can be rendered in Neo4j.

The example detailed above is presented primarily for illustrative purposes. Graphitect can be employed on different types of datasets that include one or more structured fields. Graphitect is domain agnostic. For instance, Graphitect can be used to define graph schemas for datasets belonging to domains such as health care, finance, insurance, e-commerce, entertainment, law, sports, social media, transportation, energy resources and consumption, climate science, education, agriculture, housing, immigration, and other scientific/academic endeavors.

For creating RKG and ingesting new datasets to RKG, Graphitect can be a part of a workflow/pipeline that automatically creates graph schemas for each namespace so as to ultimately merge the respective subgraphs into RKG.

Employing Graphitect can drastically reduce the time for creating graph schemas and ultimately using the graph schemas to visualize the respective graphs. Graphitect also eliminates the need to manually code the graph schema thereby eliminating the need for code development, deployment, and code testing. Graphitect can be employed on any type of dataset including one of more structured fields of any size.

Examples

Examples that May be Implemented According to Some Embodiments Include the Following 1. A data storage and retrieval system for a computer memory, the system comprising:
  means for configuring said memory according to a Roam Knowledge Graph (RKG), the RKG comprising:
    a first subgraph including a first plurality of nodes and at least one first subgraph edge connecting two nodes of the first plurality of nodes, the first subgraph representing a first dataset according to a first graph schema, the first dataset being logically stored in a first namespace of the computer memory;
    a second subgraph including a second plurality of nodes, the second subgraph representing a second dataset according to a second graph schema, the second dataset begin logically stored in a second namespace of the computer memory different from the first namespace;
    a canonical layer logically stored in a third namespace of the computer memory, the canonical layer including a plurality of canonical nodes, each canonical node of the plurality of canonical nodes being unique and found only once in the canonical layer;
    at least one first linking edge between the canonical layer and the first subgraph, the at least one first linking edge connecting a first canonical node of the plurality of canonical nodes and a corresponding first subgraph node of the first plurality of nodes in the first subgraph; and
    at least one second linking edge between the canonical layer and the second subgraph, the at least one second linking edge connecting a second canonical node of the plurality of canonical nodes and a corresponding first subgraph node of the second plurality of nodes in the second subgraph,
    wherein there are no linking edges between the first subgraph and the second subgraph to directly connect any node of the first plurality of nodes in the first subgraph and any node of the second plurality of nodes in the second subgraph, such that the only connections between the first subgraph and the second subgraph are via the canonical layer.

The System of Claim 1, Further Comprising:
2. The system of Example 1, further comprising:
  at least one third linking edge between the canonical layer and the second subgraph, the at least one third linking edge connecting the first canonical node of the plurality of canonical nodes and a corresponding second subgraph node of the second plurality of nodes in the second subgraph, such that the first canonical node is connected to both of the corresponding first subgraph node of the first plurality of nodes in the first subgraph and the corresponding second subgraph node of the second plurality of nodes in the second subgraph.

3. The system of Example 1, further comprising:
  at least one canonical layer edge connecting at least one of the first canonical node or the second canonical node of the plurality of canonical nodes in the canonical layer with at least one other canonical node of the plurality of canonical nodes in the canonical layer.

4. The system of Example 1, wherein:
  the at least one first subgraph edge represents a first relationship between the two nodes of the first plurality of nodes, the first relationship having a first relationship type;
  the at least one first subgraph edge has a first edge type corresponding to the first relationship type; and
  the first edge type is based on at least one of:
    at least one attribute of at least one of the two nodes;
    a plurality of relationships between respective entities of a first plurality of entities specified by first information in the first dataset; or
    at least one trained model that predicts the first relationship type with a corresponding probability.

5. The system of Example 1, wherein:
  the RKG is a graph representation of electronic information pertaining to at least one domain of activity and/or knowledge; and
  the at least one domain comprises one of health care, finance, insurance, e-commerce, entertainment, law, sports, social media, transportation, energy resources and consumption, climate science, education, agriculture, housing, immigration, a scientific endeavor or an academic endeavor.

6. The system of Example 5, wherein:
  the at least one domain comprises health care; and
  the electronic information represented by the RKG pertains to at least one of:
    study, diagnoses, treatment, mitigation, and/or prevention of ailments and diseases;
    forms and techniques of care;
    administration of drugs;
    formulation of new drugs, new diagnoses and new treatments;
    genes and phenotypic expression;
    specializations and credentialing for health care practitioners;
    health care economics, insurance and regulation; or
    patient demographics.

7. The system of Example 1, wherein the first dataset and the second dataset are heterogenous datasets.

8. The system of Example 1, wherein:
the first dataset is from a first source;
the first namespace has a first namespace label that identifies the first source;
the second dataset is from a second source different from the first source; and
the second namespace has a second namespace label that identifies the second source.

9. The system of Example 8, wherein at least one of the first source or the second source is:
a business entity;
an academic institution;
a research organization;
a government agency;
a non-profit organization;
a news outlet; or
an individual.

10. The system of Example 8, wherein:
the first dataset and the second dataset pertain to a health care domain; and
at least one of the first dataset or the second dataset pertaining to the health care domain includes:
a public health database;
an adverse event database;
regulatory documents;
insurance company policy documents;
electronic medical records;
patient surveys;
insurance claims;
Medical Science Liaison (MSL) notes;
Medical Information Requests (MIRs); or
a medical ontology.

11. The system of Example 10, wherein the first dataset and the second dataset are heterogenous datasets.

12. The system of Example 11, wherein at least one of the first dataset and the second dataset includes structured data or semi-structured data.

13. The system of Example 1, wherein at least one of the first dataset and the second dataset includes structured data or semi-structured data.

14. The system of Example 13, wherein:
the at least one of the first dataset and the second dataset comprises at least one file representing at least one database table with a plurality of rows and a plurality of columns; and
the at least one database table includes the structured data or the semi-structured data.

15. The system of Example 14, wherein the at least one database table includes at least one row header and/or at least one column header denoting at least one entity to which the structured data or semi-structured data pertains, the at least one entity having an entity type.

16. The system of Example 1, wherein:
the first dataset includes first information relating to a first plurality of entities having a first entity type;
the first plurality of nodes in the first subgraph respectively represent at least some of the first plurality of entities having the first entity type, the first plurality of nodes having a first node type corresponding to the first entity type; and
the at least one first subgraph edge connecting the two nodes of the first plurality of nodes represents a first relationship of a first relationship type between two entities of the first plurality of entities represented by the two nodes, the at least one first subgraph edge having a first edge type corresponding to the first relationship type.

17. The system of Example 16, wherein the first edge type is based on at least one of:
at least one attribute of at least one of the two nodes of the first plurality of nodes;
a plurality of relationships between respective entities of the first plurality of entities specified by the first information in the first dataset; or
at least one trained model that predicts the first relationship type with a corresponding probability.

18. The system of Example 16, wherein the first entity type and the first node type are one of:
a physical/tangible object;
a place or geographical reference;
a concept;
a legal or professional construct;
a product;
a service;
an event;
an occupation or role;
a professional and/or academic credential or specialization;
a publication;
financial information;
demographic information;
statistical information;
health-related information; or
an ontology.

19. The system of Example 16, wherein the first graph schema specifies:
the first node type corresponding to the first entity type;
the first edge type corresponding to the first relationship type; and
a first arrangement of the first plurality of nodes and the at least one first edge in the first subgraph, based at least in part on the first plurality of entities and the first relationship.

20. The system of Example 19, wherein:
each node of the first plurality of nodes in the first subgraph has a plurality of node attributes; and
the plurality of node attributes includes:
a primary node identifier that is unique in the first namespace for the first dataset; and
at least one of:
the first node type; or
a node label that appears in the first subgraph.

21. The system of Example 20, wherein:
each edge of the at least one edge in the first subgraph has a plurality of edge attributes; and
the plurality of edge attributes includes:
a primary edge identifier that is unique in the first namespace for the first dataset; and at least one of:
the first edge type;
an edge label that appears in the first subgraph; or
a probability regarding a certainty of the first edge type.

22. The system of Example 16, wherein:
the second dataset includes second information relating to a second plurality of entities having a second entity type; and
the second plurality of nodes in the second subgraph respectively represent at least some of the second plurality of entities having the second entity type, the second plurality of nodes having a second node type corresponding to the second entity type.

23. The system of Example 22, wherein:
 each canonical node of the plurality of canonical nodes in the canonical layer has one canonical node type of a plurality of canonical node types; and
 the plurality of canonical node types includes at least one of the first node type or the second node type.

24. The system of Example 23, wherein:
 the RKG is a graph representation of electronic information pertaining to at least one domain of activity and/or knowledge; and
 respective canonical node types of the plurality of canonical node types have significance and/or prevalence in the at least one domain of activity and/or knowledge.

25. The system of Example 24, wherein:
 the at least one domain comprises health care; and
 the plurality of canonical node types includes at least one of:
  disease;
  drug;
  FDA device code;
  FDA device name;
  geography;
  health care organization;
  health care professional;
  hospital;
  manufacturer;
  procedure;
  industry event;
  time; or
  specialty.

26. The system of Example 23, wherein a quantity of canonical nodes in the canonical layer is less than a sum of all nodes present in all subgraphs of the RKG.

27. The system of Example 23, wherein:
 each of the at least one first linking edge between the canonical layer and the first subgraph, and the at least one second linking edge between the canonical layer and the second subgraph, represents a linking relationship having a linking relationship type;
 each of the at least one first linking edge and the at least one second linking edge has a linking edge type corresponding to the linking relationship type; and
 the linking edge type and the linking relationship type is one of:
  IS;
  IS_PART_OF;
  CONTAINS;
   INCLUDES;
   IS_INCLUDED_IN;
   ENCOMPASSES; or
   SUBSUMES.

28. The system of Example 27, wherein:
 the first canonical node has the first node type; and
 the second canonical node has the second node type.

29. The system of Example 28, further comprising:
 a third subgraph including a third plurality of nodes, the third subgraph representing a third dataset according to a third graph schema, the third dataset begin logically stored in a third namespace of the computer memory, wherein:
 the third dataset includes third information relating to a third plurality of entities having the first entity type; and
 the third plurality of nodes in the third subgraph respectively represent at least some of the third plurality of entities having the first entity type, the third plurality of nodes having the first node type corresponding to the first entity type.

30. The system of Example 29, further comprising:
 at least one third linking edge between the canonical layer and the third subgraph, the at least one third linking edge connecting the first canonical node of the plurality of canonical nodes and a corresponding first subgraph node of the third plurality of nodes in the third subgraph, such that the first canonical node is connected to both of the corresponding first subgraph node of the first plurality of nodes in the first subgraph and the corresponding first subgraph node of the third plurality of nodes in the third subgraph.

31. The system of Example 30, further comprising:
 a first canonical layer edge connecting at least one of the first canonical node or the second canonical node of the plurality of canonical nodes with a third canonical node of the plurality of canonical nodes.

32. The system of Example 31, wherein:
 the first canonical layer edge represents a second relationship having a second relationship type;
 the first canonical layer edge has a second edge type corresponding to the second relationship type; and
 the second edge type of the first canonical layer edge is based on at least one of:
  at least one attribute of at least one of the first canonical node, the second canonical node or the third canonical node;
  a plurality of first entity relationships between respective entities of the first plurality of entities, the second plurality of entities, or the third plurality of entities specified by at least one of the first information in the first dataset, the second information in the second dataset, or the third information in the third dataset; or
  at least one first trained model that predicts the second relationship type with a corresponding probability.

33. The system of Example 32, wherein the first edge type of the at least one first subgraph edge is based on at least one of:
 at least one attribute of at least one of the two nodes of the first plurality of nodes;
 a plurality of second entity relationships between respective entities of the first plurality of entities specified by the first information in the first dataset; or
 at least one second trained model that predicts the first relationship type with a corresponding probability.

34. The system of any of Example 1 through 4 and 7 through 33, wherein:
 the RKG is a graph representation of electronic information pertaining to at least one domain of activity and/or knowledge;
 the at least one domain comprises health care; and
 the electronic information represented by the RKG pertains to at least one of:
  study, diagnoses, treatment, mitigation, and/or prevention of ailments and diseases;
  forms and techniques of care;
  administration of drugs;
  formulation of new drugs, new diagnoses and new treatments;
  genes and phenotypic expression;
  specializations and credentialing for health care practitioners;
  health care economics, insurance and regulation; or
  patient demographics.

35. A method for storing and retrieving data in a computer memory, the method comprising:
configuring said memory according to a Roam Knowledge Graph (RKG), the RKG comprising:
a first subgraph including a first plurality of nodes and at least one first subgraph edge connecting two nodes of the first plurality of nodes, the first subgraph representing a first dataset according to a first graph schema, the first dataset being logically stored in a first namespace of the computer memory;
a second subgraph including a second plurality of nodes, the second subgraph representing a second dataset according to a second graph schema, the second dataset begin logically stored in a second namespace of the computer memory different from the first namespace;
a canonical layer logically stored in a third namespace of the computer memory, the canonical layer including a plurality of canonical nodes, each canonical node of the plurality of canonical nodes being unique and found only once in the canonical layer;
at least one first linking edge between the canonical layer and the first subgraph, the at least one first linking edge connecting a first canonical node of the plurality of canonical nodes and a corresponding first subgraph node of the first plurality of nodes in the first subgraph; and
at least one second linking edge between the canonical layer and the second subgraph, the at least one second linking edge connecting a second canonical node of the plurality of canonical nodes and a corresponding first subgraph node of the second plurality of nodes in the second subgraph,
wherein there are no linking edges between the first subgraph and the second subgraph to directly connect any node of the first plurality of nodes in the first subgraph and any node of the second plurality of nodes in the second subgraph, such that the only connections between the first subgraph and the second subgraph are via the canonical layer.

36. A method for storing and retrieving data in a computer memory, the method comprising:
configuring said memory according to a Roam Knowledge Graph (RKG), the RKG comprising:
a first subgraph including a first plurality of nodes and at least one first subgraph edge connecting two nodes of the first plurality of nodes, the first subgraph representing a first dataset according to a first graph schema, the first dataset being logically stored in a first namespace of the computer memory;
a second subgraph including a second plurality of nodes, the second subgraph representing a second dataset according to a second graph schema, the second dataset begin logically stored in a second namespace of the computer memory different from the first namespace;
a canonical layer logically stored in a third namespace of the computer memory, the canonical layer including a plurality of canonical nodes including at least a first canonical node, a second canonical node, and a third canonical node, each canonical node of the plurality of canonical nodes being unique and found only once in the canonical layer;
at least one canonical layer edge connecting at least one of the first canonical node or the second canonical node of the plurality of canonical nodes in the canonical layer with the third canonical node of the plurality of canonical nodes in the canonical layer;
at least one first linking edge between the canonical layer and the first subgraph, the at least one first linking edge connecting the first canonical node of the plurality of canonical nodes and a corresponding first subgraph node of the first plurality of nodes in the first subgraph;
at least one second linking edge between the canonical layer and the second subgraph, the at least one second linking edge connecting the second canonical node of the plurality of canonical nodes and a corresponding first subgraph node of the second plurality of nodes in the second subgraph; and
at least one third linking edge between the canonical layer and the second subgraph, the at least one third linking edge connecting the first canonical node of the plurality of canonical nodes and a corresponding second subgraph node of the second plurality of nodes in the second subgraph, such that the first canonical node is connected to both of the corresponding first subgraph node of the first plurality of nodes in the first subgraph and the corresponding second subgraph node of the second plurality of nodes in the second subgraph,
wherein:
the first dataset and the second dataset are heterogenous datasets;
each of the first dataset and the second dataset includes structured data or semi-structured data; and
there are no linking edges between the first subgraph and the second subgraph to directly connect any node of the first plurality of nodes in the first subgraph and any node of the second plurality of nodes in the second subgraph, such that the only connections between the first subgraph and the second subgraph are via the canonical layer.

37. The method of Example 36, further comprising:
processing at least one dataset including unstructured data, using at least one machine learning or natural language processing technique, to provide at least some of the structured data or semi-structured data included in at least one of the first dataset and the second dataset.

38. The method of Example 36, wherein:
the first dataset includes first information relating to a first plurality of entities having a first entity type;
the first plurality of nodes in the first subgraph respectively represent at least some of the first plurality of entities having the first entity type, the first plurality of nodes having a first node type corresponding to the first entity type;
the at least one first subgraph edge connecting the two nodes of the first plurality of nodes represents a first relationship of a first relationship type between two entities of the first plurality of entities represented by the two nodes, the at least one first subgraph edge having a first edge type corresponding to the first relationship type; and
the first edge type is based on at least one of:
at least one attribute of at least one of the two nodes of the first plurality of nodes;
a plurality of first entity relationships between respective entities of the first plurality of entities specified by the first information in the first dataset; or
at least one first trained model that predicts the first relationship type with a corresponding probability.

39. The method of Example 38, wherein:
the second dataset includes second information relating to a second plurality of entities having a second entity type; and
the second plurality of nodes in the second subgraph respectively represent at least some of the second plurality of entities having the second entity type, the second plurality of nodes having a second node type corresponding to the second entity type;
the at least one canonical layer edge represents a second relationship having a second relationship type;
the at least one canonical layer edge has a second edge type corresponding to the second relationship type; and
the second edge type of the at least one canonical layer edge is based on at least one of:
  at least one attribute of at least one of the first canonical node, the second canonical node or the third canonical node;
  a plurality of second entity relationships between respective entities of the first plurality of entities or the second plurality of entities specified by at least one of the first information in the first dataset or the second information in the second dataset; or
  at least one second trained model that predicts the second relationship type with a corresponding probability.

40. The method of Example 39, wherein:
the RKG is a graph representation of electronic information pertaining to at least one domain of activity and/or knowledge;
the at least one domain comprises health care; and
the electronic information represented by the RKG pertains to at least one of:
  study, diagnoses, treatment, mitigation, and/or prevention of ailments and diseases;
  forms and techniques of care;
  administration of drugs;
  formulation of new drugs, new diagnoses and new treatments;
  genes and phenotypic expression;
  specializations and credentialing for health care practitioners;
  health care economics, insurance and regulation; or
  patient demographics.

41. The method of Example 40, wherein:
the first dataset is from a first source;
the second dataset is from a second source different from the first source; and
at least one of the first source or the second source is:
  a business entity;
  an academic institution;
  a research organization;
  a government agency;
  a non-profit organization;
  a news outlet; or
  an individual.

42. The method of Example 41, wherein:
the first dataset and the second dataset pertain to the health care domain; and
at least one of the first dataset or the second dataset pertaining to the health care domain includes:
  a public health database;
  an adverse event database;
  regulatory documents;
  insurance company policy documents;
  electronic medical records;
  patient surveys;
  insurance claims;
  Medical Science Liaison (MSL) notes;
  Medical Information Requests (MIRs); or
  a medical ontology.

43. The method of Example 42, wherein the first entity type and the first node type are one of:
  a physical/tangible object;
  a place or geographical reference;
  a concept;
  a legal or professional construct;
  a product;
  a service;
  an event;
  an occupation or role;
  a professional and/or academic credential or specialization;
  a publication;
  financial information;
  demographic information;
  statistical information;
  health-related information; or
  an ontology.

44. The method of Example 43, wherein:
each canonical node of the plurality of canonical nodes in the canonical layer has one canonical node type of a plurality of canonical node types;
the plurality of canonical node types includes at least one of the first node type or the second node type; and
the plurality of canonical node types includes at least one of:
  disease;
  drug;
  FDA device code;
  FDA device name;
  geography;
  health care organization;
  health care professional;
  hospital;
  manufacturer;
  procedure;
  industry event;
  time; or
  specialty.

45. A data storage and retrieval system, comprising:
at least one computer memory; and
at least one processor communicatively coupled to the at least one computer memory, wherein upon execution by the at least one processor of processor-executable instructions, the at least one processor configures the at least one computer memory according to a Roam Knowledge Graph (RKG), the RKG comprising:
  a first subgraph including a first plurality of nodes and at least one first subgraph edge connecting two nodes of the first plurality of nodes, the first subgraph representing a first dataset according to a first graph schema, the first dataset being logically stored in a first namespace of the computer memory;
  a second subgraph including a second plurality of nodes, the second subgraph representing a second dataset according to a second graph schema, the second dataset begin logically stored in a second namespace of the computer memory different from the first namespace;
  a canonical layer logically stored in a third namespace of the computer memory, the canonical layer including a plurality of canonical nodes, each canonical node of the plurality of canonical nodes being unique and found only once in the canonical layer;

at least one first linking edge between the canonical layer and the first subgraph, the at least one first linking edge connecting a first canonical node of the plurality of canonical nodes and a corresponding first subgraph node of the first plurality of nodes in the first subgraph; and at least one second linking edge between the canonical layer and the second subgraph, the at least one second linking edge connecting a second canonical node of the plurality of canonical nodes and a corresponding first subgraph node of the second plurality of nodes in the second subgraph, wherein there are no linking edges between the first subgraph and the second subgraph to directly connect any node of the first plurality of nodes in the first subgraph and any node of the second plurality of nodes in the second subgraph, such that the only connections between the first subgraph and the second subgraph are via the canonical layer.

46. At least one non-transitory computer-readable medium encoded with processor-executable instructions that, when executed by at least one processor, cause the at least one processor to configure at least one computer memory according to a Roam Knowledge Graph (RKG), the RKG comprising:

a first subgraph including a first plurality of nodes and at least one first subgraph edge connecting two nodes of the first plurality of nodes, the first subgraph representing a first dataset according to a first graph schema, the first dataset being logically stored in a first namespace of the computer memory;

a second subgraph including a second plurality of nodes, the second subgraph representing a second dataset according to a second graph schema, the second dataset begin logically stored in a second namespace of the computer memory different from the first namespace;

a canonical layer logically stored in a third namespace of the computer memory, the canonical layer including a plurality of canonical nodes, each canonical node of the plurality of canonical nodes being unique and found only once in the canonical layer;

at least one first linking edge between the canonical layer and the first subgraph, the at least one first linking edge connecting a first canonical node of the plurality of canonical nodes and a corresponding first subgraph node of the first plurality of nodes in the first subgraph; and at least one second linking edge between the canonical layer and the second subgraph, the at least one second linking edge connecting a second canonical node of the plurality of canonical nodes and a corresponding first subgraph node of the second plurality of nodes in the second subgraph, wherein there are no linking edges between the first subgraph and the second subgraph to directly connect any node of the first plurality of nodes in the first subgraph and any node of the second plurality of nodes in the second subgraph, such that the only connections between the first subgraph and the second subgraph are via the canonical layer.

47. A method for building a Roam Knowledge Graph (RKG) in a computer memory, the method comprising:

A) downloading at least one first file from a first dataset to a first namespace in the computer memory;

B) imputing and/or normalizing first data in the at least one first file to provide at least one cleaned first dataset file;

C) defining a first graph schema for the first dataset;

D) generating a first configuration file for the first graph schema;

E) applying the first configuration file for the first graph schema to the at least one cleaned first dataset file to generate at least one first dataset graph file; and F) importing the at least one first dataset graph file into a graph database management system to render a first subgraph of the RKG in the first namespace in the computer memory.

48. The method of Example 47, further comprising:
performing A), B), E) and F) periodically based at least in part on a dynamic nature of the first dataset.

49. The method of Example 47, further comprising:

G) downloading at least one second file from a second dataset to a second namespace in the computer memory;

H) imputing and/or normalizing second data in the at least one second file to provide at least one cleaned second dataset file;

I) defining a second graph schema for the second dataset;

J) generating a second configuration file for the second graph schema;

K) applying the second configuration file for the second graph schema to the at least one cleaned second dataset file to generate at least one second dataset graph file; and L) importing the at least one second dataset graph file into the graph database management system to render a second subgraph of the RKG in the second namespace in the computer memory.

50. The method of Example 49, further comprising:
performing G), H), K) and L) periodically based at least in part on a dynamic nature of the second dataset.

51. The method of Example 50, further comprising:
performing A), B), E) and F) periodically based at least in part on a dynamic nature of the first dataset.

52. The method of Example 49, wherein:
the first subgraph includes a first plurality of nodes and at least one first subgraph edge connecting two nodes of the first plurality of nodes;
the second subgraph includes a second plurality of nodes;
the first dataset includes first information relating to a first plurality of entities having a first entity type;
the first plurality of nodes in the first subgraph respectively represent at least some of the first plurality of entities having the first entity type, the first plurality of nodes having a first node type corresponding to the first entity type;
the at least one first subgraph edge connecting the two nodes of the first plurality of nodes represents a first relationship of a first relationship type between two entities of the first plurality of entities represented by the two nodes, the at least one first subgraph edge having a first edge type corresponding to the first relationship type;
the second dataset includes second information relating to a second plurality of entities having a second entity type; and the second plurality of nodes in the second subgraph respectively represent at least some of the second plurality of entities having the second entity type, the second plurality of nodes having a second node type corresponding to the second entity type.

53. The method of Example 49, further comprising:
M) generating a canonical layer of the RKG, the canonical layer logically stored in a third namespace of the computer memory and including a plurality of canonical nodes, wherein:
each canonical node of the plurality of canonical nodes is unique and found only once in the canonical layer;
each canonical node has one canonical node type of a plurality of canonical node types; and
the plurality of canonical node types includes at least one of the first node type or the second node type.

54. The method of Example 53, wherein the RKG is a graph representation of electronic information pertaining to at least one domain of activity and/or knowledge, and wherein M) comprises:
M1) selecting respective canonical node types of the plurality of canonical node types based at least in part on a significance and/or a prevalence of the respective canonical node types in the at least one domain of activity and/or knowledge.

55. The method of Example 54, wherein:
the at least one domain comprises health care; and
M1) comprises selecting the respective canonical node types to include at least one of:
disease;
drug;
FDA device code;
FDA device name;
geography;
health care organization;
health care professional;
hospital;
manufacturer;
procedure;
industry event;
time; or
specialty.

56. The method of Example 53, wherein:
M) further comprises:
M1) selecting the first node type in the first subgraph;
M2) determining if the first node type corresponds to a first canonical node type of the plurality of canonical node types;
M3) if the first node type corresponds to the first canonical node type, determining if the canonical layer already includes canonical nodes having the first canonical node type;
M4) if in M3) the canonical layer does not already include canonical nodes having the first canonical node type, copying all nodes having the first node type from the first subgraph to the canonical layer;
M5) if in M3) the canonical layer does already include canonical nodes having the first canonical node type, determining if a first number of canonical nodes in the canonical layer having the first canonical node type is less than a second number of nodes in the first subgraph having the first node type; and
M6) if in M5) the first number is less than the second number, copying delta nodes having the first node type and having no corresponding nodes in the canonical layer from the first subgraph to the canonical layer.

57. The method of Example 56, wherein M) further comprises:
M7) generating a plurality of first linking edges between respective pairs of corresponding nodes including the first plurality of nodes in the first subgraph having the first node type and the canonical nodes in the canonical layer having the first canonical node type.

58. The method of Example 57, wherein:
the first information included in the first dataset further relates to a third plurality of entities having a third entity type;
the first subgraph includes a third plurality of nodes respectively representing at least some of the third plurality of entities having the third entity type, the third plurality of nodes having a third node type corresponding to the third entity type; and
M) further comprises:
M8) selecting the third node type in the first subgraph;
M9) determining if the third node type corresponds to a second canonical node type of the plurality of canonical node types;
M10) if the third node type corresponds to the second canonical node type, determining if the canonical layer already includes canonical nodes having the second canonical node type;
M11) if in M10) the canonical layer does not already include canonical nodes having the second canonical node type, copying all nodes having the third node type from the first subgraph to the canonical layer;
M12) if in M10) the canonical layer does already include canonical nodes having the second canonical node type, determining if a first number of canonical nodes in the canonical layer having the second canonical node type is less than a second number of nodes in the first subgraph having the third node type; and
M13) if in M12) the first number is less than the second number, copying delta nodes having the third node type and having no corresponding nodes in the canonical layer from the first subgraph to the canonical layer.

59. The method of Example 58, wherein M) further comprises:
M14) generating a plurality of second linking edges between respective pairs of corresponding nodes including the third plurality of nodes in the first subgraph having the third node type and the canonical nodes in the canonical layer having the second canonical node type.

60. The method of Example 59, wherein:
M) further comprises:
M15) selecting the second node type in the second subgraph;
M16) determining if the second node type corresponds to a third canonical node type of the plurality of canonical node types;
M17) if the second node type corresponds to the third canonical node type, determining if the canonical layer already includes canonical nodes having the third canonical node type;
M18) if in M17) the canonical layer does not already include canonical nodes having the third canonical node type, copying all nodes having the second node type from the second subgraph to the canonical layer;
M19) if in M17) the canonical layer does already include canonical nodes having the third canonical node type, determining if a first number of canonical nodes in the canonical layer having the third canonical node type is less than a second number of nodes in the second subgraph having the second node type; and M20) if in M19) the first number is less than the second number, copying delta nodes having the second node type and having no corresponding nodes in the canonical layer from the second subgraph to the canonical layer.

61. The method of Example 60, wherein M) further comprises:

M21) generating a plurality of third linking edges between respective pairs of corresponding nodes including the second plurality of nodes in the second subgraph having the second node type and the canonical nodes in the canonical layer having the third canonical node type.

CONCLUSION

All parameters, dimensions, materials, and configurations described herein are meant to be exemplary and that the actual parameters, dimensions, materials, and/or configurations will depend upon the specific application or applications for which the inventive teachings is/are used. It is to be understood that the foregoing embodiments are presented primarily by way of example and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in multiple ways. For example, embodiments may be implemented using hardware, software or a combination thereof. When implemented in software, the software code can be executed on a suitable processor or collection of processors, whether provided in a single computer or distributed among multiple computers.

Figure 36:
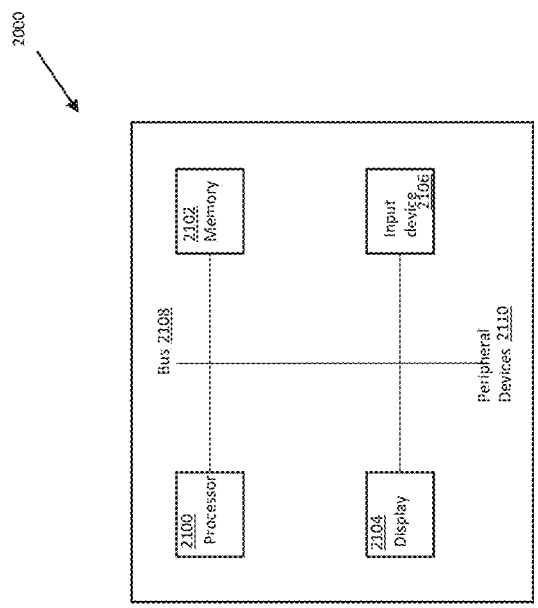
FIG. 36 illustrates an example computing device that can implement the inventive concepts disclosed herein.

For example, the inventive concepts disclosed herein (e.g., RKG in FIG. 1) can be implemented by one of more computing devices, such as computing device 2000 in FIG. 36. Instructions to implement the inventive concepts herein written as software code that can be executed by processor 2100. Memory 2102 can be used to store the inventive graphs, data sets, software instructions to implement the inventive concepts, etc. The display 2104 can provide a user interface that outputs one or more inventive concept, or results of the inventive concepts disclosed herein. A user can interact with the computing device via an input device 2106. Each of the components of the computing device 2000 can be connected to each other via a bus 2108.

An example of a computing device 2000 can include a computer. Further, it should be appreciated that a computer may be embodied in a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in a suitable form, including a local area network or a wide area network, such as an enterprise network, and intelligent network (IN) or the Internet. Such networks may be based on a suitable technology and may operate according to a suitable protocol and may include wireless networks, wired networks or fiber optic networks.

The various methods or processes outlined herein may be coded as software that is executable on one or more processors that employ a suitable operating systems or platform. Additionally, such software may be written using one or more suitable programming languages and/or programming or scripting tools, and also may be compiled as executable machine language code or intermediate code that is executed on a framework or virtual machine. Some implementations may specifically employ one or more of a particular operating system or platform and a particular programming language and/or scripting tool to facilitate execution.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or"

as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A data storage and retrieval system for a computer memory, the system comprising:
   at least one computer memory; and
   at least one processor communicatively coupled to the at least one computer memory, wherein upon execution by the at least one processor of processor-executable instructions, the at least one processor configures the at least one computer memory according to a knowledge graph, the knowledge graph comprising:
   a first subgraph including a first plurality of nodes and at least one first subgraph edge connecting two nodes of the first plurality of nodes, the first subgraph representing a first dataset according to a first graph schema, the first dataset being logically stored in a first namespace of the at least one computer memory;
   a second subgraph including a second plurality of nodes, the second subgraph representing a second dataset according to a second graph schema, the second dataset being logically stored in a second namespace of the at least one computer memory different from the first namespace;
   a canonical layer logically stored in a third namespace of the computer memory, the canonical layer including a plurality of canonical nodes, each canonical node of the plurality of canonical nodes being unique and found only once in the canonical layer;
   at least one first linking edge between the canonical layer and the first subgraph, the at least one first linking edge connecting a first canonical node of the plurality of canonical nodes and a corresponding first subgraph node of the first plurality of nodes in the first subgraph; and
   at least one second linking edge between the canonical layer and the second subgraph, the at least one second linking edge connecting a second canonical node of the plurality of canonical nodes and a corresponding first subgraph node of the second plurality of nodes in the second subgraph,
   wherein there are no linking edges between the first subgraph and the second subgraph to directly connect any node of the first plurality of nodes in the first subgraph and any node of the second plurality of nodes in the second subgraph, such that the only connections between the first subgraph and the second subgraph are via the canonical layer.

2. The system of claim 1, further comprising:
   at least one third linking edge between the canonical layer and the second subgraph, the at least one third linking edge connecting the first canonical node of the plurality of canonical nodes and a corresponding second subgraph node of the second plurality of nodes in the second subgraph, such that the first canonical node is connected to both of the corresponding first subgraph node of the first plurality of nodes in the first subgraph and the corresponding second subgraph node of the second plurality of nodes in the second subgraph.

3. The system of claim 1, further comprising:
   at least one canonical layer edge connecting at least one of the first canonical node or the second canonical node of the plurality of canonical nodes in the canonical layer with at least one other canonical node of the plurality of canonical nodes in the canonical layer.

4. The system of claim 1, wherein:
   the at least one first subgraph edge represents a first relationship between the two nodes of the first plurality of nodes, the first relationship having a first relationship type;
   the at least one first subgraph edge has a first edge type corresponding to the first relationship type; and
   the first edge type is based on at least one of:
   at least one attribute of at least one of the two nodes;
   a plurality of relationships between respective entities of a first plurality of entities specified by first information in the first dataset; or
   at least one trained model that predicts the first relationship type with a corresponding probability.

5. The system of claim 1, wherein the first dataset and the second dataset are heterogenous datasets.

6. The system of claim 1, wherein:
   the first dataset is from a first source;
   the first namespace has a first namespace label that identifies the first source;
   the second dataset is from a second source different from the first source; and the second namespace has a second namespace label that identifies the second source.

7. The system of claim 1, wherein:
the first dataset includes first information relating to a first plurality of entities having a first entity type;
the first plurality of nodes in the first subgraph respectively represent at least some of the first plurality of entities having the first entity type, the first plurality of nodes having a first node type corresponding to the first entity type; and
the at least one first subgraph edge connecting the two nodes of the first plurality of nodes represents a first relationship of a first relationship type between two entities of the first plurality of entities represented by the two nodes, the at least one first subgraph edge having a first edge type corresponding to the first relationship type.

8. At least one non-transitory computer-readable medium encoded with processor-executable instructions that, when executed by at least one processor, cause the at least one processor to configure at least one computer memory according to a knowledge graph, the knowledge graph comprising:
a first subgraph including a first plurality of nodes and at least one first subgraph edge connecting two nodes of the first plurality of nodes, the first subgraph representing a first dataset according to a first graph schema, the first dataset being logically stored in a first namespace of the computer memory;
a second subgraph including a second plurality of nodes, the second subgraph representing a second dataset according to a second graph schema, the second dataset being logically stored in a second namespace of the computer memory different from the first namespace;
canonical layer logically stored in a third namespace of the computer memory, the canonical layer including a plurality of canonical nodes, each canonical node of the plurality of canonical nodes being unique and found only once in the canonical layer;
at least one first linking edge between the canonical layer and the first subgraph, the at least one first linking edge connecting a first canonical node of the plurality of canonical nodes and a corresponding first subgraph node of the first plurality of nodes in the first subgraph; and
at least one second linking edge between the canonical layer and the second subgraph, the at least one second linking edge connecting a second canonical node of the plurality of canonical nodes and a corresponding first subgraph node of the second plurality of nodes in the second subgraph,
wherein there are no linking edges between the first subgraph and the second subgraph to directly connect any node of the first plurality of nodes in the first subgraph and any node of the second plurality of nodes in the second subgraph, such that the only connections between the first subgraph and the second subgraph are via the canonical layer.

9. A method for operating a data storage and retrieval system for a computer memory, the system comprising at least one computer memory; and at least one processor communicatively coupled to the at least one computer memory, the method comprising:
configuring the at least one computer memory according to a knowledge graph upon execution by the at least one processor of processor-executable instructions, wherein the knowledge graph comprises:
a first subgraph including a first plurality of nodes and at least one first subgraph edge connecting two nodes of the first plurality of nodes, the first subgraph representing a first dataset according to a first graph schema, the first dataset being logically stored in a first namespace of the at least one computer memory;
a second subgraph including a second plurality of nodes, the second subgraph representing a second dataset according to a second graph schema, the second dataset being logically stored in a second namespace of the at least one computer memory different from the first namespace;
a canonical layer logically stored in a third namespace of the computer memory, the canonical layer including a plurality of canonical nodes, each canonical node of the plurality of canonical nodes being unique and found only once in the canonical layer;
at least one first linking edge between the canonical layer and the first subgraph, the at least one first linking edge connecting a first canonical node of the plurality of canonical nodes and a corresponding first subgraph node of the first plurality of nodes in the first subgraph; and
at least one second linking edge between the canonical layer and the second subgraph, the at least one second linking edge connecting a second canonical node of the plurality of canonical nodes and a corresponding first subgraph node of the second plurality of nodes in the second subgraph,
wherein there are no linking edges between the first subgraph and the second subgraph to directly connect any node of the first plurality of nodes in the first subgraph and any node of the second plurality of nodes in the second subgraph, such that the only connections between the first subgraph and the second subgraph are via the canonical layer.

10. The method of claim 9, further comprising:
at least one third linking edge between the canonical layer and the second subgraph, the at least one third linking edge connecting the first canonical node of the plurality of canonical nodes and a corresponding second subgraph node of the second plurality of nodes in the second subgraph, such that the first canonical node is connected to both of the corresponding first subgraph node of the first plurality of nodes in the first subgraph and the corresponding second subgraph node of the second plurality of nodes in the second subgraph.

11. The method of claim 9, further comprising:
at least one canonical layer edge connecting at least one of the first canonical node or the second canonical node of the plurality of canonical nodes in the canonical layer with at least one other canonical node of the plurality of canonical nodes in the canonical layer.

12. The method of claim 9, wherein:
the at least one first subgraph edge represents a first relationship between the two nodes of the first plurality of nodes, the first relationship having a first relationship type;
the at least one first subgraph edge has a first edge type corresponding to the first relationship type; and
the first edge type is based on at least one of:
at least one attribute of at least one of the two nodes;
a plurality of relationships between respective entities of a first plurality of entities specified by first information in the first dataset; or
at least one trained model that predicts the first relationship type with a corresponding probability.

13. The method of claim 9, wherein the first dataset and the second dataset are heterogenous datasets.

14. The method of claim 9, wherein:
the first dataset is from a first source;
the first namespace has a first namespace label that identifies the first source;
the second dataset is from a second source different from the first source; and
the second namespace has a second namespace label that identifies the second source.

15. The method of claim 9, wherein:
the first dataset includes first information relating to a first plurality of entities having a first entity type;
the first plurality of nodes in the first subgraph respectively represent at least some of the first plurality of entities having the first entity type, the first plurality of nodes having a first node type corresponding to the first entity type; and
the at least one first subgraph edge connecting the two nodes of the first plurality of nodes represents a first relationship of a first relationship type between two entities of the first plurality of entities represented by the two nodes, the at least one first subgraph edge having a first edge type corresponding to the first relationship type.

* * * * *

UNITED STATES PATENT AND TRADEMARK OFFICE
CERTIFICATE OF CORRECTION

| | | |
|---|---|---|
| PATENT NO. | : 12,131,262 B2 | Page 1 of 1 |
| APPLICATION NO. | : 17/355046 | |
| DATED | : October 29, 2024 | |
| INVENTOR(S) | : Christopher Potts et al. | |

It is certified that error appears in the above-identified patent and that said Letters Patent is hereby corrected as shown below:

In the Claims

Column 71, Claim 8, Line 35 should read:
"a canonical layer logically stored in a third namespace of"

Signed and Sealed this
Fourth Day of March, 2025

Coke Morgan Stewart
*Acting Director of the United States Patent and Trademark Office*